US012059565B1

(12) United States Patent
Guay et al.

(10) Patent No.: US 12,059,565 B1
(45) Date of Patent: Aug. 13, 2024

(54) METHODS AND SYSTEMS FOR MODULATING UNCONSCIOUSNESS OR ANESTHESIA IN A SUBJECT

(71) Applicants: WASHINGTON UNIVERSITY, St. Louis, MO (US); THE GENERAL HOSPITAL CORPORATION, Boston, MA (US)

(72) Inventors: Christian Guay, St. Louis, MO (US); Ben Palanca, St. Louis, MO (US); Emery N. Brown, Boston, MA (US)

(73) Assignees: WASHINGTON UNIVERSITY, St. Louis, MO (US); THE GENERAL HOSPITAL CORPORATION, Boston, MA (US)

( * ) Notice: Subject to any disclaimer, the term of this patent is extended or adjusted under 35 U.S.C. 154(b) by 495 days.

(21) Appl. No.: 17/128,845

(22) Filed: Dec. 21, 2020

Related U.S. Application Data

(60) Provisional application No. 62/950,227, filed on Dec. 19, 2019.

(51) Int. Cl.
*A61N 1/18* (2006.01)
*A61K 45/06* (2006.01)
*A61N 1/04* (2006.01)
*A61N 1/36* (2006.01)

(52) U.S. Cl.
CPC .......... *A61N 1/36021* (2013.01); *A61K 45/06* (2013.01); *A61N 1/0456* (2013.01); *A61N 1/36031* (2017.08)

(58) Field of Classification Search
CPC .............. A61N 1/0568; A61N 1/36021; A61N 1/36031; A61N 1/0456
See application file for complete search history.

(56) References Cited

U.S. PATENT DOCUMENTS

| | | | |
|---|---|---|---|
| 6,567,702 B1 | 5/2003 | Nekhendzy et al. | |
| 7,677,734 B2 * | 3/2010 | Wallace | G02B 27/017 353/18 |
| 7,986,996 B2 | 7/2011 | Bell | |
| 10,130,788 B2 | 11/2018 | Garcia Molina et al. | |
| 10,758,175 B2 | 9/2020 | Grossman et al. | |
| 2010/0160998 A1 * | 6/2010 | Bell | A61N 1/36021 607/46 |

(Continued)

FOREIGN PATENT DOCUMENTS

FR 2684872 A1 6/1993

OTHER PUBLICATIONS

Absalom AR et al. (2016). Target-Controlled Infusion: A Mature Technology. Anesth Analg. vol. 122, No. 1: pp. 70-78.

(Continued)

*Primary Examiner* — Alyssa M Alter

(57) ABSTRACT

Among the various aspects of the present disclosure is the provision of methods and systems for (i) modulating, enhancing, or maintaining slow waves using phase-locked neurostimulation; (ii) modulating, enhancing, or maintaining unconsciousness; or (iii) reducing the amount of anesthesia required in a subject. Briefly, therefore, the present disclosure is directed to applying neurostimulation to the brain of a subject to enhance anesthesia, thereby decreasing drug requirements of anesthesia.

23 Claims, 11 Drawing Sheets

(56) References Cited

U.S. PATENT DOCUMENTS

| | | | | |
|---|---|---|---|---|
| 2012/0112909 | A1* | 5/2012 | Baughman | A61B 5/38 340/540 |
| 2014/0148636 | A1* | 5/2014 | Best | A61N 2/002 607/3 |
| 2017/0020447 | A1 | 1/2017 | Grossman et al. | |
| 2017/0304587 | A1 | 10/2017 | Santostasi et al. | |
| 2019/0143073 | A1 | 5/2019 | Grossman et al. | |

OTHER PUBLICATIONS

Akeju O et al. (2016). Spatiotemporal Dynamics of Dexmedetomidine-Induced Electroencephalogram Oscillations. PLoS One. vol. 11, No. 10:e0163431. 18 pages.

Akeju O et al. (2018). Dexmedetomidine promotes biomimetic non-rapid eye movement stage 3 sleep in humans: A pilot study. Clin Neurophysiol. vol. 129, No. 1: pp. 69-78.

Aldrete JA (1995). The post-anesthesia recovery score revisted. J Clin Anesth. vol. 7, No. 1, pp. 89-91.

American Society of Anesthesiologists Task Force (2017). Practice Guidelines for Preoperative Fasting and the Use of Pharmacologic Agents to Reduce the Risk of Pulmonary Aspiration: Application to Healthy Patients Undergoing Elective Procedures: An Updated Report by the American Society of Anesthesiologists Task Force on Preoperative Fasting and the Use of Pharmacologic Agents to Reduce the Risk of Pulmonary Aspiration. Anesthesiology. vol. 126, No. 3: pp. 376-393.

Andrillon T et al. (2020). Revisiting the value of polysomnographic data in insomnia: more than meets the eye. Sleep Medicine, vol. 66: pp. 184-200.

Arnal PJ et al. (Jun. 2019). The Dreem Headband as an Alternative to Polysomnography for EEG Signal Acquisition and Sleep Staging. BioRxiv 2019:662734, 11 pages.

Bellesi M et al. (2014). Enhancement of sleep slow waves: underlying mechanisms and practical consequences. Front Syst Neurosci. vol. 8, No. 208: 17 pages.

Besedovsky L et al. (2017). Auditory closed-loop stimulation of EEG slow oscillations strengthens sleep and signs of its immune-supportive function. Nat Commun. vol. 8, No. 1984: 8 pages.

Bloor BC et al. (1992). Effects of intravenous dexmedetomidine in humans. II. Hemodynamic changes. Anesthesiology. vol. 77, No. 6: pp. 1134-1142.

Borbely AA (1982). A two process model of sleep regulation. Hum Neurobiol. vol. 1, No. 3: pp. 195-204.

Brown EN, Lydic R, and Schiff NF (2010). General anesthesia, sleep, and coma. N Engl J Med. vol. 363, No. 27: pp. 2638-2650.

Brown EN, Pavone KJ, and Naranjo M (2018). Multimodal General Anesthesia: Theory and Practice. Anesth Analg. vol. 127, No. 5: pp. 1246-1258.

Buysse DJ et al. (1989). The Pittsburgh Sleep Quality Index: a new instrument for psychiatric practice and research. Psychiatry Res. vol. 28, No. 2: pp. 193-213.

Casagrande JT, Pike MC, and Smith PG (1978). An improved approximate formula for calculating sample sizes for comparing two binomial distributions. Biometrics vol. 34, No. 3: pp. 483-486.

Chan AW et al. (2013). Spirit 2013 statement: defining standard protocol items for clinical trials. Ann Intern Med vol. 158, No. 3: pp. 200-207.

Chauvette S et al. (2011). Properties of slow oscillation during slow-wave sleep and anesthesia in cats. J Neurosci. vol. 31, No. 42: pp. 14998-15008.

Colin PJ et al. (2017). Dexmedetomidine pharmacodynamics in healthy volunteers: 2. Haemodynamic profile. Br J Anaesth. vol. 119, No. 2: pp. 211-220.

Colin PJ et al. (2017). Dexmedetomidine pharmacokinetic-pharmacodynamic modelling in healthy volunteers: 1. Influence of arousal on bispectral index and sedation. Br J Anaesth. vol. 119, No. 2: pp. 200-210.

Debellemaniere E et al. (2018). Performance of an Ambulatory Dry-EEG Device for Auditory Closed-Loop Stimulation of Sleep Slow Oscillations in the Home Environment. Front Hum Neurosci. vol. 12, No. 88: 15 pages.

Delorme A and Makeig S (2004). EEGLAB: an open source toolbox for analysis of single-trial EEG dynamics including independent component analysis. J Neurosci Methods vol. 134, No. 1: pp. 9-21.

Ebert TJ et al. (2000). The effects of increasing plasma concentrations of dexmedetomidine in humans. Anesthesiology. vol. 93, No. 2: pp. 382-394.

Evered L et al. (2018). Recommendations for the nomenclature of cognitive change associated with anaesthesia and surgery-2018. Br J Anaesth. vol. 121, No. 5: pp. 1005-1012.

Garcia-Molina G et al. (2018). Closed-loop system to enhance slow-wave activity. J Neural Eng. vol. 15, No. 6:066018. 11 pages.

Gaskell Al et al. (2017). Frontal alpha-delta EEG does not preclude volitional response during anaesthesia: prospective cohort study of the isolated forearm technique. Br J Anaesth. vol. 119, No. 4: pp. 664-673.

Goldman B. (1984). Can Aime Limoge sell electroanesthesia to North America? Can Med Assoc J. vol. 130, No. 9: pp. 1191-1193, 1196-1197, 1200.

Greene RW and Frank MG. (2010). Slow wave activity during sleep: functional and therapeutic implications. Neuroscientist vol. 16, No. 6: pp. 618-633.

Grimaldi D et al. (May 2019). Strengthening sleep-autonomic interaction via acoustic enhancement of slow oscillations. Sleep. vol. 42, No. 5: 11 pages.

Guldenmund P et al. (2017). Brain functional connectivity differentiates dexmedetomidine from propofol and natural sleep. Br J Anaesth. vol. 119, No. 4: pp. 674-684.

Hannivoort LN and et al. (2015). Development of an Optimized Pharmacokinetic Model of Dexmedetomidine Using Target-controlled Infusion in Healthy Volunteers. Anesthesiology. vol. 123, No. 2: pp. 357-367.

Haroutounian S et al. (2014). Primary afferent input critical for maintaining spontaneous pain in peripheral neuropathy. Pain. vol. 155, No. 7: pp. 1272-1279.

Hoddes E et al. (1973). Quantification of sleepiness: a new approach. Psychophysiology vol. 10, No. 4: pp. 431-436.

Kerkhofs M and Lavie P (2000). Frederic Bremer 1892-1982: a pioneer in sleep research. Sleep Med Rev. vol. 4, No. 5: pp. 505-514.

Lee SH and Dan Y (2012). Neuromodulation of brain states. Neuron. vol. 76, No. 1: pp. 209-222.

Leger D et al. (2018). Slow-wave sleep: From the cell to the clinic. Sleep Med Rev. vol. 41: pp. 113-132.

Leminen MM et al. (2017). Enhanced Memory Consolidation via Automatic Sound Stimulation During Non-REM Sleep. Sleep. vol. 40, No. 3: 10 pages.

Lewis LD et al. (2012). Rapid fragmentation of neuronal networks at the onset of propofol-induced unconsciousness. Proc Natl Acad Sci U S A. vol. 109, No. 49: pp. E3377-E3386.

Maier KL et al. (2017). Protocol for the Reconstructing Human Consciousness and Cognition Study. Front Hum Neurosci. vol. 11, No. 284: 8 pages.

Mantz J et al. (1992). Transcranial electrical stimulation with Limoge's currents decreases halothane requirements in rats. Evidence for the involvement of endogenous opioids. Anesthesiology. vol. 76, No. 2: pp. 253-260.

Marshall L et al. (2006). Boosting slow oscillations during sleep potentiates memory. Nature. vol. 444, No. 7119: pp. 610-613.

Massimini M et al. (2007). Triggering sleep slow waves by transcranial magnetic stimulation. Proc Natl Acad Sci U S A. vol. 104, No. 20: pp. 8496-8501.

Mignon A et al. (1996). Transcutaneous cranial electrical stimulation (Limoge's currents) decreases early buprenorphine analgesic requirements after abdominal surgery. Anesth Analg. vol. 83, No. 4: pp. 771-775.

Murphy M et al. (2011). Propofol anesthesia and sleep: a high-density EEG study. Sleep. vol. 34, No. 3: pp. 283-291A.

Naveau S et al. (1992). Analgesic effect of transcutaneous cranial electrostimulation in patients treated by Nd:YAG laser for cancer of

(56) References Cited

OTHER PUBLICATIONS the rectum. A double-blind randomized trial. Gastroenterol Clin Biol. vol. 16, No. 1: pp. 8-11. English translation attached.

Neske GT. (2016). The Slow Oscillation in Cortical and Thalamic Networks: Mechanisms and Functions. Front Neural Circuits. vol. 9, No. 88: 25 pages.

Ngo HV et al. (2013). Auditory closed-loop stimulation of the sleep slow oscillation enhances memory. Neuron. vol. 78, No. 3: pp. 545-553.

Ngo HV et al. (2013). Induction of slow oscillations by rhythmic acoustic stimulation. J Sleep Res. vol. 22, No. 1: pp. 22-31.

Ni Mhuircheartaigh R et al. (2013). Slow-wave activity saturation and thalamocortical isolation during propofol anesthesia in humans. Sci Transl Med. vol. 5, No. 208, 208ra148, 8 pages.

Ong JL et al. (2016). Effects of phase-locked acoustic stimulation during a nap on EEG spectra and declarative memory consolidation. Sleep Med. vol. 20: pp. 88-97.

Palanca BJ et al. (2015). Resting-state Functional Magnetic Resonance Imaging Correlates of Sevoflurane-induced Unconsciousness. Anesthesiology vol. 123, No. 2: pp. 346-356.

Palanca BJ et al. (2018). Cognitive and Neurophysiological Recovery Following Electroconvulsive Therapy: A Study Protocol. Front Psychiatry vol. 9, No. 171: 13 pages.

Pandya AN, Majid SZ, Desai MS. (2020). The Orgins, Evolution, and Spread of Anesthesia Monitoring Standards: From Boston to Across the World. Anesth Analg. vol. 132, No. 3: pp. 890-898.

Papalambros NA et al. (2017). Acoustic Enhancement of Sleep Slow Oscillations and Concomitant Memory Improvement in Older Adults. Front Hum Neurosci. vol. 11, No. 109: 14 pages.

Prerau MJ et al. (2014). Tracking the sleep onset process: an empirical model of behavioral and physiological dynamics. PLoS Comput Biol. vol. 10, No. 10, e1003866, 19 pages.

Prerau MJ et al. (2017). Sleep Neurophysiological Dynamics Through the Lens of Multitaper Spectral Analysis. Physiology (Bethesda). vol. 32, No. 1: pp. 60-92.

Purdon PL and Brown En. (2017). Clinical Electroencephalography for the Anesthesiologist. Available from: https://web.archive.org/web/20170304213534/https://www.phscpd.org/activities/activity-detail/clinical-electroencephalography-for-the-anesthesiologist. 2 pages.

Purdon PL et al. (2013). Electroencephalogram signatures of loss and recovery of consciousness from propofol. Proc Natl Acad Sci U S A vol. 110, No. 12: pp. E1142-E1151.

Purdon PL et al. (2015). Clinical Electroencephalography for Anesthesiologists: Part I: Background and Basic Signatures. Anesthesiology. vol. 123, No. 4: pp. 937-960.

Purdon PL, Colvin CA, and Brown En. (2019). EEG for Anesthesia. International Anesthesia Research Society. Available from: http://eegforanesthesia.iars.org. 1 page.

Reshef ER, Schiff ND, and Brown En. (Mar. 2019). A Neurologic Examination for Anesthesiologists: Assessing Arousal Level during Induction, Maintenance, and Emergence. Anesthesiology. vol. 130, No. 3: pp. 462-471.

Riedner BA et al. (2007). Sleep homeostasis and cortical synchronization: III. A high-density EEG study of sleep slow waves in humans. Sleep. vol. 30, No. 12: pp. 1643-1657.

Rolke R et al. (2006). Quantitative sensory testing in the German Research Network on Neuropathic Pain (DFNS): standardized protocol and reference values. Pain. vol. 123, No. 3: pp. 231-243.

Santostasi G et al. (2016). Phase-locked loop for precisely timed acoustic stimulation during sleep. J Neurosci Methods. vol. 259: pp. 101-114.

Scheinin A et al. (2018). Differentiating Drug-related and State-related Effects of Dexmedetomidine and Propofol on the Electroencephalogram. Anesthesiology. vol. 129, No. 1: pp. 22-36.

Schmid W et al. (2020). Brainwave entrainment to minimise sedative drug doses in paediatric surgery: a randomised controlled trial. Br J Anaesth. vol. 125, No. 3: pp. 330-335.

Scholkmann F, Boss J, and Wolf M. (2012). An Efficient Algorithm for Automatic Peak Detection in Noisy Periodic and Quasi-Periodic Signals. Algorithms vol. 5: pp. 588-603.

Sleigh JW et al. (2018) Electroencephalographic Arousal Patterns Under Dexmedetomidine Sedation. Anesth Analg. vol. 127, No. 4: pp. 951-959.

Smith RH, Tatsuno J, and Zouhar RL (1967). Electroanesthesia: a review—1966. Anesth Analg. vol. 46, No. 1: pp. 109-125.

Stanley TH et al. (1982). Transcutaneous cranial electrical stimulation decreases narcotic requirements during neurolept anesthesia and operation in man. Anesth Analg. vol. 61, No. 10: pp. 863-866.

Steriade M, Timofeev I, and Grenier F (2001). Natural waking and sleep states: a view from inside neocortical neurons. J Neurophysiol. vol. 85, No. 5: pp. 1969-1985.

Tadel F et al. (2011) Brainstorm: a user-friendly application for MEG/EEG analysis. Comput Intell Neurosci. vol. 2011, No. 879716: 13 pages.

Talke P and Anderson BJ (2018). Pharmacokinetics and pharmacodynamics of dexmedetomidine-induced vasoconstriction in healthy volunteers. Br J Clin Pharmacol vol. 84, No. 6: pp. 1364-1372.

Tononi G and Cirelli C (2014). Sleep and the price of plasticity: from synaptic and cellular homeostasis to memory consolidation and integration. Neuron. vol. 81, No. 1: pp. 12-34.

Vutskits L and Davidson A (2017). Update on developmental anesthesia neurotoxicity. Curr Opin Anaesthesiol. vol. 30, No. 3: pp. 337-342.

Vyazovskiy VV et al. (2009). Cortical firing and sleep homeostasis. Neuron. vol. 63, No. 6: pp. 865-878.

Warnaby CE et al. (2017). Investigation of Slow-wave Activity Saturation during Surgical Anesthesia Reveals a Signature of Neural Inertia in Humans. Anesthesiology. vol. 127, No. 4: pp. 645-657.

Weerink Mas et al. (2017). Clinical Pharmacokinetics and Pharmacodynamics of Dexmedetomidine. Clin Pharmacokinet. vol. 56, No. 8: pp. 893-913.

Xi C et al. (2018). Different effects of propofol and dexmedetomidine sedation on electroencephalogram patterns: Wakefulness, moderate sedation, deep sedation and recovery. PLoS One. vol. 13, No. 6, e0199120, 15 pages.

Yarmolenko PS et al. (2011). Thresholds for thermal damage to normal tissues: an update. Int J Hyperthermia. vol. 27, No. 4: pp. 320-343.

\* cited by examiner

METHODS AND SYSTEMS FOR MODULATING UNCONSCIOUSNESS OR ANESTHESIA IN A SUBJECT

CROSS-REFERENCE TO RELATED APPLICATIONS

This application claims priority from U.S. Provisional Application Ser. No. 62/950,227 filed on 19 Dec. 2019, which is incorporated herein by reference in its entirety.

STATEMENT REGARDING FEDERALLY SPONSORED RESEARCH OR DEVELOPMENT

Not applicable.

MATERIAL INCORPORATED-BY-REFERENCE

Not applicable.

FIELD OF THE INVENTION

The present disclosure generally relates to methods and systems for the enhancement of unconsciousness in a subject.

SUMMARY OF THE INVENTION

Among the various aspects of the present disclosure is the provision of methods and systems for the modulation of unconsciousness or anesthesia in a subject. Briefly, therefore, the present disclosure is directed to applying neurostimulation to the brain of a subject to enhance anesthesia, thereby decreasing drug requirements of anesthesia.

An aspect of the present disclosure provides for a method of augmenting, entraining, modulating, enhancing, or maintaining slow-delta waves in a brain of a subject using phase-locked neurostimulation. In some embodiments, the method comprises (i) administering at least one pharmacological agent to the subject, wherein the pharmacological agent comprising a slow-delta wave enhancing agent, optionally, an anesthetic agent, inducing an endogenous pharmaceutically-induced slow-delta wave in the brain of the subject; (ii) performing an electroencephalogram (EEG) on the subject having the endogenous pharmaceutically-induced slow-delta wave or measuring an electrical signal of the endogenous pharmaceutically-induced slow-delta wave that originates in a brain of the subject; (iii) identifying an endogenous pharmaceutically-induced slow-delta wave electrical signal in the EEG; or (iv) applying neurostimulation to the subject, wherein the neurostimulation is phase-locked to the endogenous pharmaceutically-induced slow-delta wave electrical signal, resulting in an in-phase neurostimulated slow-delta wave. In some embodiments, phase-locking comprises synchronization of neurostimulation to an up-slope of the pharmaceutically-induced slow-delta wave, if not yet neurostimulated, or to the in-phase neurostimulated slow-delta wave, if neurostimulated. In some embodiments, phase-locking comprises: (a) calculating a set of one or more estimates of instantaneous phase and amplitude of the endogenous pharmaceutically-induced slow-delta wave electrical signal or the in-phase neurostimulated slow-delta wave electrical signal; or (b) controlling, based on the set of one or more estimates of instantaneous phase and instantaneous amplitude of the endogenous pharmaceutically-induced slow-delta wave electrical signal or the in-phase neurostimulated slow-delta wave electrical signal, timing of one or more changes in the neurostimulation. In some embodiments, the slow-delta wave has a frequency between about 0.5 Hz and about 4 Hz. In some embodiments, the topography of phase-locking, target frequency bandwidth, stimulation phase, stimulation modalities, or stimulation intensities can be directly adjusted by a user. In some embodiments, each estimate in the set of one or more estimates of instantaneous phase and instantaneous amplitude is calculated based on a specific sample in a specific sample window of the measurements in such a way that: (a) the specific sample window is different than that for any other estimate in the set or (b) the specific sample is more recent than any other sample in the specific sample window. In some embodiments, the neurostimulation comprises audio or acoustic, electrical, magnetic, visual, or ultrasonic stimulation. In some embodiments, each estimate of instantaneous phase and instantaneous amplitude is computed on a millisecond timescale. In some embodiments, the neurostimulation causes the subject to perceive binaural beats. In some embodiments, the neurostimulation is selected from the group consisting of acoustic stimulation, electrical stimulation, magnetic stimulation, or combinations thereof. In some embodiments, the anesthetic agent is a barbiturate or inhaled ether. In some embodiments, the anesthetic agent is selected from the group consisting of propofol, dexmedetomidine, ketamine, remifentanil, nitrous oxide, desflurane, etomidate, sevoflurane, isoflurane, or combinations thereof. In some embodiments, the slow-delta wave inducing agent is selected from the group consisting of gamma hydroxybutyrate (GHB), trazodone, brexanolone, propofol, benzodiazepines, barbiturates, xenon, nitrous oxide, ketamine, halogenated ethers, or combinations thereof. In some embodiments, the anesthetic agent is a combination of anesthetic agents selected from the group consisting of propofol/remifentanil, propofol/dexmedetomidine, dexmedetomidine/remifentanil, sevoflurane/remifentanil, sevoflurane/nitrous oxide, ketamine/remifentanil, or ketamine/propofol, or combinations thereof. In some embodiments, applying the neurostimulation results in enhanced or more stable unconsciousness in the subject when compared to not applying the neurostimulation. In some embodiments, applying the neurostimulation results in a reduced required dose of the pharmacological agent for maintaining unconsciousness in the subject. In some embodiments, applying the neurostimulation enhances GABAergic activity, activates opioid receptors, activates alpha-2 receptors, or inhibits NMDA receptors. In some embodiments, the pharmacological agent induces sleep or an anesthetic state. In some embodiments, for each specific estimate in the set of estimates of instantaneous phase and instantaneous amplitude: (a) the calculating of the specific estimate is based on a specific sample window of the measurements that is different than that for each other estimate in the set; (b) the calculating of the specific estimate is not based on any sample window of the measurements other than the specific sample window; or (c) the calculating comprises performing an inverse discrete Fourier transform that reconstructs only a single sample, which single sample is in the specific sample window and is more recent than the other sample in the specific sample window. In some embodiments, for each specific estimate in the set of estimates of instantaneous phase and instantaneous amplitude, the calculating comprises: (a) reconstructing, by an inverse discrete Fourier transform, a single sample of the measurements or (b) computing the specific estimate based on the single sample and not based on any other sample. In some embodiments, the calculating of instantaneous phase and instantaneous amplitude comprises applying a causal filter in a frequency domain. In some embodiments, for each specific estimate in the set of one or more estimates of instantaneous phase and instantaneous amplitude, the method further comprises: (a) padding and filtering a specific sample window for the specific estimate to create a padded and filtered sample window, in such a way that a difference in value between data points at each end of the padded and filtered sample window is less than a difference in value between data points at each end of the sample window before padding and filtering or (b) performing a discrete Fourier transform and Hilbert transform or zero-crossing method to calculate an analytic representation of the padded and filtered sample window. In some embodiments, for each specific estimate in the set of one or more estimates of instantaneous phase and instantaneous amplitude, the method further comprises: (a) adding padding to a specific sample window for the specific estimate and then filtering the specific sample window to create a padded and filtered sample window or (b) performing a discrete Fourier transform and Hilbert transform or zero-crossing method to calculate an analytic representation of the padded and filtered sample window.

Another aspect of the present disclosure provides for a system for (i) modulating, enhancing, or maintaining slow waves using phase-locked neurostimulation; (ii) modulating, enhancing, or maintaining unconsciousness; or (iii) reducing an amount of anesthesia required in a subject, comprising: (i) a plurality of neurostimulators configured to deliver stimuli to a brain of the subject; (ii) a plurality of electroencephalography (EEG) sensors and amplifiers configured to generate a plurality of EEG signals; or (iii) a central processing unit, wherein the central processing unit is configured to receive and process the plurality of EEG signals; compute a phase-locking algorithm, wherein the algorithm identifies and tracks a slow-delta wave in the plurality of EEG signals; or deliver a transcranial stimulation through a plurality of neurostimulation electrodes during a peak of the slow-delta wave. In some embodiments, the plurality of EEG sensors and amplifiers are configured to generate a plurality of EEG signals from frontal, temporal, parietal, or occipital lobes of the brain of the subject. In some embodiments, topography of phase-locking, target frequency bandwidth, stimulation phase, stimulation modalities, or stimulation intensities can be directly adjusted by a user of the system. In some embodiments, the central processing unit generates the plurality of EEG signals, power spectral density, or slow-delta wave activity (SWA) as output to be viewed by a user of the system. In some embodiments, the neurostimulator produces neurostimulation selected from an electric stimulus, an acoustic stimulus, a magnetic stimulus, an ultrasound stimulus, or a visual stimulus, or a combination thereof. In some embodiments, the acoustic stimulus is characterized by equal energy per octave, optionally, pink noise or 1/f noise. In some embodiments, the system further comprises an infusion pump configured to deliver a pharmacological agent to the subject at an infusion rate sufficient to induce unconsciousness in the subject. In some embodiments, the central processing unit determines when the infusion rate can be reduced or stopped, based on the plurality of EEG signals. In some embodiments, the method further comprises noise-isolating earphones, transcranial electrical stimulation, transcranial magnetic stimulation, ultrasound stimulation, or visual stimulation. In some embodiments, the system is EEG-compatible and does not disrupt slow wave detection.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 5A 0.5 second refractory period. (i) In-phase stimulation (peak-locked). (ii) Anti-phase stimulation (trough-locked). FIG. 5B 2 second refractory period. (i) In-phase stimulation (peak-locked). (ii) Anti-phase stimulation (trough-locked). FIG. 5C 5 second refractory period. (i) In-phase stimulation (peak-locked). (ii) Anti-phase stimulation (trough-locked).

DETAILED DESCRIPTION OF THE INVENTION

Figure 1:
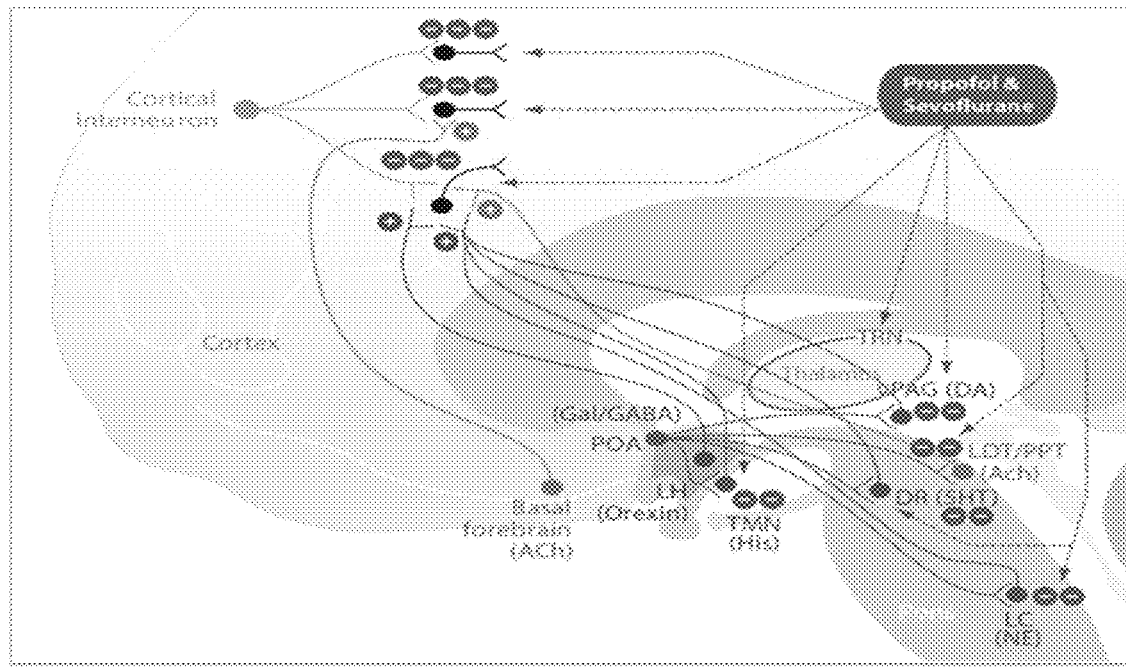
FIG. 1. Neural mechanisms of propofol and sevoflurane. Enhancing inhibitory GABAergic projections of the preoptic area of the hypothalamus onto the ascending activating system induces slow waves. GABAergic tone of cortical interneurons is also enhanced.

The present disclosure is based, at least in part, on the discovery that neurostimulation can be used to enhance anesthesia or unconsciousness in a subject. As described herein, neurostimulation can enhance slow waves in the brain of a subject, which enhances anesthesia and reduces the need for pharmacological anesthetics or reduces the dose of anesthesia required to anesthetize a subject.

One aspect of the present disclosure provides for a novel method of phase-locked neurostimulation during anesthesia. An example is a phase-locked acoustic neurostimulation, but any neurostimulation or combination of neurostimulation can be utilized, such as acoustic, magnetic, visual, and/or ultrasonic stimulation.

Another aspect of the present disclosure provides for a novel method for the toolbox of multimodal anesthesia: phase-locked anesthetic neurostimulators (PLANs). Stated briefly, PLANs maintain anesthetic states by enhancing pharmacologically-induced slow waves using multimodal phase-locked neurostimulation. Enhancing slow waves in this way decreases the probability of a transition from an unconscious state to a conscious state.

Multimodal general anesthesia designs anesthetic states "bottom-up" by combining complementary neural mechanisms. The common EEG endpoint of these mechanisms is the generation of slow waves via Bremer's principle, and continuous infusions and/or inhalation of anesthetic agents to maintain these oscillatory states. Similarly, acoustic, electrical, magnetic, visual, and/or ultrasonic stimulation can be used to maintain slow waves through complementary neural mechanisms: ascending non-lemniscal auditory stimulation pathways, and modulation of cortical electrical and magnetic fields, respectively. Therefore, these stimulation modalities can be integrated into the framework of multimodal anesthesia to maintain anesthetic-induced unconsciousness and further reduce or eliminate pharmacological requirements. Limoge currents have already been used to this effect, albeit without the benefit of phase-locking or the combination of multiple modalities.

One drug example is provided for each anesthetic target (e.g., propofol for GABA), and a single target combination is presented (i.e., GABA+Alpha2). In practice, any drug with activity at an anesthetic target could be used (e.g., replacing propofol with sevoflurane), and any combination of anesthetic targets and neurostimulation modalities can be used to maintain anesthetic states. Furthermore, it is possible that a single drug such as dexmedetomidine may not induce unconsciousness by itself, but that an unconscious state is achieved by enhancing slow waves using phase-locked neurostimulation.

As described herein, phase-locked anesthetic neurostimulators are similar to brain-computer interfaces in that they are composed of three basic components: EEG sensors and amplifiers (i.e., input), a phase-locking algorithm computed on a central processing unit (i.e., computer), and neurostimulation hardware (i.e., output). EEG sensors and amplifiers are commercially available for research and clinical use. The optimal EEG montage used in a PLAN depends on the specific anesthetic agents and stimulation modalities being combined. Ideally, frontal, temporal, parietal, and occipital leads can be included to account for variances in slow wave topography across patients and anesthetics. Multimodal stimulation can be phase-locked to one or multiple electrodes. As stated previously, multiple phase-locking algorithms have been developed to deliver stimuli synchronized with slow wave peaks during natural sleep. Although they share overlapping neural circuits, sleep slow waves and the wide range of anesthetic slow waves are not identical.

Nevertheless, their EEG properties are similar enough that these algorithms require minimal modifications to effectively track and stimulate pharmacologically-induced slow waves. Whereas sleep slow wave enhancement devices are designed to autonomously classify sleep stages and activate stimulation algorithms during unattended N3 sleep, PLANs are designed to interface directly with an attending anesthesiologist who can adjust their settings and use them according to their training and assessment of the clinical scenario. Adjustable settings include topography of phase-locking, target frequency bandwidth, stimulation phase, stimulation modalities, and stimulation intensities. The interface also feeds back key EEG data to the anesthesiologist, including raw EEG, power spectral density, and/or slow wave activity (SWA). The neurostimulation hardware used in PLANs is also already available: noise-isolating earphones, transcranial electrical stimulation, and/or transcranial magnetic stimulation, for example. The implementation of these technologies within PLANs requires that they be EEG-compatible and that they not disrupt slow wave detection. Acoustic stimulation is the easiest to implement, followed by electrical, magnetic, ultrasound, or visual stimulation.

In summary, the technologies required to build PLANs already exist. The significant difference of this technique is the modification and synthesis of existing neurostimulation techniques with EEG phase-locking algorithms to slow waves in the framework of multimodal anesthesia.

Neuromodulation System

A neuromodulation system, as described herein, can be a system that produces stimulation that causes an increase in the amplitude of delta waves such that a subject under anesthesia would require a reduction in an amount of an anesthetic drug than in the absence of the stimulation.

For example, the system can be a system as described in US Pat Pub No. 2019/0143073 or U.S. Pat. No. 10,758,175, incorporated herein by reference. Although this system is directed to modulating alpha waves to induce sleep onset, the inventors, here, have discovered its use (with modifications) in modulating delta waves in a subject under anesthesia, to be administered anesthesia, or having been administered anesthesia.

Here, for anesthesia applications, the topography of phase-locking, target frequency bandwidth, stimulation phase, stimulation modalities, and stimulation intensities can be directly adjusted by a user of the system, which is in contrast to currently available systems for sleep.

Other modifications from currently available systems and methods can include the following.

1. Large scale cycles in brain rhythms are not expected, as observed during sleep (e.g., N1 sleep, N2 sleep, N3 sleep, REM sleep). Therefore, the traditional sleep "phase-gating" used in algorithms to enhance sleep quality are not needed during sedation. The version, as described here, can be a simplified version that distinguishes between "slow waves present" and "slow waves absent" instead of classifying sleep stages.

2. The temporal density and topography of slow waves during sleep and sedation are not identical. This is an ongoing field of scientific inquiry. Some important differences lie in their slopes, maximal amplitudes, and phase-amplitude coupling, all of which can be considered in the algorithms that detect slow wave peaks. One of the CLASS-D objectives (see e.g., Example 3, Example 4) is to compare the features of sleep slow waves with dexmedetomidine-induced slow waves. This data can further refine the phase-locking methods.

3. Sleep-tracking algorithms are designed to be autonomous (for home use), whereas algorithms designed herein for anesthesia interface with which the clinician can interact and modify in real-time according to the patient's physiologic state.

The neurostimulation gating, predicting of the phase-locking, or synchronization of the neurostimulation of the device can be determined, estimated, or performed in a number of ways. For example, the calculation of the up-slope of the endogenous anesthetic-induced slow-delta wave can be used as the gating signal.

Although the device used herein can use an "end-corrected Hilbert transform" (ECHT) to compute an estimated instantaneous phase, in principle, this methodology can use any method of phase-locking neurostimulation. For example, systems can use a "zero-crossing" method.

As an example, phase-locking can be performed by calculating a set of one or more estimates of (a) instantaneous phase of an endogenous pharmaceutically-induced slow-delta wave electrical signal and/or (b) instantaneous amplitude of the endogenous pharmaceutically-induced slow-delta wave electrical signal. The phase-locking can further comprise controlling, based on the set of one or more estimates of instantaneous phase and instantaneous amplitude of the endogenous or induced neurostimulated slow-delta wave, the timing of one or more changes in the neurostimulation.

The present application also describes multimodal stimulation paradigms. For example, audio or acoustic stimulation can be used (see e.g., Example 3 and Example 4), but also others, such as electrical, magnetic, visual, or ultrasonic stimulation can be used individually or in combination (see e.g., Example 1). For example, neurostimulation can be transcranial direct-current stimulation (tDCS) or transcranial magnetic stimulation.

The acoustic stimulus can be characterized by equal energy per octave (e.g., pink noise or 1/f noise), but can be optimized in other ways and for all types of neurostimulation, such as electric stimulus, acoustic stimulus, magnetic stimulus, ultrasound stimulus, or visual stimulus.

Acoustic stimulation can include binaural beats which is a related but distinct method of acoustic stimulation that relies on the difference in frequency between two different acoustic stimuli applied to each ear. For example, binaural beats can be used in multimodal strategies combining neurostimulation methods. Binaural beats have shown promise in a recently published clinical trial, though they did not measure or report any actual EEG data (Schmid et al., Brainwave entrainment to minimise sedative drug doses in paediatric surgery: a randomised controlled trial, Clinical Investigation, Volume 125, Issue 3, pp. 330-335, Sep. 1, 2020).

Slow-Delta Wave Enhancing/Inducing Agents

The methods and systems described herein can enhance slow waves in the brain of a subject which can be initially induced using slow-delta wave enhancing/inducing agents, such as anesthetic agents. Anesthetic agents that can be used with the described systems and methods can be any known in the art to produce slow-delta waves in a subject (see e.g., Barash Clinical Anesthesia, ed. 8, LWW, ISBN-13: 978-1496337009).

Examples of agents used in sedation and anesthesia can include inhaled agents, intravenous (opioid or non-opioid analgesic) agents, and can also include muscle relaxants or other slow-delta wave enhancing agents. Examples of inhaled agents can be Desflurane, Enflurane, Halothane, Isoflurane, Methoxyflurane, Nitrous oxide, Sevoflurane, or Xenon, among others.

The methods and systems described herein can be used with sedation using other agents such as propofol, benzodiazepines, barbiturates, xenon, nitrous oxide, ketamine, and halogenated ethers.

Intravenous agents (non-opioid), though they produce unconsciousness, provide no analgesia (pain relief) and are commonly used with other agents. While many drugs can be used intravenously to produce anesthesia or sedation, the most common are Barbiturates such as Amobarbital (Amytal™) Methohexital (Brevital™), Thiamylal (trade name: Surital™), Thiopental (Penthothal™, referred to as thiopentone in the UK), Benzodiazepines, Diazepam, Lorazepam, Midazolam, Etomidate, Ketamine, or Propofol.

While opioids can produce unconsciousness, they can be less reliable and have undesirable side effects, so, while they may not be used to induce anesthesia, they are frequently used along with other agents such as intravenous non-opioid anesthetics or inhalational anesthetics. Furthermore, they are used to relieve the pain of patients before, during, or after surgery. Examples of some intravenous opioid analgesic agents that have short onset and duration of action and are frequently used during general anesthesia are Alfentanil, Fentanyl, Remifentanil, or Sufentanil.

Examples of some intravenous opioid analgesic agents that have longer onset and duration of action and are frequently used for post-operative pain relief are Buprenorphine, Butorphanol, Diamorphine, also known as heroin, not available for use as an analgesic in any country but the UK, Hydromorphone, Levorphanol, Pethidine, also called meperidine in North America, Methadone, Morphine, Nalbuphine, Oxycodone, not available intravenously in U.S., Oxymorphone, or Pentazocine.

Muscle relaxants (neuromuscular blocking drugs) can also be used before, after, or during anesthesia. Muscle relaxants do not render patients unconscious or relieve pain. Instead, they can be used after a patient is rendered unconscious (induction of anesthesia) to facilitate intubation or surgery by paralyzing skeletal muscle. Examples of depolarizing muscle relaxants are Succinylcholine (also known as suxamethonium in the UK, New Zealand, Australia and other countries, "Celokurin" or "celo" for short in Europe) or Decamethonium. Examples of non-depolarizing muscle relaxants can be short acting muscle relaxants such as Mivacurium or Rapacuronium; intermediate acting muscle relaxants such as Atracurium, Cisatracurium, Rocuronium, Vecuronium; or long acting muscle relaxants such as Alcuronium, Doxacurium, Gallamine, Metocurine, Pancuronium, Pipecuronium, or Tubocurarine.

Other slow wave enhancers that can be administered before, after, or during anesthesia can be GHB, trazodone, or brexanolone.

Any anesthetic agent or slow wave inducing agent or combinations thereof in an amount that can pharmaceutically-induce slow waves can be used to pharmaceutically induce slow waves for use as described herein.

All known states of anesthesia-induced unconsciousness can be characterized by the appearance of electroencephalogram (EEG) slow waves, which are high amplitude oscillations in the 0.5-4 Hz frequency range. For example, the slow-delta waves can be between about 0.5 Hz and about 4 Hz. The phased lock stimulation can also occur in this frequency range. The phased-locked neurostimulation would necessarily be between 250 ms and 2 seconds. As an example, an acoustic stimulation can be about 50 ms duration, with a 5 ms rising and falling time. This can be lengthened or shortened depending on the neurostimulation or pharmaceuticals used and can also be subject-dependent. The phase-locked neurostimulation can be performed before, during, or after a subject is administered a slow-delta wave enhancing/inducing agent (i.e., anesthesia, sedation).

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to pharmacological anesthetics, sedatives, muscle relaxants, analgesics, electroencephalography (EEG) electrodes, or neurostimulation electrodes. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, or sterile saline each of which has been packaged under a neutral non-reacting gas, such as nitrogen. Ampules may consist of any suitable material, such as glass, organic polymers, such as polycarbonate, polystyrene, ceramic, metal, or any other material typically employed to hold reagents. Other examples of suitable containers include bottles that may be fabricated from similar substances as ampules and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium or video. Detailed instructions may not be physically associated with the kit; instead, a user may be directed to an internet web site specified by the manufacturer or distributor of the kit.

A control subject as described herein can be a healthy subject not receiving anesthesia or not receiving treatment with the disclosed system or method.

The methods and algorithms of the invention may be enclosed in a controller or processor. Furthermore, methods and algorithms of the present invention, can be embodied as a computer implemented method or methods for performing such computer-implemented method or methods, and can also be embodied in the form of a tangible or non-transitory computer readable storage medium containing a computer program or other machine-readable instructions (herein "computer program"), wherein when the computer program is loaded into a computer or other processor (herein "computer") and/or is executed by the computer, the computer becomes an apparatus for practicing the method or methods. Storage media for containing such computer program include, for example, floppy disks and diskettes, compact disk (CD)-ROMs (whether or not writeable), DVD digital disks, RAM and ROM memories, computer hard drives and back-up drives, external hard drives, "thumb" drives, and any other storage medium readable by a computer. The method or methods can also be embodied in the form of a computer program, for example, whether stored in a storage medium or transmitted over a transmission medium such as electrical conductors, fiber optics or other light conductors, or by electromagnetic radiation, wherein when the computer program is loaded into a computer and/or is executed by the computer, the computer becomes an apparatus for practicing the method or methods. The method or methods may be implemented on a general purpose microprocessor or on a digital processor specifically configured to practice the process or processes. When a general-purpose microprocessor is employed, the computer program code configures the circuitry of the microprocessor to create specific logic circuit arrangements. Storage medium readable by a computer includes medium being readable by a computer per se or by another machine that reads the computer instructions for providing those instructions to a computer for controlling its operation. Such machines may include, for example, machines for reading the storage media mentioned above.

Compositions and methods described herein utilizing molecular biology protocols can be according to a variety of standard techniques known to the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Phase-Locked Anesthetic Neurostimulation

This example describes a novel method of enhancing pharmacologically-induced slow waves using multimodal phase-locked neurostimulation, which can increase control of an anesthetic state and modulate and decrease drug requirements for maintaining unconsciousness or anesthesia.

Abstract

General anesthesia is a drug-induced reversible state consisting of antinociception, unconsciousness, amnesia, and immobility with maintenance of physiological stability. All known states of anesthesia-induced unconsciousness can be characterized by the appearance of electroencephalogram (EEG) slow waves, which are high amplitude oscillations in the 0.5-4 Hz frequency range. Increasing the amplitude of slow waves correlates with deepening the level of unconsciousness. It is believed that all anesthetics can produce slow wave oscillations. The practice of multimodal general anesthesia has shown that anesthesia-induced unconscious and anesthesia-induced antinociception can be achieved by using multiple agents that act at different sites (receptors and circuits) in the pain and arousal pathways. Anesthetic states achieved by using multimodal combinations results in a reduced cumulative drug load, particularly for the hypnotic agents used to maintain unconsciousness. Here, we present a novel method of enhancing pharmacologically-induced slow waves using phase-locked neurostimulation. Neurostimulation modalities can include acoustic, electrical, magnetic, ultrasound, or visual stimulation. Enhancing slow waves in this way can decrease the probability of a state transition from an unconscious state to a conscious state, allowing anesthesiologists to maintain patient unconsciousness with lower hypnotic doses. Phase-locked neurostimulation can also increase the time-resolution of anesthetic state modulation and translate to faster emergence from unconsciousness. By decreasing cumulative drug loads, increasing the time-resolution of interventions, and accelerating recovery, phase-locked anesthetic neurostimulation can translate to improved patient outcomes in the perioperative and critical care settings.

Introduction

General anesthesia is a drug-induced reversible state of antinociception, unconsciousness, amnesia, and/or immobility with maintenance of physiological stability.[1] It is currently understood that anesthetic-induced altered states of arousal result from induction and maintenance of oscillations that disrupt communication among different brain regions.[2] The nature of the oscillations depend critically on the receptors that the anesthetics target and the neural circuitry connecting the brain regions where these targets lie. Alternatively stated, the oscillations depend on the drug class to which the anesthetic belongs. The characteristics of the oscillation also change systematically with patient age and pathologic state of the brain. Multimodal general anesthesia is based on the premise that anesthetic agents with complementary neural mechanisms can be used synergistically to create anesthetic states.[3] This observation suggests that anesthetic states can be designed "bottom-up" according to neuroscientific principles and maintained with a reduced cumulative drug load, titrated to clinical and electrophysiological endpoints. Thus far, multimodal anesthesia has largely relied on pharmacological agents to induce and maintain anesthetic states. Here, this framework is expanded to include phase-locked anesthetic neurostimulation (PLAN), a set of tools designed to maintain anesthetic states by combining pharmacologic and non-pharmacologic methods.

Slow Wave Oscillations

The differences in effects on the brain of anesthetics from different drug classes are readily visible in the electroencephalogram (EEG).[2] All anesthetics produce slow-delta wave oscillations (henceforth referred to as slow waves). Slow waves are large amplitude oscillations in the 0.5-4 Hz frequency range and can also be observed in non-rapid eye movement (NREM) sleep and states of coma.[1,4] Slow wave activity (SWA), defined as the EEG power between 0.5-4 Hz, is commonly used to quantify the extent to which these oscillations dominate brain dynamics at any given moment.

In a series of pioneering experiments in the 1930's, Frederic Bremer induced a state of persistent slow waves in cats by transecting the brainstem above the nucleus of the third cranial nerve, effectively isolating the telencephalon from the rest of the neuraxis ("cerveau isolé").[5] Transection of the brainstem below the medulla ("encephale isolé") did not induce slow waves or impair sleep-wake cycles, suggesting that ascending inputs from brainstem nuclei are critical to maintain arousal of a cerebrum that otherwise defaults to a slow oscillatory mode. We term this phenomenon Bremer's principle.

TABLE 1

| Ascending Activating System. | |
|---|---|
| Nucleus | Neurotransmitter |
| Locus coeruleus | Norepinephrine |
| Dorsal raphe nucleus | Serotonin |
| Ventral periaqueductal gray/ Ventral tegmental area | Dopamine |
| Tuberomammillary nucleus | Histamine |
| Lateral hypothalamus | Orexin |
| Lateral dorsal tegmental nucleus/ Pedunculopontine tegmental nucleus | Acetylcholine |
| Parabrachial nucleus | Glutamate |

Subsequent investigations have described in detail the nuclei that comprise this ascending activating system (TABLE 1).[6] The relationship between severing brainstem arousal projections to the thalamus and cortex and the production of slow oscillations helps us understand why anesthetics produce these dynamics. This is because the drugs target receptors in the brainstem and thereby block components of the major arousal pathways to the cortex and thalamus. Each anesthetic is therefore producing a version of Bremer's "cerveau isolé". It is now appreciated that inhibition of the ascending activating system by GABAergic and galanergic projections from the preoptic area of the hypothalamus have been linked to the production of non-REM sleep and its associated slow wave oscillations. At the cellular level, the slow oscillations reflect the synchronized oscillations of large ensembles of cortical neurons between depolarized (UP) states and hyperpolarized (DOWN) states.[7,8] When GABAergic anesthetics, such as propofol, the inhaled ethers, and the barbiturates, induce cortical neural circuits to oscillate at this rhythm, neuronal spiking becomes highly phase-limited, providing a putative cellular-level mechanism for anesthetic-induced unconsciousness.[9]

Figure 2:
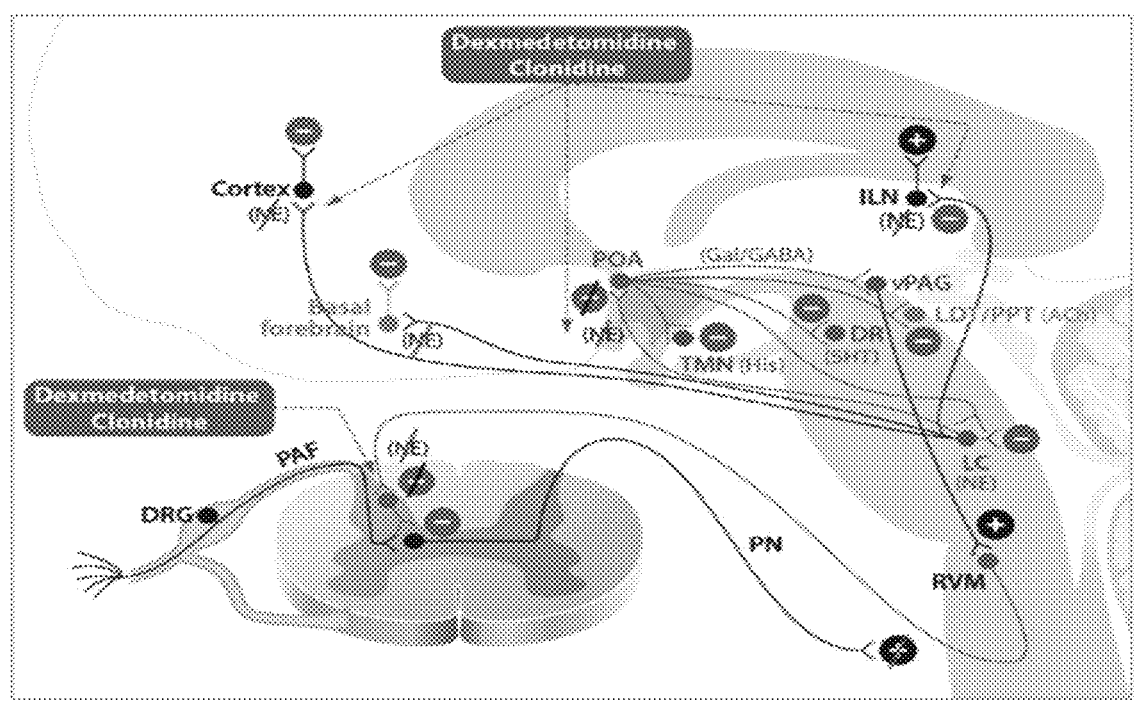
FIG. 2. Neural mechanisms of dexmedetomidine. Decreasing ascending noradrenergic tone from the locus coeruleus disinhibits the preoptic area of the hypothalamus, which then diffusely inhibits the ascending activating system and induces slow waves.

As mentioned above, the mechanisms through which anesthetics induce and maintain slow oscillations vary considerably.[3] For example, propofol and sevoflurane directly enhance inhibitory GABAergic activity of inhibitory interneurons in the cortex and thalamus, as well as at inhibitory GABAergic projections from the preoptic area of the hypothalamus onto the arousal centers in the brainstem (FIG. 1). In contrast, dexmedetomidine inhibits norepinephrine release from the locus coeruleus, dampening ascending noradrenergic tone and disinhibiting the preoptic area which further suppresses brainstem arousal centers (FIG. 2). NMDA antagonists such as ketamine and nitrous oxide inhibit glutamatergic projections from the parabrachial nucleus and medial pontine reticular formation in the brainstem to the thalamus and to the basal forebrain. Considering that the ascending activating system is composed of multiple nuclei and neurotransmitter systems, slow waves can be induced synergistically by targeting multiple pathways.

Slow waves have been extensively studied during both sleep and anesthesia. For example, SWA decreases progressively during subsequent periods of N3 sleep, reflective of dissipating sleep pressure, restoration of homeostasis, and lightening planes of sleep.[10] From an anesthetic perspective, SWA has been shown to correlate with depth of anesthesia and arousal.[11-13] There also appears to be an upper limit of how many neurons can be pharmacologically recruited to oscillate at these rhythms, termed SWA saturation.[12] In summary, slow waves are a common feature of many anesthetic states produced by different mechanisms, and represent a primary mechanism by which certain anesthetics maintain unconsciousness. Therefore, we focus our discussion of PLAN on the enhancement of slow waves.

Neurostimulation During Sleep and Anesthesia

The non-pharmacological enhancement of general anesthesia dates back to the early 20$^{th}$ century and focuses primarily on the use of electrical currents to induce and/or maintain unconsciousness.[14] The field of human electroanesthesia has been limited by serious side-effects associated with the electrical currents required to maintain unconsciousness, notably seizures, arrhythmias, laryngospasm, and thermal burns. In the 1960-70's, the French electrophysiologist Aimé Limoge developed a novel transcutaneous cranial electrical stimulation paradigm ("Limoge currents") allowing anesthesiologists to maintain pharmacologically-induced anesthetic states with lower drug doses, and minimal side-effects.[15] Following the pharmacological induction of general anesthesia, electrical current was delivered to the patient through three silver cutaneous electrodes: one positioned between the eyebrows and one behind each mastoid process. The electrical stimulus was produced by a high-frequency (167 kHz) generator, and the wave form was a complex non-sinusoidal, bi-phasic, non-square pattern consisting of 3 ms "on" followed by 10 ms "off". Although the peak-to-peak intensity ranged between 250-300 mA, the average pulse intensity was zero as a result of the waveform being composed of a short, high intensity positive pulse followed by a long, low intensity negative pulse. Limoge currents have reportedly been used to supplement pharmacological anesthetics tens of thousands of times in Europe and Asia.[16] However, most of these reports are anecdotal. A series of more rigorous investigations were published in the 1980-90's, describing the hypnotic and analgesic effects of Limoge currents, which were reported to decrease pharmacological requirements by 30-40%.[17-21] Multiple patents have been filed in the wake of these investigations,[15,22,23] but these techniques have not been incorporated into clinical practice in North America. It is important to note that none of the existing electroanesthesia methods use phase-locked stimulation.

The advent of phase-locked neurostimulation arose in the 21$^{st}$ century, with advances in processing power and signal processing methods. Building on reports that slow waves can be entrained during non-REM sleep using various neurostimulation methods (e.g., electrical, magnetic, acoustic),[24-26] Ngo and colleagues demonstrated the benefits of phase-locking stimulation to slow wave peaks.[27] Acoustic stimuli (pink noise) delivered during the "DOWN" state of slow waves (i.e., trough) disrupted slow oscillations. In contrast, acoustic stimuli delivered during the "UP" states (i.e., peak) enhanced the slow oscillations (i.e., increased their spectral power), consistent with the cellular physiology described earlier whereby cortical neurons are depolarized during slow wave peaks and hyperpolarized during slow wave troughs.[7,9] Subsequent studies have shown that enhancing sleep slow waves in this way carries the benefits of improved memory consolidation, heart rate dynamics, endocrine, and immune function.[28-32] These discoveries have led to the development and licensing of multiple algorithms designed to phase-lock neurostimulation to slow waves during ambulatory sleep.[33-38] As of yet, these methods have not been applied to enhance anesthetic-induced slow waves.

Phase-Locked Neurostimulation During General Anesthesia

In summary, described here is how complementary neural mechanisms can be combined to synergistically induce slow waves and maintain anesthetic states, that transcranial electrical stimulation can reduce hypnotic and analgesic requirements, and that phase-locking neurostimulation to the peaks of slow waves during sleep is a highly effective method of enhancing their spectral power and physiological effects. Next, we combine these lines of investigations to describe a novel method for the toolbox of multimodal anesthesia: phase-locked anesthetic neurostimulators (PLANs). Stated briefly, PLANs maintain anesthetic states by enhancing pharmacologically-induced slow waves using multimodal phase-locked neurostimulation. Enhancing slow waves in this way decreases the probability of a transition from an unconscious state to a conscious state.

Multimodal general anesthesia designs anesthetic states "bottom-up" by combining complementary neural mechanisms. The common EEG endpoint of these mechanisms is the generation of slow waves via Bremer's principle, and continuous infusions and/or inhalation of anesthetic agents to maintain these oscillatory states. Similarly, acoustic, electrical, and magnetic stimulation can be used to maintain slow waves through complementary neural mechanisms: ascending non-lemniscal auditory stimulation pathways, and modulation of cortical electrical and magnetic fields, respectively.[24,25,39] Therefore, it stands to reason that these stimulation modalities can be integrated into the framework of multimodal anesthesia to maintain anesthetic-induced unconsciousness and further reduce or eliminate pharmacological requirements. In fact, Limoge currents have already been used to this effect, albeit without the benefit of phase-locking or the combination of multiple modalities. A sample of pharmaco-stimulation combinations is presented in TABLE 2. One drug example is provided for each anesthetic target (e.g., propofol for GABA), and a single target combination is presented (i.e., GABA+Alpha2). In practice, any drug (anesthetic agent) with activity at an anesthetic target could replace the examples presented in TABLE 2 (e.g., replacing propofol with sevoflurane), and any combination of anesthetic targets and neurostimulation modalities can be used to maintain anesthetic states. Furthermore, it is possible that a single drug such as dexmedetomidine may not induce unconsciousness by itself, but that an unconscious state is achieved by enhancing slow waves using phase-locked neurostimulation.

TABLE 2. Examples of how anesthetic agents and stimulation modalities can be combined to produce unconsciousness. For simplicity, only two pharmacological mechanisms and two stimulation modalities are included.

| Examples of Multimodal Anesthesia-Induced Unconsciousness | | | |
| --- | --- | --- | --- |
| Anesthetic Target | Acoustic Stimulation | Electrical Stimulation | Acoustic + Electrical Stimulation |
| Enhanced GABAergic activity | Propofol + sound | Propofol + electricity | Propofol + sound + electricity |
| Alpha2 agonism | Dexmedetomidine + sound | Dexmedetomidine + electricity | Dexmedetomidine + sound + electricity |
| NMDA antagonism | Ketamine + sound | Ketamine + electricity | Ketamine + sound + electricity |
| Opioid agonism | Remifentanil + sound | Remifentanil + electricity | Remifentanil + sound + electricity |
| Enhanced GABAergic activity + Alpha2 agonism | Propofol + dexmedetomidine + sound | Propofol + dexmedetomidine + electricity | Propofol + dexmedetomidine + sound + electricity |

Phase-locked anesthetic neurostimulators are similar to brain-computer interfaces in that they are composed of three basic components: EEG sensors and amplifiers (i.e., input), a phase-locking algorithm computed on a central processing unit (i.e., computer), and neurostimulation hardware (i.e., output). EEG sensors and amplifiers are commercially available for research and clinical use. The optimal EEG montage used in a PLAN will depend on the specific anesthetic agents and stimulation modalities being combined. Ideally, frontal, temporal, parietal and occipital leads should be included to account for variances in slow wave topography across patients and anesthetics. Multimodal stimulation can be phase-locked to one or multiple electrodes. As stated previously, multiple phase-locking algorithms have been developed to deliver stimuli synchronized with slow wave peaks during natural sleep.[33-38] Although they share overlapping neural circuits, sleep slow waves and the wide range of anesthetic slow waves are not identical.[1,40-43]

Nevertheless, their EEG properties are similar enough that these algorithms only require minimal modifications to effectively track and stimulate pharmacologically-induced slow waves. Whereas sleep slow wave enhancement devices are designed to autonomously classify sleep stages and activate stimulation algorithms during unattended N3 sleep, PLANs are designed to interface directly with an attending anesthesiologist who can adjust their settings and use them according to their training and assessment of the clinical scenario. Adjustable settings include topography of phase-locking, target frequency bandwidth, stimulation phase, stimulation modalities, and/or stimulation intensities. The interface also feeds back key EEG data to the anesthesiologist, including raw EEG, power spectral density and SWA. The neurostimulation hardware used in PLANs is also already available: noise-isolating earphones, transcranial electrical stimulation, and transcranial magnetic stimulation. The implementation of these technologies within PLANs requires that they be EEG-compatible and that they not disrupt slow wave detection. Acoustic stimulation will be the easiest to implement, followed by electrical and then magnetic stimulation.

In summary, the individual technologies for PLANs already exist. The innovation of this technique is the synthesis of existing neurostimulation techniques with EEG phase-locking algorithms to slow waves in the framework of multimodal anesthesia.

Proposed Phase-Lock Anesthetic Protocol

An important consideration in multimodal anesthesia is the titration of different modalities. Analgesia is traditionally assessed using a patient's vital signs (raw or as a processed index), reflecting sympathetic responses to noxious stimulation. Unconsciousness, on the other hand, can be assessed with the neurological examination and EEG.[2,3,44] Specifically, slow wave activity induced by GABAergic anesthetics, is a strong indication of unconsciousness.[11,12,45,46] Therefore, disclosed here is a protocol for integrating PLANs in multimodal anesthesia:

1. Assess preoperatively any absolute or relative contraindications to neurostimulation modalities (e.g., deep brain stimulator, seizure disorder, pacemaker, hearing impairment).
2. Apply the EEG in addition to standard perioperative patient monitors (i.e., electrocardiogram, blood pressure, peripheral capillary oxygen saturation, temperature, capnography).
3. Induce pharmacologically unconsciousness using complementary neural mechanisms.
4. Apply multimodal phase-locked neurostimulation of EEG slow waves. Each modality can be added individually, and settings optimized for enhancing slow wave activity.
5. Titrate down pharmacologic agents guided by clinical signs and EEG. Maintaining multimodal pharmacology should be prioritized over eliminating any specific agent.
6. Discontinue anesthetic administration and neurostimulation at the end of the procedure, once it is appropriate for the patient to recover consciousness.
7. Assess post-operatively the subjective experience of the patient recalled during the procedure.

Potential Benefits

The drug-sparing effects of this method are expected to vary according to a host of factors, including the specific combination of pharmacological and neurostimulation modalities, the drug titration sequence (e.g., decreasing the propofol infusion rate before or after decreasing the concentration of inhaled nitrous oxide), procedure-specific factors (e.g., colonoscopy versus liver transplant), and the patient's personal neurophysiology (e.g., age, cognitive reserve, illicit drug dependence, sleep deprivation, circadian rhythm phase). Considering that Limoge currents were reported to decrease anesthetic drug requirements by 30-40%, multimodal phase-locked neurostimulation may obviate the need for any pharmacological agent to maintain anesthetic states in some instances.

The benefits of reducing the cumulative anesthetic drug-load that patients receive in the perioperative period are multi-faceted. As suggested by the use of Limoge currents, emergence from anesthetic states can be accelerated because patients have less anesthetic agents to clear from their compartments. Furthermore, the speed at which neurostimulation modalities can be adjusted far exceeds the speed of even the "fastest" anesthetic drugs such as propofol. Increasing the time-resolution of anesthetic modalities (i.e., fast-on, fast-off), can allow anesthesiologists to fine-tune anesthetic states with greater precision throughout the perioperative period. From a cognitive standpoint, PLANs may decrease the incidence of post-operative cognitive disorders such as delirium and delayed cognitive recovery.[47] There is also ongoing concern about the effects of anesthetics on neurodevelopment in pediatric patients.[48] Most anesthetic agents are also associated with dose-dependent systemic side-effects such as peripheral vasodilation, hypothermia, decreased cardiac output, and respiratory depression. Patients with poor physiological reserve can benefit from a lower dose of these agents. These benefits could also be realized in the ICU, where critically ill patients often require sedation to facilitate mechanical ventilation and execution of bedside procedures. Infusions of dexmedetomidine and propofol are often administered for multiple days in the ICU. The financial implications of PLANs are difficult to forecast but would likely be proportional to both their drug-sparing effects and their effects on improving perioperative outcomes (e.g., post-operative complications, ICU and hospital length of stay). The drug-sparing effects would be of particular benefit in the global health and space medicine settings, where the transportation of large quantities of perishable anesthetic agents is a limiting factor.

A Hypothetical Case

A 45-year-old woman with a newly diagnosed renal mass presents for an elective right nephrectomy. She has no other past medical or surgical history. Standard ASA monitors and an EEG cap with eight electrodes connected to an electroacoustic PLAN are applied. General anesthesia is induced by titrating infusions of propofol, dexmedetomidine, and remifentanil. Loss of behavioral responsiveness is associated with the appearance of EEG slow waves (SWA of 30%) and alpha oscillations. Neuromuscular blockade with rocuronium subsequently facilitates endotracheal intubation. A low dose infusion of phenylephrine is started to maintain a mean arterial blood pressure greater than 65 mmHg. Phase-locked acoustic stimulation is started and SWA increased to 40%. The propofol and dexmedetomidine infusion rates are decreased and SWA decreases to 35%. The phenylephrine infusion can then be turned off. Phase-locked transcranial electrical stimulation with bilateral frontoparietal electrodes is started and SWA rises to 50%. The dexmedetomidine infusion is turned off and SWA decreases to 40%. Near the end of skin closure, the propofol infusion is turned off and SWA decreases to 25%. After skin closure, the remifentanil infusion is turned off and SWA decreases to 22%. After the patient resumes spontaneous breathing, phase-locked acoustic and transcranial electrical stimulation are turned off and SWA decreases to 2%. The patient quickly regains behavioral responsiveness, is successfully extubated and transferred to the post-anesthesia care unit. When questioned about subjective experiences during surgery, the patient denies any dreams or other recall experiences. After one night of observation in the hospital, she is discharged home and scheduled for post-operative follow up.

REFERENCES

1. Brown E N, Lydic R, Schiff N D. General anesthesia, sleep, and coma. *N Engl J Med.* 2010; 363(27):2638-2650.
2. Purdon P L, Sampson A, Pavone K J, Brown E N. Clinical Electroencephalography for Anesthesiologists: Part I: Background and Basic Signatures. *Anesthesiology.* 2015, 123(4):937-960.
3. Brown E N, Pavone K J, Naranjo M. Multimodal General Anesthesia: Theory and Practice. *Anesth Analg.* 2018; 127(5):1246-1258.
4. Tononi G, Cirelli C. Sleep and the price of plasticity: from synaptic and cellular homeostasis to memory consolidation and integration. *Neuron.* 2014,81(1):12-34.
5. Kerkhofs M, Lavie P. Frederic Bremer 1892-1982: a pioneer in sleep research. *Sleep Med Rev.* 2000; 4(5):505-514.
6. Lee S H, Dan Y. Neuromodulation of brain states. *Neuron.* 2012; 76(1):209-222.
7. Steriade M, Timofeev I, Grenier F. Natural waking and sleep states: a view from inside neocortical neurons. *J Neurophysiol.* 2001,85(5):1969-1985.
8. Vyazovskiy V V, Olcese U, Lazimy Y M, et al. Cortical firing and sleep homeostasis. *Neuron.* 2009; 63(6):865-878.
9. Lewis L D, Weiner V S, Mukamel E A, et al. Rapid fragmentation of neuronal networks at the onset of propofol-induced unconsciousness. *Proc Natl Acad Sci USA.* 2012; 109(49):E3377-3386.
10. Prerau M J, Brown R E, Bianchi M T, Ellenbogen J M, Purdon P L. Sleep Neurophysiological Dynamics Through the Lens of Multitaper Spectral Analysis. *Physiology (Bethesda).* 2017,32(1):60-92.
11. Scheinin A, Kallionpaa R E, Li D, et al. Differentiating Drug-related and State-related Effects of Dexmedetomidine and Propofol on the Electroencephalogram. *Anesthesiology.* 2018,129(1):22-36.
12. Ni Mhuircheartaigh R, Warnaby C, Rogers R, Jbabdi S, Tracey I. Slow-wave activity saturation and thalamocortical isolation during propofol anesthesia in humans. *Sci Transl Med.* 2013,5(208):208ra148.
13. Sleigh J W, Vacas S, Flexman A M, Talke P O. Electroencephalographic Arousal Patterns Under Dexmedetomidine Sedation. *Anesth Analg.* 2018,127(4):951-959.
14. Smith R H, Tatsuno J, Zouhar R L. Electroanesthesia: a review-1966. *Anesth Analg.* 1967,46(1):109-125.
15. Limoge A, Inventor. An electrostimulation by currents of high frequency modules with currents of low frequency. US patent FR2684872611991.
16. Goldman B. Can Aime Limoge sell electroanesthesia to North America? *Can Med Assoc J.* 1984; 130(9):1191-1193, 1196-1197, 1200.
17. Stanley T H, Cazalaa J A, Atinault A, Coeytaux R, Limoge A, Louville Y. Transcutaneous cranial electrical stimulation decreases narcotic requirements during neurolept anesthesia and operation in man. *Anesth Analg.* 1982,61(10):863-866.

18. Stanley T H, Cazalaa J A, Limoge A, Louville Y. Transcutaneous cranial electrical stimulation increases the potency of nitrous oxide in humans. *Anesthesiology.* 1982,57(4):293-297.
19. Naveau S, Barritault L, Zourabichvili O, et al. [Analgesic effect of transcutaneous cranial electrostimulation in patients treated by Nd:YAG laser for cancer of the rectum. A double-blind randomized trial]. *Gastroenterol Clin Biol.* 1992,16(1):8-11.
20. Mantz J, Azerad J, Limoge A, Desmonts J M. Transcranial electrical stimulation with Limoge's currents decreases halothane requirements in rats. Evidence for the involvement of endogenous opioids. *Anesthesiology.* 1992,76(2):253-260.
21. Mignon A, Laudenbach V, Guischard F, Limoge A, Desmonts J M, Mantz J. Transcutaneous cranial electrical stimulation (Limoge's currents) decreases early buprenorphine analgesic requirements after abdominal surgery. *Anesth Analg.* 1996; 83(4):771-775.
22. Bell J O, Inventor. Passive monitoring of bioelectrical signals and active electrical anesthesia stimulation. US patent US7986996622005.
23. Vladimir Nekhendzy M M, Inventor. Eliciting analgesia by transcranial electrical stimulation. US patent US6567702612000.
24. Marshall L, Helgadottir H, Molle M, Born J. Boosting slow oscillations during sleep potentiates memory. *Nature.* 2006,444(7119):610-613.
25. Massimini M, Ferrarelli F, Esser S K, et al. Triggering sleep slow waves by transcranial magnetic stimulation. *Proc Natl Acad Sci USA.* 2007; 104(20):8496-8501.
26. Ngo H V, Claussen J C, Born J, Molle M. Induction of slow oscillations by rhythmic acoustic stimulation. *J Sleep Res.* 2013; 22(1):22-31.
27. Ngo H V, Martinetz T, Born J, Molle M. Auditory closed-loop stimulation of the sleep slow oscillation enhances memory. Neuron. 2013,78(3):545-553.
28. Besedovsky L, Ngo H V, Dimitrov S, Gassenmaier C, Lehmann R, Born J. Auditory closed-loop stimulation of EEG slow oscillations strengthens sleep and signs of its immune-supportive function. *Nat Commun.* 2017,8(1):1984.
29. Papalambros N A, Santostasi G, Malkani R G, et al. Acoustic Enhancement of Sleep Slow Oscillations and Concomitant Memory Improvement in Older Adults. *Front Hum Neurosci.* 2017; 11:109.
30. Ong J L, Lo J C, Chee N I, et al. Effects of phase-locked acoustic stimulation during a nap on EEG spectra and declarative memory consolidation. *Sleep Med.* 2016; 20:88-97.
31. Leminen M M, Virkkala J, Saure E, et al. Enhanced Memory Consolidation Via Automatic Sound Stimulation During Non-REM Sleep. *Sleep.* 2017; 40(3).
32. Grimaldi D, Papalambros N A, Reid K J, et al. Strengthening sleep-autonomic interaction via acoustic enhancement of slow oscillations. *Sleep.* 2019.
33. Santostasi G, Malkani R, Riedner B, et al. Phase-locked loop for precisely timed acoustic stimulation during sleep. *J Neurosci Methods.* 2016; 259:101-114.
34. Garcia-Molina G, Tsoneva T, Jasko J, et al. Closed-loop system to enhance slow-wave activity. *J Neural Eng.* 2018,15(6):066018.
35. Debellemaniere E, Chambon S, Pinaud C, et al. Performance of an Ambulatory Dry-EEG Device for Auditory Closed-Loop Stimulation of Sleep Slow Oscillations in the Home Environment. *Front Hum Neurosci.* 2018; 12:88.
36. Nir Grossman D W, Edward Boyden Inventor. Methods and Apparatus for Neuromodulation. US patent US20170020447A12016.
37. Giovanni Santostasi P Z, Inventor. Phase-locked loop to enhance slow wave sleep. US patent US20170304587A12015.
38. Gary Nelson GMMB, Brady Alexander Riedner, Giulio Tononi, Juan Benzo Inventor. System and method for determining timing of sensory stimulation delivered to a subject during a sleep session. US patent U.S. Ser. No. 10/307,88622015.
39. Bellesi M, Riedner B A, Garcia-Molina G N, Cirelli C, Tononi G. Enhancement of sleep slow waves: underlying mechanisms and practical consequences. *Front Syst Neurosci.* 2014; 8:208.
40. Murphy M, Bruno M A, Riedner B A, et al. Propofol anesthesia and sleep: a high-density EEG study. *Sleep.* 2011,34(3):283-291A.
41. Akeju O, Kim S E, Vazquez R, et al. Spatiotemporal Dynamics of Dexmedetomidine-Induced Electroencephalogram Oscillations. *PLoS One.* 2016; 11(10):e0163431.
42. Guldenmund P, Vanhaudenhuyse A, Sanders R D, et al. Brain functional connectivity differentiates dexmedetomidine from propofol and natural sleep. *Br J Anaesth.* 2017; 119(4):674-684.
43. Chauvette S, Crochet S, Volgushev M, Timofeev I. Properties of slow oscillation during slow-wave sleep and anesthesia in cats. *J Neurosci.* 2011,31(42):14998-15008.
44. Reshef E R, Schiff N D, Brown E N. A Neurologic Examination for Anesthesiologists: Assessing Arousal Level during Induction, Maintenance, and Emergence. *Anesthesiology.* 2019,130(3):462-471.
45. Gaskell A L, Hight D F, Winders J, et al. Frontal alpha-delta EEG does not preclude volitional response during anaesthesia: prospective cohort study of the isolated forearm technique. *Br J Anaesth.* 2017,119(4):664-673.
46. Warnaby C E, Sleigh J W, Hight D, Jbabdi S, Tracey I. Investigation of Slow-wave Activity Saturation during Surgical Anesthesia Reveals a Signature of Neural Inertia in Humans. *Anesthesiology.* 2017; 127(4):645-657.
47. Evered L, Silbert B, Knopman D S, et al. Recommendations for the nomenclature of cognitive change associated with anaesthesia and surgery-2018. *Br J Anaesth.* 2018; 121(5):1005-1012.
48. Vutskits L, Davidson A. Update on developmental anesthesia neurotoxicity. *Curr Opin Anaesthesiol.* 2017; 30(3):337-342.

Example 2: Sleep Slow-Wave Stimulation Achieved with Acoustic Stimulation

This example describes how acoustic stimulation can be used to selectively enhance specific slow-delta frequency bands during sleep (see e.g., FIG. 3-FIG. 6).

Figure 3:
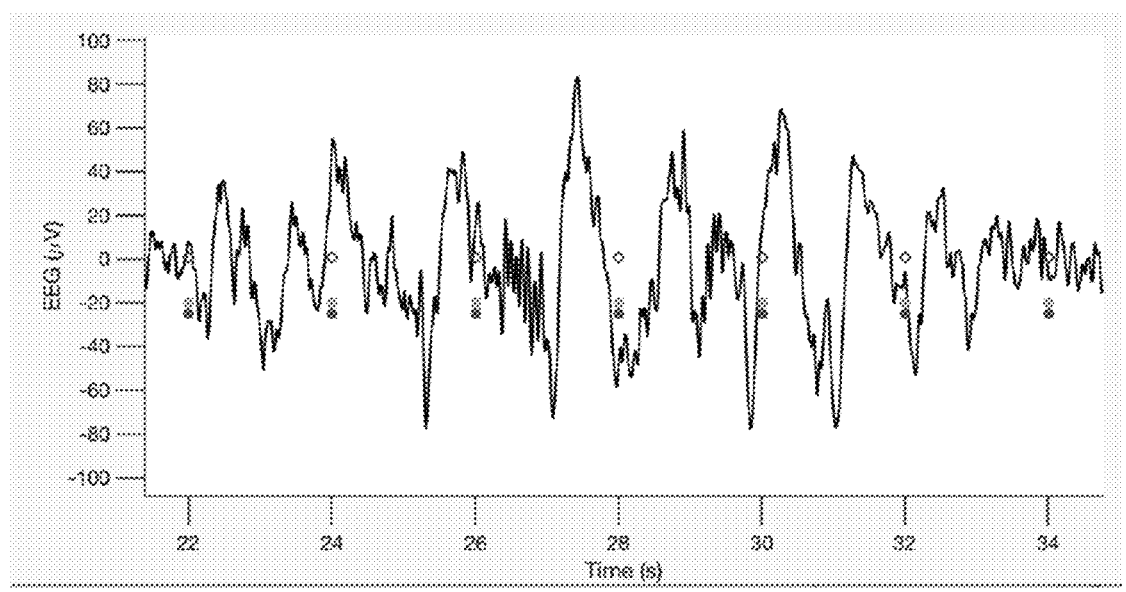
FIG. 3. Sample slow wave sleep (raw EEG).
Figure 4:
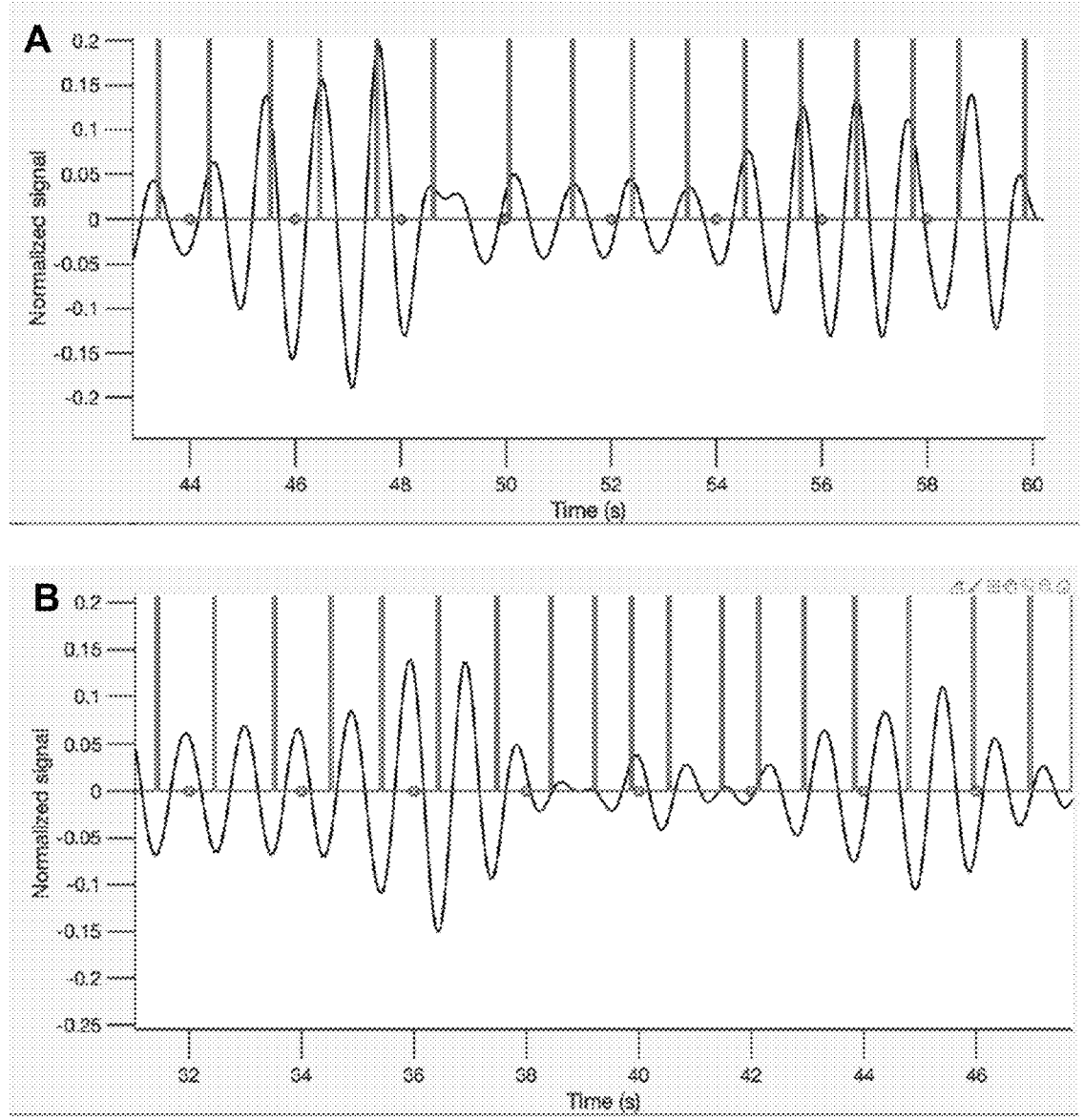
FIG. 4. (a) In-phase stimulation (peak-locked), 0.5 s refractory interval. (b) Anti-phase stimulation (trough-locked), 0.5 s refractory interval.

These data were created from data acquired during an overnight experiment using the device and a volunteer in a sleep lab. The purpose of this experiment was to verify that the device effectively phase-locks to EEG slow waves. FIG. 3 is a raw EEG waveform. FIG. 4A is a smoothed/modeled EEG waveform with phase-locked acoustic stimulation to slow wave peaks in red.

FIG. 4B shows a smoothed/modeled EEG waveform with phase-locked acoustic stimulation to slow wave troughs in red.

FIG. 5 are polar plots, showing the distribution of stimulation in relation to the computed EEG slow wave phase.

In-phase stimulation is aiming for zero degrees (peak) and antiphase stimulation is aiming for 180 degrees (trough). The resultant is a measure of the cumulative accuracy of the phase-locked stimulation (as visualized in the polar plots).

Figure 5A:
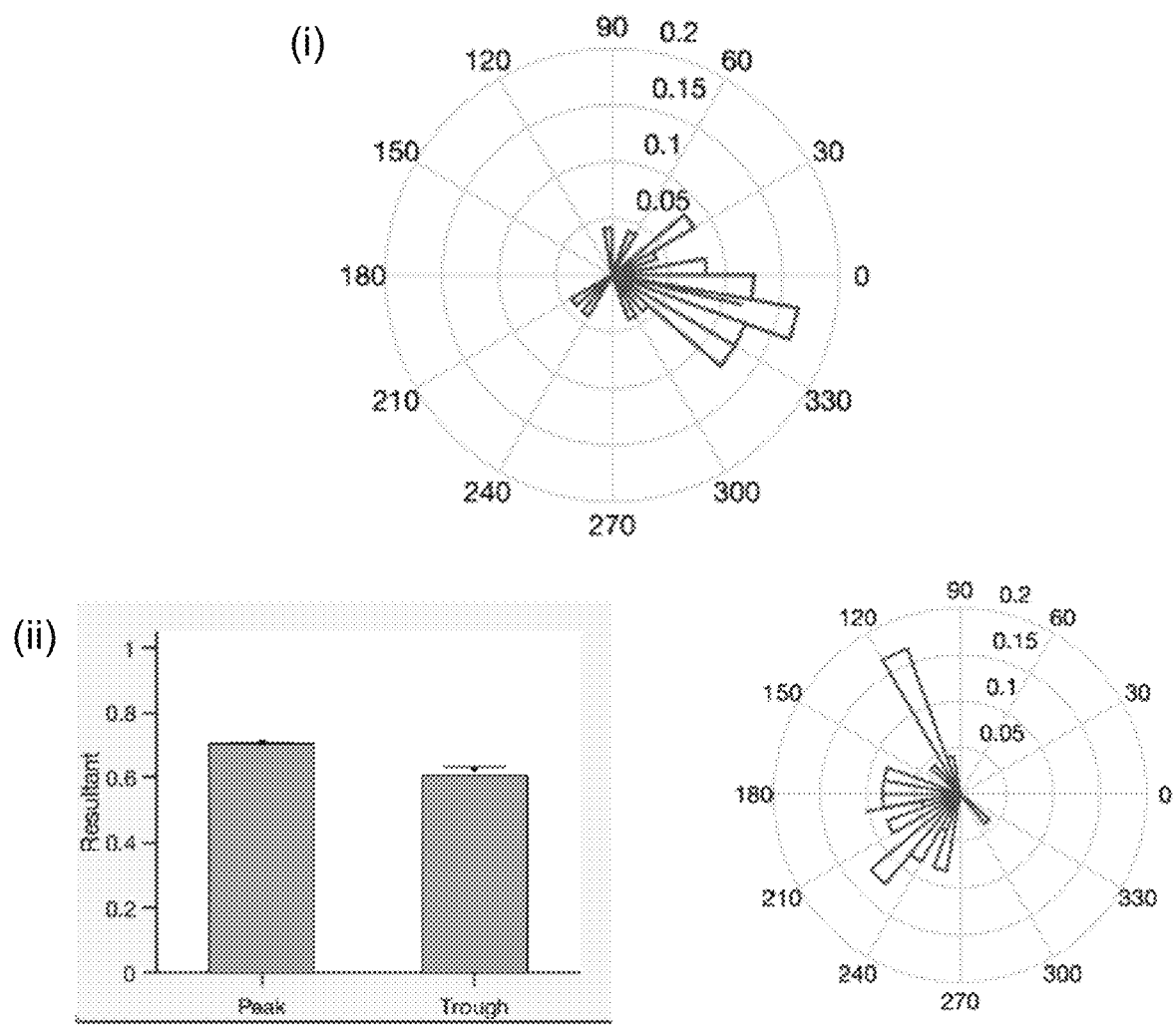
FIG. 5A-FIG. 5C. Polar plots.
Figure 5B:
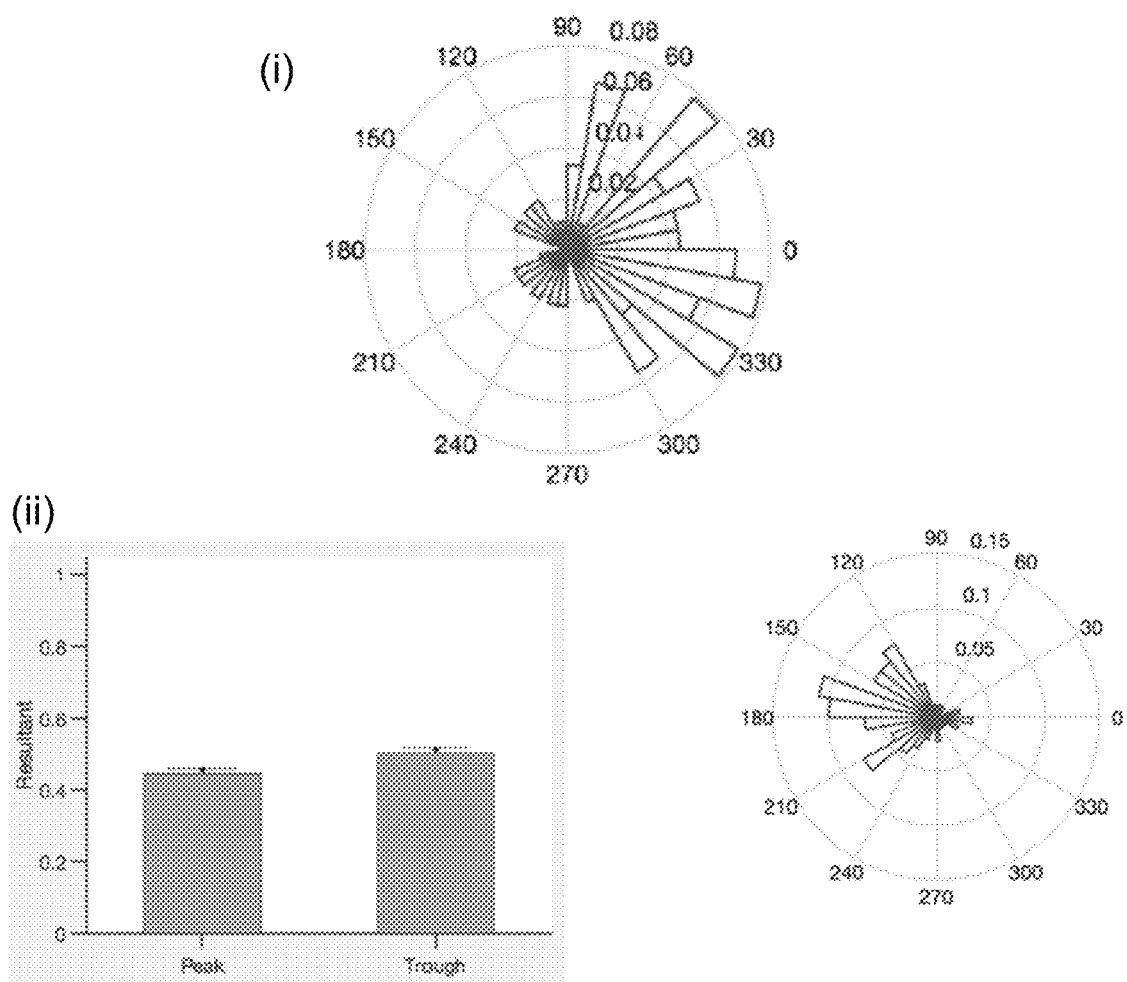
Figure 5C:
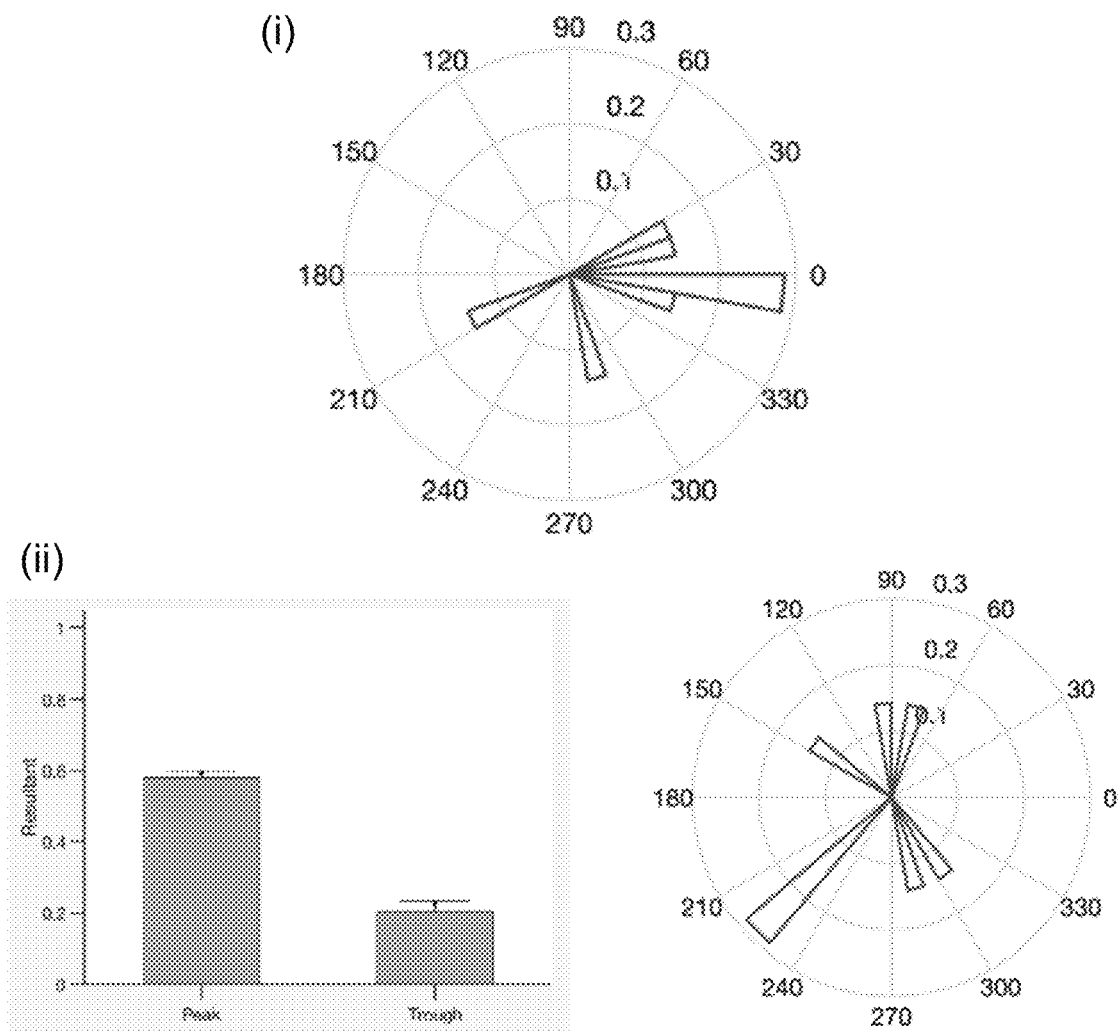

FIG. 5A-FIG. 5C shows results for different stimulation paradigms that were was explored. Here, it was decided to use the paradigm in FIG. 5A (as described in Example 4) because of the better accuracy (see resultants). FIG. 5A(i) is a polar plot with in-phase stimulation. FIG. 5A(ii) is resultant of phase-locking accuracy. FIG. 5A(iii) is a polar plot with anti-phase stimulation.

Figure 6:
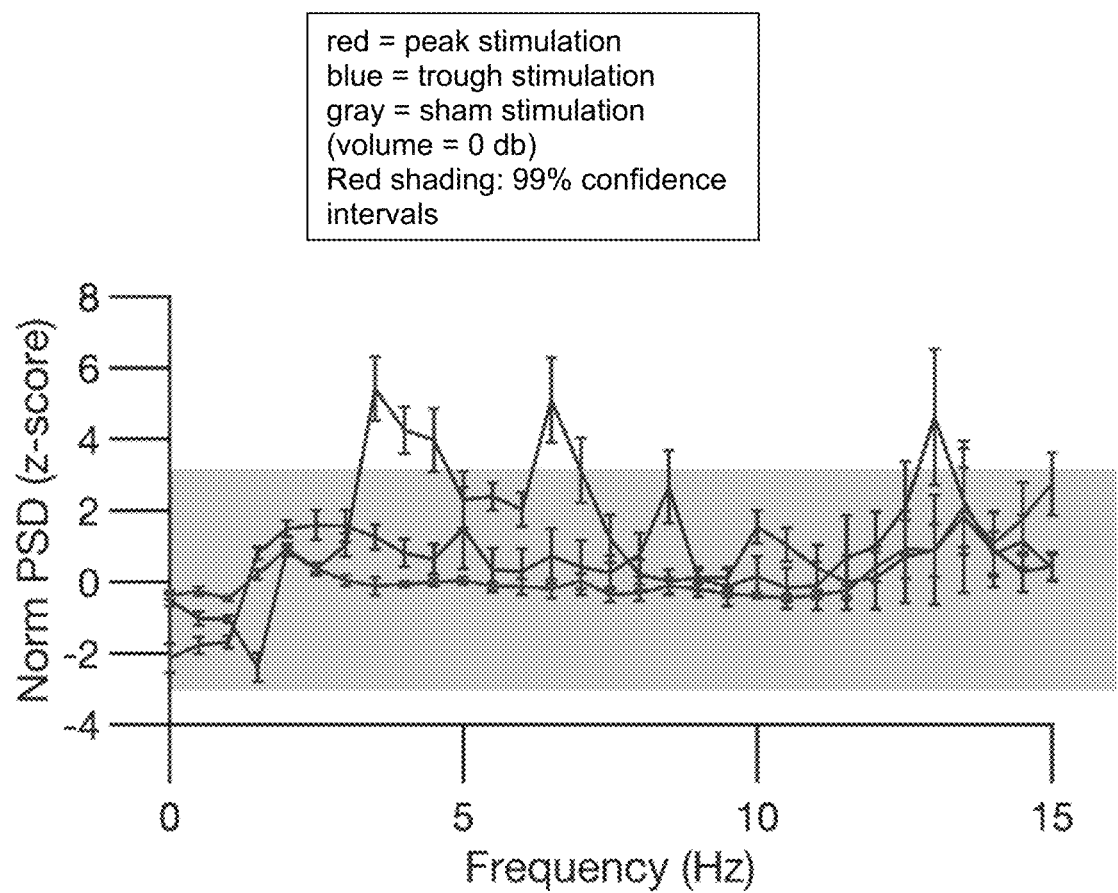
FIG. 6. Power Spectral Density Analysis. Stimulation specs: i. Targeted frequency: 1 Hz; ii. Refractory period: 0.5 seconds; iii. Baseline duration (per block): 10 seconds; iv. Stimulation duration (per block): 50 seconds; v. Number of blocks: 3 (peak, trough, sham). Analysis specs: i. Fast Fourier transform (2 second windows); ii. Power spectral density normalized to the baseline spectrum and then z-transformed, i.e., each color represents the deviation of EEG spectrum during stimulation (50 seconds), as compared to baseline (10 seconds), during a specific condition (see FIG. 6, legend).

FIG. 6 shows a frequency domain EEG analysis of the effects of phase-locked stimulation. Red: in-phase stimulation. Blue: anti-phase stimulation. Grey: sham. Y-axis is the normalized power spectral density given in z-scores (i.e., standard deviation differences from baseline). In-phase stimulation resulted in the enhancement of EEG power in delta and theta bands, as indicated by the peaks surpassing 3 z-scores.

Example 3: Closed Loop Acoustic Stimulation During Sedation with Dexmedetomidine (Class-D)

This example describes a study to evaluate whether dexmedetomidine-induced slow waves can be potentiated through in-phase closed-loop acoustic stimulation (CLAS).

| | Synopsis |
|---|---|
| Study Title | Closed Loop Acoustic Stimulation during Sedation with Dexmedetomidine (CLASS-D) |
| Objectives | Objective 1: Determine potentitation of dexmedetomidine-induced EEG slow waves through in-phase closed-loop acoustic stimulation (CLAS). |
| | Objective 2: Assess thresholds for responsiveness to electrical stimulation during dexmedetomidine sedation modulated by slow wave CLAS. |
| | Objective 3: Assess whether dexmedetomidine sedation with CLAS reduces metrics of slow wave need on the night of the intervention. |
| | Objective 4: Compare modeled brain localization of dexmedetomidine-induced EEG slow waves recorded in the presence and absence of in-phase CLAS. |
| Study Period | Planned enrollment duration: one year Planned study duration: two years |
| Sample Size | 14 volunteers |
| Study Design | Prospective within-subject study of dexmedetomidine sedation paired with CLAS conditions in repeated blocks. Intervention will consist of CLAS in-phase with EEG slow waves. Anti-phase stimulation will serve as an active control while sham stimulation will serve as a passive control. |
| Study Procedures | All participants will receive dexmedetomidine with sedation titrated step-wise to 2, 3, or 4 ng/ml until two endpoints are met: 1) loss of behavioral responsiveness to auditory command (squeezing a ball during inspiration) and 2) the appearance of EEG slow waves (0.5-4 Hz). Subjects will then have multiple 5-minute blocks: (1) Acoustic stimulation (65 dB) synchronized in-phase with the up-slope of EEG slow waves, (2) 65 dB acoustic stimulation synchronized with the down-slope of the EEG slow waves (anti-phase), and (3) sham stimulation (0 dB volume). Stepwise increasing electrical stimulation (20-50 milliamperes) will be delivered to compare response thresholds between conditions. Unattended home sleep studies will be conducted on the night preceding sedation and on the night following sedation to assess changes in slow wave homeostasis. A non-contrast brain MRI will be acquired for localizing EEG slow waves. |
| Inclusion and Exclusion Criteria | Inclusion: healthy volunteers, 18-40 years old, American Society of Anesthesiologists Physical Status 1-2. Exclusion: Diagnosed sleep disorders, habitually short sleepers, diagnosed psychiatric disorders, use of psychoactive medication, diagnosed hearing disorder, neck circumference >40 cm, Body Mass Index >30, acknowledged recreational drug or nicotine use, resting heart rate during slow wave sleep <40 beats per minute, pregnancy, or nursing. |
| Measurements | Primary: EEG slow wave activity (SWA); relative power in the 0.5-4 Hz band. Secondary: electromyography (EMG), Stanford Sleepiness Scale, Pittsburgh Sleep Quality Index, video recordings, brain MRI. |
| Statistical Methodology | SWA across conditions: general mixed-effects models Sleep homeostasis: paired t- or U-tests, depending on normality of measures. Thresholds of responsiveness to stimulation: logistic regression modeling. Comparing slow wave topology: Permutation/bootstrap analyses |

Study Protocol

Background and Significance

Sleep addresses important physiologic needs in humans and most living organisms. Although the neurological mechanisms of sleep are still debated, the electroencephalographic (EEG) correlates of sleep are well characterized.[1] Slow waves, the large amplitude, low frequency EEG oscillations that dominate non-rapid eye movement (NREM) sleep, have been shown to play critical roles in physiologic restoration, memory consolidation, and dissipating homeostatic sleep pressure.[2] At the cellular level, these slow oscillations correspond to the synchronous state switching of large ensembles of cortical neurons between depolarized "up" states and hyperpolarized "down" states (i.e., burst firing).[3] At the scalp level, slow wave activity (SWA) is EEG relative power in the 0.5-4 Hz frequency band. SWA is a known marker of sleep need and its dissipation is homeostatically regulated.[4]

Figure 7:
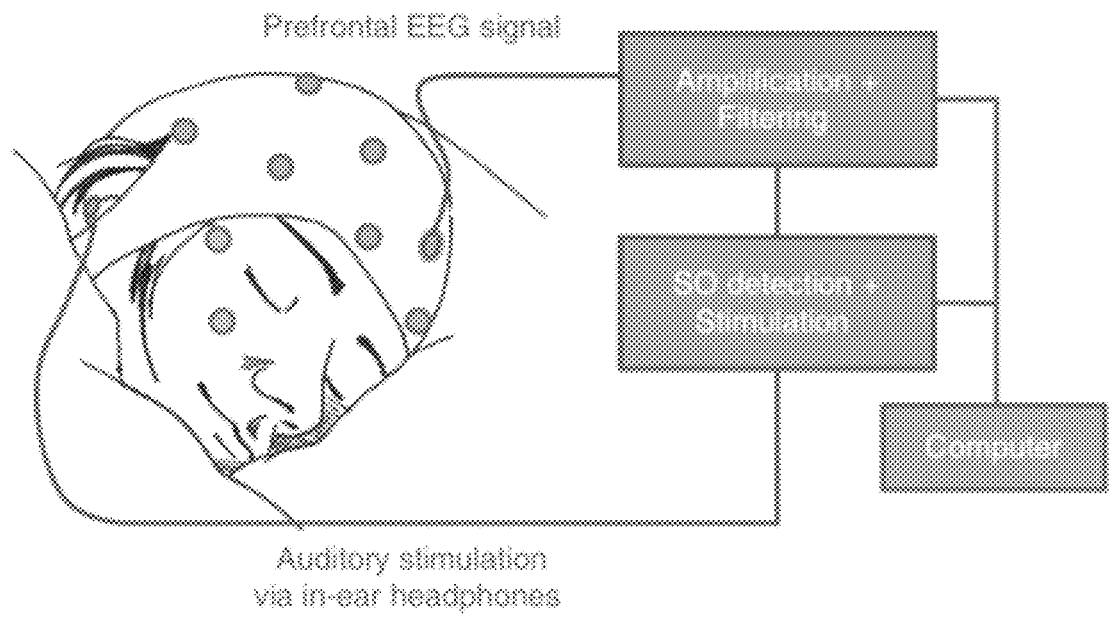
FIG. 7. Graphical depiction of closed loop acoustic stimulation. EEG signals are amplified and filtered before undergoing processing. Custom-made scripts detect slow oscillations and compute their oscillatory phase. In-phase acoustic stimuli are delivered during the up-slope of slow waves. Anti-phase acoustic stimuli are delivered during the down-slope of slow waves. Adapted from references 9 and 23.
Figure 13:
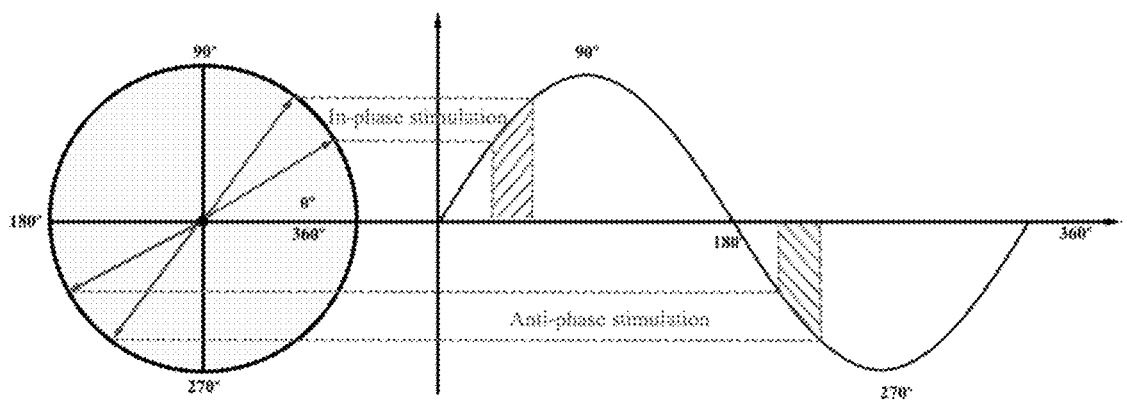
FIG. 13. Phase-locked Acoustic Stimulation. A circular plot can be used to visualize different phases of slow waves that are targeted using phase-locked acoustic stimulation. In-phase stimulation delivers pink noise during the upslope of slow waves, and anti-phase stimulation delivers pink noise during the downslope of slow waves. In practice, acoustic stimulation is phase-locked to a range of the slow wave's cycle, represented in red here.

Enhancing slow oscillations has recently emerged as a promising strategy to improve natural sleep and treat sleep disorders using electrical, magnetic and acoustic modalities.[5-7] The impact of these interventions on clinical outcomes is an active area of investigation. These findings have raised the possibility of accelerating the decay of sleep pressure, enhancing memory consolidation, and improving autonomic, neuroendocrine, and immune function.[8-12] Considering the substantial safety advantages of using sound, acoustic stimulation has recently emerged as the preferred method to enhance sleep slow oscillations in the ambulatory setting.[8,13] These depend on the realtime processing of EEG signal and precise delivery of auditory stimulation in relation to oscillations in the EEG (FIG. 7). Over the last decade, multiple algorithms have been developed to synchronize bursts of pink noise in-phase with the up-slope of 0.5-4 Hz slow wave oscillations (FIG. 13). Pink noise, also known as 1/f noise (denoting its power density), is random noise that has equal energy per octave. Pink noise acoustic stimuli are hypothesized to transduce through the vestibulocochlear nerve, ascend the non-lemniscal pathway, and diffusely recruit neurons across the cortex to depolarize in synchrony with the slow oscillation, reflected by an increase in SWA.[14] Interestingly, anti-phase stimulation (i.e., acoustic stimuli synchronized with the down-slope of slow waves) has been shown to disrupt slow wave architecture and decrease SWA.[7] Thus, precisely timed auditory stimulation can either potentiate or undermine the manifestation of EEG slow wave oscillations.

Among sedatives used in clinical practice, dexmedetomidine is posited to induce states most akin to NREM sleep. An alpha-2 agonist, dexmedetomidine induces slow waves and sedation by reducing cerebral noradrenergic tone, similar to the natural sleep onset process.[15] This is in contrast to the majority of anesthetics that also induce slow waves[16] but have a different principal mechanism of action through the GABA receptor. In fact, slow waves generated via dexmedetomidine infusions resemble those of natural sleep.[16,17] The EEG scalp topography of dexmedetomidine sedation has been described using 64-channel EEG[18]; however cortical and subcortical source localization have not yet been undertaken. Moreover, this investigation did not focus specifically on the topology and source estimation of EEG slow waves. The behavioral phenotype of dexmedetomidine sedation is also similar to natural sleep, as patients can be aroused and continue to breathe spontaneously.[19] These properties have made dexmedetomidine a popular sedative in the intensive care setting. Interestingly, SWA has been shown to reflect depth of sedation and probability of arousal.[29,21] Nonetheless, important mechanistic differences between dexmedetomidine sedation and natural sleep exist, and their relationship remains an area of active investigation.[22]

Despite a rapidly growing literature describing the effects of closed-loop acoustic stimulation on slow oscillations during natural sleep, it remains unknown whether these methods can be applied to slow oscillations during sedation. From a scientific perspective, differential effects of acoustic stimulation during sleep and sedation may help shed light on the underlying mechanisms and relationship between these states. The cortical/subcortical sources of EEG slow waves during dexmedetomidine sedation, as well as their effects on sleep homeostasis also remain to be described. From a clinical perspective, non-pharmacologically enhancing slow oscillations during sedation could have tremendous implications. Considering the relationship of SWA with depth of sedation[23], it may be feasible to use lower drug concentrations to achieve similar brain states and behavioral phenotypes. This would be particularly useful when needing deeper states of sedation, or when using agents whose infusion rates are limited by side effects (e.g., dexmedetomidine-induced bradycardia), and in patients who cannot tolerate high doses due to hemodynamic instability or poor physiological reserve. Using lower anesthetic concentrations augmented by auditory stimulation may also impact the incidence and severity of post-operative complications and neurocognitive disorders. Dissipating sleep pressure using sound could be especially impactful on clinical outcomes in the critical care setting, where dexmedetomidine is often used as a chronic sedative.

In summary, closed loop acoustic stimulation can enhance EEG slow oscillations during natural sleep, but whether auditory stimuli can enhance slow oscillations during sedation was unknown. Acoustically enhancing slow oscillations could provide clinicians with a non-pharmacological adjunct to deepen states of sedation, with potential translation toward improved clinical outcomes in the perioperative and critical care settings.

Data

There are currently no reported data on the effects of closed-loop acoustic stimulation on pharmacologically-induced slow oscillations. Investigations published in the sleep literature generally report increases in SWA of 10-40%, using phase-locked bursts of pink noise.[7-10-12,24,25]

The primary objective of this study is to determine in-phase CLAS enhancement of EEG slow waves during sedation with dexmedetomidine. Secondary objectives are to characterize these potentiated slow waves and their relation to physiologic parameters that define N3 sleep. The corresponding objectives are as follows:

Objective 1: Determine the potentiation of dexmedetomidine-induced EEG slow waves through in-phase closed-loop acoustic stimulation (CLAS).

Objective 2: Assess whether thresholds for responsiveness to peripheral thermal stimulation during dexmedetomidine sedation are modulated by slow wave CLAS.

Objective 3: Assess whether dexmedetomidine sedation with CLAS reduces metrics of slow wave need on the night of the intervention.

Objective 4: Compare modeled brain localization of dexmedetomidine-induced EEG slow waves recorded in the presence and absence of in-phase CLAS.

Overall, these data will be expected to address the question of whether in-phase CLAS augments slow wave oscillations during dexmedetomidine sedation. In light of previous studies of acoustic slow wave enhancement, we expect to be adequately powered to detect a 15% difference in SWA between conditions.[8-12] These data will also form the basis for future volunteer and patient studies specifically investigating the prospect of deepening sedation and fulfilling homeostatic sleep needs with CLAS. They will also inform future studies seeking to modulate slow waves during sedation with other agents such as propofol, benzodiazepines, barbiturates, xenon, nitrous oxide, ketamine, and halogenated ethers.

Participant Selection

Inclusion Criteria

Each participant must meet all of the following criteria: 18-40 years old, American Society of Anesthesiologists Physical Status 1-2.

Exclusion Criteria

Participants will not be enrolled if any of the following criteria are fulfilled: diagnosed sleep disorders, habitually short sleepers, diagnosed psychiatric disorders, use of psychoactive medication (e.g., antidepressants, mood stabilizers or antipsychotics), diagnosed hearing disorders, neck circumference >40 cm, body mass index (BMI)>30, acknowledged recreational drug or nicotine use, resting heart rate during N3 sleep <40 beats per minute, pregnant or nursing females. Resting heart rate during N3 sleep will be measured during the pre-sedation sleep study.

Study Design

Figure 8:
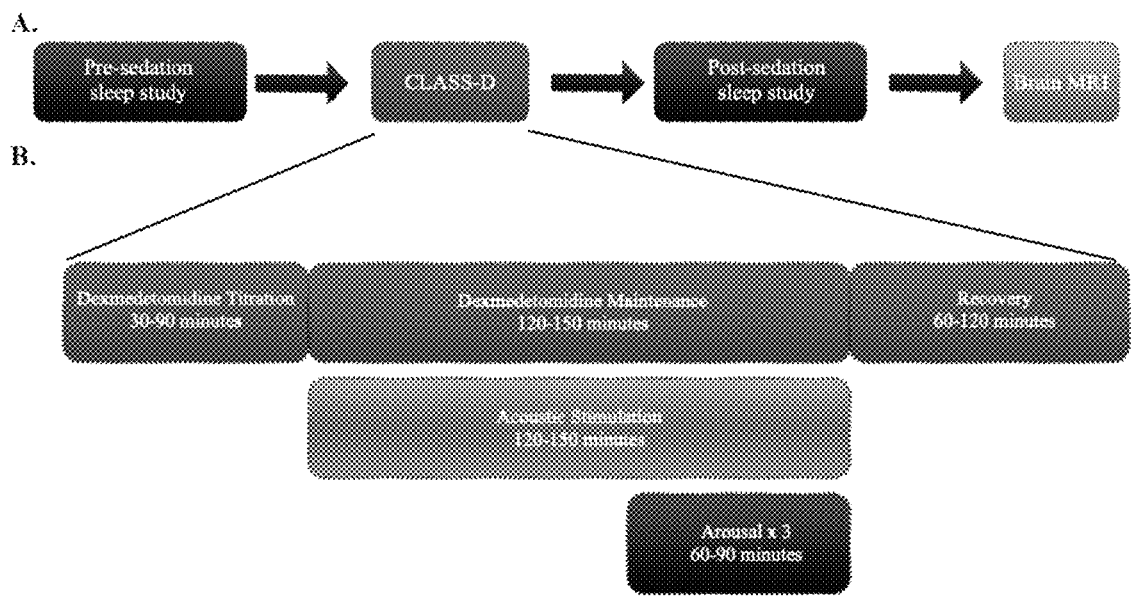
FIG. 8. A. First, participants will complete an ambulatory, unattended home sleep study. The following day, they will undergo the CLASS-D protocol (FIG. 10). A second ambulatory sleep study will be completed on the night following CLASS-D. Finally, a subset of participants will complete a brain MRI at a later date. B. Graphical depiction of CLASS-D protocol. First, a step-dose infusion of dexmedetomidine is used to induce EEG slow waves and suspend purposeful behavior. Second, 60 one-minute blocks of acoustic stimulation (in-phase, antiphase, sham) are delivered to the participant while the TCI maintains a stable effect site concentration of dexmedetomidine. Third, the participant is aroused once during each stimulation condition (in-phase, antiphase, sham). Fourth, the dexmedetomidine infusion rate is decreased to zero and the participant is monitored as they recover their baseline cognitive and physiological status. The entire CLASS-D protocol is predicted to last between four and six hours for each participant.

For each participant, study participation will focus on a single session of dexmedetomidine sedation flanked by unattended ambulatory sleep studies to assess pre-sedation and post-sedation sleep architecture (FIG. 8). The post-sedation sleep study will be followed by a brain MRI to allow precise source localization of EEG slow waves recorded during dexmedetomidine sedation and CLAS. The study design will allow investigators to compare the effects of three acoustic stimulation conditions on slow waves in the same brain (within-subject), at the same time of day, and at the same effect-site concentration of dexmedetomidine. The three conditions are: in-phase stimulation (treatment; pink noise bursts synchronized to the up-slope of slow waves), anti-phase stimulation (active control; pink noise bursts synchronized to the down-slope of slow waves), and sham stimulation (passive control; volume set to zero dB, synchronized to the up-slope of slow waves). FIG. 13 graphically depicts the process of closed-loop acoustic stimulation and contrasts in-phase with antiphase stimulation. Washout periods of acoustic silence will be used during the stimulation protocol to control for short-term resonant effects of acoustic stimulation. Based on highly validated and accurate pharmacokinetic models, the rate of dexmedetomidine infusion will be adjusted throughout the experiment to maintain stable plasma and effect site concentrations.

Study Procedures

Recruitment, Baseline Testing, and Pre-Sedation Sleep

Subjects will be recruited using posted fliers, internet advertisements and Volunteers for Health. Prior to enrolment, subjects will undergo a phone interview to screen for inclusion and exclusion criteria, using an HRPO-approved script.

Informed consent will be obtained, and each participant will complete the Pittsburgh Sleep Quality Index to assess their sleep quality.[26]

After signing informed consent, each subject will undergo training by a research coordinator in quantitative sensory testing (QST). Each subject's baseline heat pain threshold (HPT) and heat pain tolerance threshold (HPTT) will be measured with a Thermal Sensory Analyzer (TSA-11, Medoc, Israel) using the method of limits as defined in the German Research Network on Neuropathic Pain's seminal paper describing standardized protocols and reference values.[27] Specifically, the TSA-11 device will be applied to the subject's non-dominant volar forearm. The contact area of the thermode is 9 cm$^2$, and the baseline temperature is 32° C. Thresholds are obtained by applying ramped thermal stimulation (1° C./s) which is terminated when the subject presses a button. HPT is measured by asking the subject to press the button when the initial feeling of warmth transitions to a feeling of pain. HPTT is measured by asking the subject to press the button when they experience intolerable pain. Each threshold (i.e., HPT and HPTT) is measured four times, and the mean of the last three values is considered to represent a threshold. The maximal temperature that can be applied using the TSA-11 device is 52° C. The maximal thermal energy delivered using this ramping protocol is several orders of magnitude lower that what is required to induce tissue injury. Cumulative equivalent minutes at 43° C. ($CEM_{43}$) is the standard measurement used to define thermal injury thresholds, and is calculated as: $CEM_{43}=tR^{(43-T)}$, where t is the length of exposure in minutes, T is the average temperature during t, and R is 0.25 for T<43 and 0.5 for T>43.[28] The maximal $CEM_{43}$ that can be delivered with the presented protocol is 0.02 (i.e., average temperature of 42° C. over 0.3 minutes), whereas acute minor skin damage begins at a $CEM_{43}$ of 21 (i.e., one thousand-fold higher), and chronic damage at a $CEM_{43}$ of 41. The TSA-11 is used to safely determine heat pain tolerance thresholds.[29] Subjects with baseline HPTT>50° C. will be assessed at a different location on the non-dominant upper extremity. Persistently elevated HPTT>50° C. will lead to exclusion from the study. Subjects who demonstrate an inability to provide consistent QST responses during pre-screening will be excluded from this study.[28]

Each participant will then be provided with a Dreem device, a sleep-monitoring device designed and validated to record ambulatory EEG, heart rate and peripheral oxygen saturation in the home environment.[13] Participants will receive instructions on how to use the device to record ambulatory sleep studies. The principal investigator has extensive experience with this device both in the home setting and in the intensive care unit, in the context of an ongoing trial investigating post-operative delirium. On the night prior to sedation, each participant will wear the device and physiological data will be recorded (i.e., pre-sedation sleep). To assess the effect of CLASS and dexmedetomidine sedation on subsequent nocturnal sleep architecture, participants will also wear the device on the night following sedation (post-sedation sleep). Participants will also be asked to continuously wear an actigraph watch on their non-dominant arm on the days preceding and following the sedation session to objectively measure sleep duration. Participants will also receive standard pre-sedation fasting instructions (NPO 2 hours for clears, 4 hours for liquids, 6 hours for meals) for the dexmedetomidine sedation session.

Simulation and Preparation for Dexmedetomidine Sedation

A target-controlled step-dose infusion of dexmedetomidine based on highly validated pharmacokinetic models will be used to achieve stable plasma concentrations during this study.[20,21,30-32] The target-controlled infusion syringe pump is controlled by Rugloop HO, a Windows® based target controlled infusion and data management program. Rugloop II is not FDA approved for clinical use, however under Code of Federal Regulations Title 21 (21 CFR 812.3(m)) it meets the definition of a non-significant risk device because a) it is not intended as an implant; b) it is not purported nor represented to be for used supporting or sustaining human life; c) it is not for diagnosing, curing, mitigating, or treating disease, or otherwise preventing impairment of human health; and d) it does not present a potential for serious risk to the health, safety, or welfare of a subject. While Rugloop-TCI is a computer-controlled device, it delivers the same agent (dexmedetomidine) as a commercial computer controlled infusion pump, delivers it in the same range of infusion rates, and the infusion rate is continuously displayed and continuously monitored by the supervising physician. In addition, the supervising physician has ultimate control over the infusion rate and dose at all times during the dexmedetomidine administration. Rugloop II was successfully employed to administer target-controlled infusions of remifentanil in a 70-volunteer study at Washington University Medical Center. There were no reported adverse events during this study.

Figure 9:
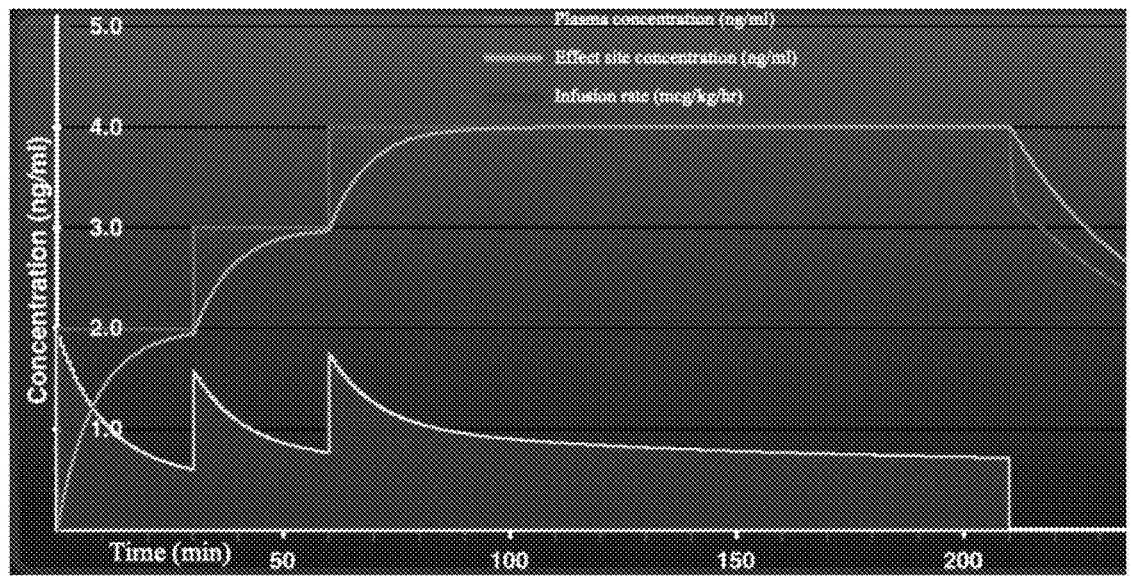
FIG. 9. Simulation of a target-controlled step-dose infusion of dexmedetomidine for a 30-year-old man with a height of 170 cm and a weight of 70 kg. The simulation starts with a target of 2 ng/ml, then increases to a target of 3 ng/ml, and finally to a target of 4 ng/ml (maximum target concentration for this study). This simulation represents the highest possible doses of dexmedetomidine for this man during the study. Note that the step-dose titration may also end at 2 ng/ml or 3 ng/ml if both electrophysiological and behavioral criteria are met. The titration phase is followed by an infusion to maintain the targeted concentration during the acoustic stimulation and arousal phases. Finally, the infusion rate is switched to zero during the recovery phase. Recovery of blood samples to measure dexmedetomidine plasma concentrations are depicted by arrows.

Prior to each sedation session, Rugloop II will be used to simulate the sedation session for each possible targeted concentration (2, 3, and 4 ng/ml). The individualized drug administration simulation will be reviewed by a board-certified anesthesiologist prior to the sedation session. For use in the critical care setting, the manufacturer's label suggests a dexmedetomidine loading dose regimen of 6 mcg/kg/hr for 10 minutes, followed by lower maintenance infusion rates.[33] Infusion rates are generally limited to 6 mcg/kg/hr in volunteer studies.[18,30,31] These precautions are in place to minimize the risk of symptomatic bradycardia. To minimize the risk of adverse hemodynamic effects, the default maximal infusion rate of dexmedetomidine in Rugloop II is set to 6 mcg/kg/hr. FIG. 9 depicts a simulation for a participant.

Dexmedetomidine syringes of identical concentration (16 mcg/ml) and volume (62.5 ml) will be prepared, based on an expected maximum total drug administration of 1000 mcg.

Dexmedetomidine Sedation Session

The organization of sedation session phases are depicted in FIG. 8B.

Pre-Sedation Procedures

On the day of the scheduled sedation, the participant will arrive at the Washington University Medical Center and be accompanied to the Department of Anesthesiology. The team will re-administer the screening questionnaire to ensure that all subjects still meet the inclusion/exclusion criteria and that their health status has not changed. Their ambulatory sleep study will be reviewed, and participants with a mean resting heart rate less than 40 bmp during slow wave sleep will be excluded. A complete history and physical examination will be performed. In addition, the staff will ensure that the subject has adhered to ASA fasting guidelines for sedation/general anesthesia (NPO 2 hours for clears, 4 hours for liquids, 6 hours for meals) by the start of dexmedetomidine administration. Pre-sedation sleepiness will be assessed using the Stanford Sleepiness Scale.[34] The participant will then be accompanied to a post-anesthesia care unit (PACU).

Each subject will have two intravenous catheters (IV) placed, one to receive medications and fluid throughout the study protocol, and another to draw blood samples. These will be placed using a small amount of lidocaine to numb the skin prior to the needle insertion. Standard ASA monitors will be applied: electrocardiogram, blood pressure cuff, pulse oximeter, and breathing rate monitor.

Participants will also have a high-density 64-channel EEG scalp electrode net (EGI/Philips) applied with Elefix conductive gel injected within sensors. Additionally, three shielded electrodes will be affixed to the scalp and connected to the custom made CLAS device: one active electrode, one reference electrode, and one ground electrode. The CLAS device consists of EEG amplifiers, a circuit board, a sound card, a visual display, and a battery, all shielded in a metal case and connected to a separate computer for software interfacing. The device receives EEG input, amplifies and filters the signals, tracks the phase of a pre-defined bandwidth (e.g., 0.5-4 Hz), and synchronizes audio output to a phase specified by the investigators.

Following application of all monitors, a QST will be performed to measure HPT and HPTT at the non-dominant forearm. If HPTT is not greater than 50° C., the area will be marked. If HPTT is greater than 50° C., the test will be repeated at a different location on the non-dominant forearm and repeated until the HPTT is found to be less than 50° C. The final location will then be marked and all subsequent QST measurements will be made at this location. Persistently elevated HPTT>50° C. will lead to exclusion from the study. EEG data will be recorded during HPPT testing.

The sedation protocol will be completed in a location equipped with standard monitoring, airway equipment, suction, and a board-certified anesthesiologist, per normal standard of practice guidelines. Participants will be instructed to perform a previously validated behavioral task throughout the protocol, while keeping their eyes closed: "squeeze the ball during inspiration and release it during expiration".[35] Participants will be considered responsive whenever they perform the task consistently (at least five consecutive correct squeezes), and unresponsive after five consecutive failures to squeeze during inspiration. After confirming adequate comprehension, 10 minutes of baseline awake EEG measurements will be recorded: five minutes with eyes open and five minutes with eyes closed. After completing all questionnaires and baseline recordings, and ensuring that all monitors are functional, the CLASS-D protocol will begin (FIG. 8B). The protocol can be broadly separated into four phases: 1. Dexmedetomidine titration phase; 2. Acoustic stimulation phase; 3. Arousal phase; and 4. Recovery phase.

Dexmedetomidine Titration Phase

The participant will be instructed to close their eyes and perform the behavioral task: "squeeze the ball during inspiration and release it during expiration". An initial target concentration of 2 ng/ml will be entered into Rugloop and the infusion will begin. BP, HR, and SpO2 data will be streamed to Rugloop. A time stamp will be added to the EEG, EMG, and video feeds, marking the beginning of the experiment. Once the predicted plasma and effect site concentrations of dexmedetomidine have reached 2 ng/ml, two criteria will be assessed to determine if the experiment may progress to the acoustic stimulation phase. The first criterion is behavioral: if the participant is no longer performing the behavioral task of squeezing their dominant hand during inspiration, then this criterion is met. The second criterion is electrophysiological: if large amplitude (>20 microvolts) slow waves (0.5-4 Hz) are present on the real-time EEG monitor, then this criterion is met. The physician assessing the presence of EEG slow waves has completed accredited training in the interpretation of the EEG of humans undergoing sedation and anesthesia.[36,37] If both criteria are met, then the experiment may proceed to the acoustic stimulation phase. If one or both of the criteria are not met, then the targeted concentration will be increased to 3 ng/ml. Once the predicted plasma and effect site concentrations reach 3 ng/ml, the two criteria will be reassessed. If both criteria are met, then the experiment may proceed to the acoustic stimulation phase. If one or both of the criteria are not met, then the targeted concentration will be increased to 4 ng/ml. Once the predicted plasma and effect site concentrations reach 4 ng/ml, the two criteria will be reassessed. If both criteria are met, then the experiment may proceed to the acoustic stimulation phase. If one or both of the criteria are not met, then the experiment will be aborted. Notably, previous studies have used this step-wise approach to achieve TCI targets as high as 8 ng/ml in order study the neurological and physiological effects of dexmedetomidine.[33] Achieving the desired effect-site concentration may take up to 90 minutes. Level of sedation will be monitored throughout the experiment using the squeeze task described above, video recording, high-density electroencephalography and standard ASA monitors.

To corroborate and correct the predicted plasma concentrations of dexmedetomidine during the experiment, 5 ml venous blood samples will be collected twice during the experiment: once between the dexmedetomidine titration and acoustic stimulation phases, and once between the arousal and recovery phases (FIG. 8B). The sample will be drawn from the peripheral IV not in use for infusing dexmedetomidine. It will be placed on ice prior to processing.

Each blood sample will be cooled to +4 degrees Celsius and undergo five minutes of spin time in a centrifuge at 3,000 RCF to separate the plasma component. Ethylene diamine triacetic acid (EDTA) will be used as the anticoagulant of choice. Once the plasma has been separated, it will be transferred to a 1.5 ml EDTA-treated polyproline cryovial with screw on lid and conical bottom. The cryovial will then be stored at −70--80 degrees Celsius until being shipped overnight to Denver (CO) on dry ice. Plasma dexmedetomidine levels will be measured from these plasma samples using liquid chromatography-mass spectrometry (LC-MS) at the iC42 Clinical Research and Development Laboratory of the University of Colorado. Dexmedetomidine will be quantified in 100 µL EDTA plasma, using a validated chromatography-mass spectrometry (LC-MS) assay. One hundred µL EDTA plasma will be transferred into a 96-1 mL-well plate and a protein precipitation solution (methanol/0.2 M $ZnSO_4$, 7:3, v/v) containing the deuterated internal standard will be added. After centrifugation, injection directly from the 96-well plate into the LC/LC-MS/MS system (10 µL injection volume) and online extraction, samples will be back-flushed onto the analytical HPLC column and compounds will be separated using a mobile phase of methanol (containing 0.01% formic acid) and 0.01% formic acid. The HPLC system will be interfaced with a Sciex AP14000 tandem quadrupole mass spectrometer via a turbo spray source. The mass spectrometer will be run in the positive multiple reaction monitoring (MRM) mode. The assay is validated following current international guidances (FDA, OECD/ICH, CLSI) and has a lower limit of quantification of 100 pg/mL. The range of reliable response is 0.1-500 ng/mL ($r^2$>0.99). Inter-assay accuracy is within 85-115% and total imprecision is better than 15% (except at the lower limit of quantitation: <20%). There was no carry-over, ion suppression or matrix interferences. Extracted sample (autosampler) stability for at least 24 hours, long-term storage stability (−80° C.) and stability during 3 freeze-thaw cycles has been established.

Acoustic Stimulation Phase

Figure 10:
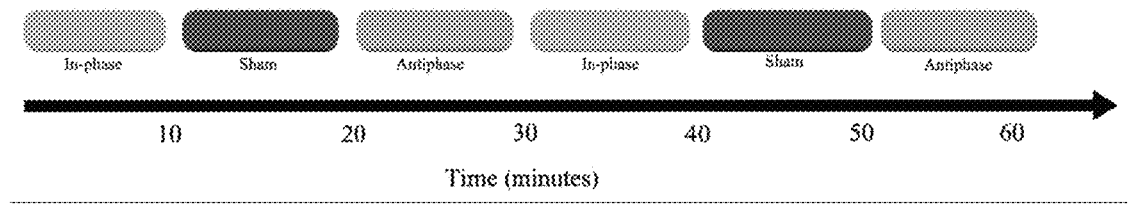
FIG. 10. Sample acoustic stimulation protocol. In this sample, a stimulation condition lasts 9 minutes, transitions into one minute of silence and then into 9 minutes of another stimulation condition. The entire protocol lasts 60 minutes.

After confirming that the behavioral and electrophysiological criteria are met, the dexmedetomidine titration phase ends and the acoustic stimulation phase begins. Custom-made scripts in Labview and/or Matlab will track the phase of slow waves (0.5-4 Hz) and trigger the binaural delivery of acoustic stimuli via noise-isolating earphones. The acoustic stimuli will be identical to those used in previous sleep studies: bursts of pink 1/f noise of 50 ms duration with a 5 ms rising and falling time.[7,24] Sound volume will be calibrated to 65 dB using a sound level meter. The volume will be reduced if it arouses the participant. The acoustic stimulation phase lasts one hour and can be conceptually divided into 60 one-minute blocks (FIG. 10). Prior to the experiment, each block will be assigned to one condition: in-phase stimulation, anti-phase stimulation, sham stimulation, or washout silence. Sequential blocks may be assigned to the same condition (e.g., five consecutive blocks of in-phase stimulation). Washout blocks will precede transitions from one condition to another (e.g., one washout block between blocks of in-phase and anti-phase stimulation). After completing 60 one-minute acoustic stimulation blocks, subjects will enter the arousal phase of the experiment.

Arousal Phase

Figure 11:
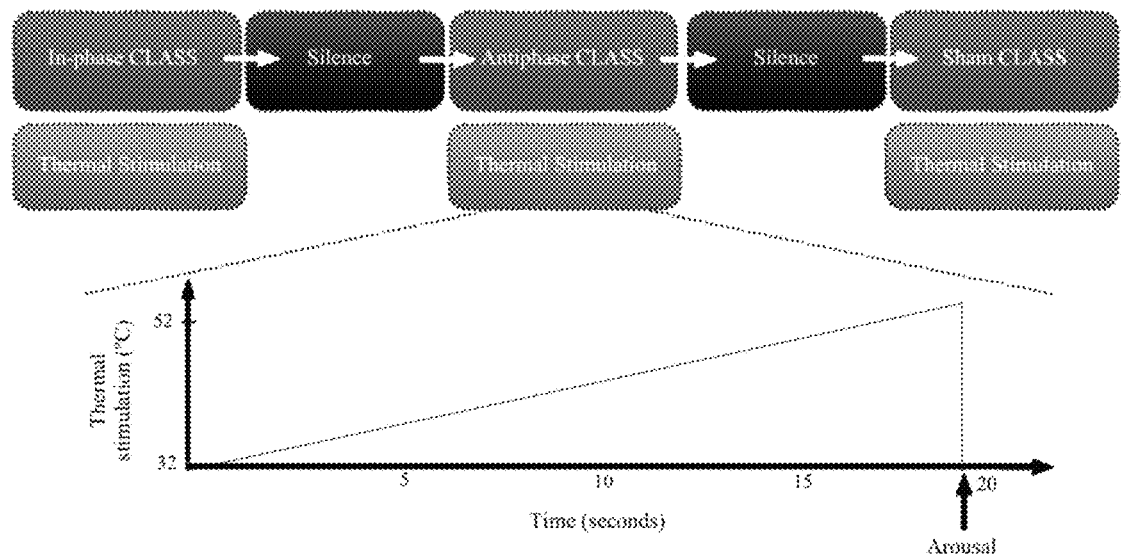
FIG. 11. Sample arousal protocol. Ramping thermal stimulation of the non-dominant upper extremity will be used to arouse participants from each of the three CLASS conditions. The temperature (° C.) at which participants are aroused will be compared between conditions to assess whether in-phase CLASS increases arousal thresholds. Fifteen minutes of acoustic and thermal silence will follow each arousal to allow the participant's EEG to return to baseline.

Subjects will undergo three arousals during this phase of the experiment: one during in-phase stimulation, one during anti-phase stimulation, and one during sham stimulation (FIG. 11). The order of the conditions under which subjects are aroused will be pre-determined before the experiment and balanced across subjects to control for interactions between stimulation conditions and lasting effects of arousal. Each arousal will be preceded by at least 3 consecutive minutes of acoustic stimulation, which will continue during the arousal procedure. The arousal procedure consists of the same ramping thermal stimulation used during pre-sedation QST. The cardinal difference between pre-sedation QST and arousal QST is that one of the investigators will be tasked with pressing the button to end the thermal ramp instead of the subject. Criteria for the investigator to press the button will be clear evidence of arousal, specifically, purposeful behavior in response to the thermal stimulation. The investigator will also be able to terminate the thermal stimulation at their clinical discretion (e.g., in the unlikely event that the subject exhibits non-purposeful behavior indicating that they are in pain before any purposeful movement). Vital signs, EEG, and video recording will also be used to review the time of arousal during post-hoc analysis. EEG changes reflective of arousal during dexmedetomidine sedation consist of decreasing SWA and loss of spindles.[20] Assessors of arousal will be blinded to the acoustic stimulation conditions. Once a subject has been definitively aroused, thermal stimulation will cease and a 15-minute washout period without any thermal or acoustic stimulation will follow to allow the EEG to return to its pre-arousal baseline.[20] Immediately following arousal, subjects will also be asked to report any memories and to rate their pain on a visual analog scale. This protocol will be repeated three times, once for each stimulation condition. The predicted effect-site concentration of dexmedetomidine will be maintained by TCI throughout the acoustic stimulation and arousal phases of the experiment. After the third arousal and washout period, a second 5 ml venous blood sample will be drawn for quantitation of dexmedetomidine concentration and placed on ice for processing. The dexmedetomidine infusion rate will then be set to zero and the recovery phase will begin.

Recovery Phase

All physiological monitoring will continue during recovery from sedation. Behavioral recovery will be measured with the same paradigm used during induction. Acoustic stimulation conditions (i.e., in-phase vs. anti-phase vs. sham) may continue during the recovery phase. When a subject is reliably performing the behavioral task (i.e., squeezing during inspiration, releasing during expiration), they will be considered to be awake and the experiment will terminate. At this time, all acoustic stimulation will cease and the earphones will be removed. The subject may be prompted to perform the behavioral task. The subject will continue to be monitored by staff until they meet standard discharge criteria following sedation. A post-sedation questionnaire will then be administered to assess the participant's memories of the experiment. The Stanford Sleepiness Scale will also be re-administered. The subject will then be discharged home with the DREEM device to assess structure of sleep on the night of the study. They will also receive standard post-sedation discharge instructions and be accompanied home by a trustworthy person of their choosing.

Post-Sedation Sleep and MRI

Participants will be instructed to wear the DREEM and record data during overnight sleep on the night following the sedation protocol. They will return the device the following day and complete a final sleep questionnaire and sleepiness assessment. Participants will also be scheduled for non-contrast brain MRI at a later date. The anatomical data obtained from the individual brain MRI will be used for source localization of EEG slow waves.

Methods

Observations and Measurements

Measurements acquired for the pre- and post-sedation datasets will include EEG, heart rate (HR), peripheral oxygen saturation (SpO2), and movement. Measurements acquired for the sedation datasets will include EEG, electromyography (EMG), HR, SpO2, respiratory rate, non-invasive blood pressure (NIBP), movement, and audiovisual recordings. Plasma dexmedetomidine levels will also be measured at two time points during the dexmedetomidine infusion. Questionnaires administered include the Stanford Sleepiness Scale and the Pittsburgh Sleep Quality Index.

Primary Outcome Measures

Slow wave activity (SWA), cumulative slow wave activity (cSWA).[8]

Secondary Outcome Measures

Depth of sedation will be measured as the thermal stimulation (° C.) sufficient to arouse subjects, defined as 1) EEG reversion from slow wave oscillations and 2) withdrawal movement or grimacing.

Sleep homeostasis during pre- and post-sedation sleep will be assessed via changes in EEG SWA and slow wave features (amplitude, slope) between the first and last sleep cycles of the night, as well as cumulative SWA for the entire night (also called slow wave energy).[8,12,38] De-identified EEG within the Dreem will be uploaded to the manufacturer's website HDFS format data will be downloaded and processed using custom-written MATLAB subroutines.

Sleepiness before and after the sedation session will be measured with the Stanford Sleepiness Scale. Subjective sleep quality will be measured using the Pittsburgh Sleep Quality Index.

Structural MRI (T1, MPRAGE scan) and high-density EEG will be used to estimate the neurological sources of EEG slow waves and other motifs of interest during sedation and acoustic stimulation. The models will be generated in Brainstorm[39] running in MATLAB.

Statistical Methods

A general mixed effects model will be used to compare primary outcome measures across the three conditions. The model will include time and condition (sham, in-phase, and anti-phase stimulation) as fixed effects and account for age and sex. Paired T tests or U-tests will be used to compare measures of sleep homeostasis between pre- and post-sedation sleep (depending on normality of measures). Logistic regression modelling of responsiveness to thermal stimulation will be used to compare arousal thresholds during in-phase vs. antiphase vs. sham stimulation.

Sample Size

A convenience sample size of 14 participants will be used for this study. Previous volunteer studies investigating closed loop acoustic stimulation during sleep have used sample sizes of 11-28 participants to detect changes in SWA of 10-40%.[7-11,13,14,24,25] Based on this literature, we conservatively expect this experiment to be powered to detect a change in SWA of 15%.

Management of Intercurrent Events

Adverse Event Definition

An adverse event (AE) is any untoward medical occurrence in a subject participating in an investigational study or protocol regardless of causality assessment. An adverse event can be an unfavorable and unintended sign (including an abnormal laboratory finding), symptom, syndrome, or disease associated with or occurring during the use of an investigational product whether or not considered related to the investigational product.

These events may be:
i) Definitely related: clearly associated with study drug/treatment
ii) Probably related: likely associated with study drug/treatment
iii) Possibly related: may be associated with study drug or other treatment
iv) Unlikely to be related, or
v) Definitely not related to the study drug/treatment For reporting purposes, an AE should be regarded as definitely or probably related to the regimen if the investigator believes that at least one of following criteria are met:
i) There is a clinically plausible time sequence between onset of the AE and the administration of the study drug or treatment.
ii) There is a biologically plausible mechanism for the study drug or treatment causing or contributing to the AE.
iii) The AE cannot be attributed solely to concurrent/underlying illness, other drugs, or procedures.
iv) A potential alternative cause does not exist.

Serious Adverse Events (SAE): An adverse drug experience occurring at any dose that results in any of the following outcomes:
i) Death
ii) A life-threatening adverse drug experience
iii) Inpatient hospitalization or prolongation of existing hospitalization
iv) A persistent or significant disability &/or incapacity
v) A congenital anomaly or birth defect Important medical events that may not result in death, be life-threatening, or require hospitalization may be considered a serious adverse drug experience when, based upon appropriate medical judgment, they may jeopardize the patient or subject and may require medical or surgical intervention to prevent one of the outcomes listed in this definition. A serious adverse experience includes any experience that is fatal or immediately life threatening, results in a persistent or significant disability/incapacity, requires or prolongs in-patient hospitalization, cancer, or overdose.

Other important medical events that may not result in death, not be life-threatening, or not require hospitalization may be considered a serious adverse experience when, based upon appropriate medical judgment, the event may jeopardize the subject/patient and may require medical intervention to prevent one of the outcomes listed previously.

Expected adverse events are those adverse events that are listed in the protocol, the Investigator's Brochure (current edition), drug labeling or in the study informed consent document.

These will include relative bradycardia, hypotension, and hypertension.

Unexpected adverse events are those that:
i) are not described in the Investigator's Brochure or drug labeling
ii) are not anticipated in the study informed consent. This includes adverse events for which the specificity or severity is not consistent with the description in the informed consent.

Unanticipated problem: Per FDA Procedural Guidance for Clinical Investigators, Sponsors, and IRBs (January 2009), a serious problem is one that has implications for the conduct of the study (requiring a significant and usually safety-related, change in the protocol such as revising inclusion/exclusion criteria or including a new monitoring requirement, informed consent or investigator's brochure).

Unanticipated problem Reporting: Per 21 CFR 312.66, 312.53 (c)(1)(vii), and 56.108(b)(1), should an Unanticipated problem occur during the investigation, the investigator will promptly report all unanticipated problems involving risks to human subjects or others to IRBMED/FDA.

The severity or grade of an adverse event may be measured using the following definitions:

Mild: Noticeable to the subject, but does not interfere with subject's expected daily activities, usually does not require additional therapy or intervention, dose reduction, or discontinuation of the study.

Moderate: Interferes with subject's expected daily activities, may require some additional therapy or intervention but does not require discontinuation of the study.

Severe: Extremely limits the subject's daily activities and may require discontinuation of study therapy, and/or additional treatment or intervention to resolve.

Event reporting: The study will comply with the IRB & FDA reporting requirements and guidelines.

Premature Discontinuation

Profound treatment-resistant bradycardia, hypertension, or hypotension will trigger the premature discontinuation of the sedation protocol. Profound bradycardia will be defined as a heart rate less than 40 beats per minute for more than three minutes. Profound hypotension and hypertension will be defined as a 30% decrease or increase from baseline MAP for more than five minutes, respectively. The inability to maintain a patent airway and/or a sustained decrease in SpO2 below 92% despite the use of simple airway maneuvers and supplementation of up to 4 liters per minute of oxygen will also lead to termination of the sedation protocol. Sustained cardiac conduction abnormalities will also lead to termination of the sedation protocol. The PI reserves the right to discontinue the study protocol at any time for subject safety.

Potential Risks

The most common adverse events associated with dexmedetomidine infusions are bradycardia, hypotension and hypertension. The dose-response relationships of dexmedetomidine with heart rate (HR), mean arterial pressure (MAP) and level of sedation have been rigorously investigated.[31,32] At low plasma concentrations (<1 ng/ml), dexmedetomidine exerts agonism at alpha2 receptors in the central nervous system, resulting in a decrease in peripheral vascular resistance and heart rate. At higher plasma concentrations (>4 ng/ml), it agonizes alpha2 receptors on vascular smooth muscle, resulting in hypertension and worsening reflex bradycardia. To avoid high peak plasma levels, studies in healthy volunteers generally avoid boluses and limit infusion rates to a maximum of 6 mcg/kg/hr.[17,30] The commonly used loading dose of 1 mcg/kg over 10 minutes (infusion rate of 6 mcg/kg/hr) originates from an early study of dexmedetomidine in healthy volunteers using infusion rates of 1.5, 3, 6, and 12 mcg/kg/hr over 10 minutes.[40] The target effect site concentrations of 2.0-4.0 ng/ml strike a good balance between depth of sedation and hemodynamic effects. Most participants will be moderately sedated, have a near-baseline MAP and a HR>75% from baseline.[31] It is worth noting that volunteer studies have been safely conducted with target concentrations as high as 8 ng/ml.[30] Furthermore, dexmedetomidine is commonly infused for several hours to days at a rate of 1.5 mcg/kg/hr in intensive care units to critically ill patients, which culminates to a steady-state concentration of 2.5-3.0 ng/ml.

Intravenous fluids, glycopyrrolate, phenylephrine, and hydralazine may be used at the discretion of the attending anesthesiologist to treat bradycardia, hypotension, and hypertension, respectively. All adverse events will be reported and followed until satisfactory resolution. The description of the adverse experience will include the time of onset, duration, intensity, etiology, relationship to the study drug (none, unlikely, possible, probable, highly probable), and any treatment required. Participant will not be allowed to work or drive until the next day.

Procedures to Minimize Potential Risks

Risks for study subjects will be minimized by initial screening, asking the inclusion/exclusion criteria questions, a complete history and physical by a trained anesthesiologist and urine pregnancy test, ASA standard monitoring and standard fasting guidelines.[41] A staff anesthesiologist or anesthesiology resident will be present at all times. An ACLS-certified anesthesiologist will be immediately available.

Steps will be taken to minimize the risk of drug administration errors. Pharmacy staff will prepare dexmedetomidine drug syringes for each session. The study team has designated a standard of 60 milliliter syringes filled with dexmedetomidine at 16 mcg/ml for all study sessions. The working concentration is four times the standard working concentration used in the OR and ICU settings and is based on a projected maximal dexmedetomidine administration of 1000 mcg for an entire session (maximal target infusion rate for plasma concentration of 4 ng/ml, 90 kg male). The use of standardized drug syringe type, volume, and working concentration is designed to maximize participant safety.

Decades of use have shown that target-controlled infusion devices are a mature and safe technology with over 90 published articles using Rugloop-TCI.[42] A series of recently published studies have safely used Rugloop-TCI to achieve dexmedetomidine plasma concentrations as high as 8 ng/ml, twice as high as the maximal concentration proposed in our study.[30-32] The use of a target controlled infusion device delivers the same medication (dexmedetomidine) over the same range of infusions as a continuous infusion pump. The supervising physician ultimately determines the infusion rate and the device continuously displays the infusion rate. In addition, the sedation session will be conducted with continuous vital sign monitoring by an anesthesia provider. In the unlikely event that they are needed, drugs and equipment to treat any anticipated or unanticipated side effects will be immediately available. Resuscitation capabilities will be immediately available. Following completion of the dexmedetomidine infusion, participants will be monitored until they return to their baseline mental status as assessed by a specialty trained anesthesiologist, and will be instructed not to drive themselves home.

The maximal thermal energy that can be delivered during pre-sedation QST and the arousal phases of this experiment is a thousand-fold lower than what is required to induce acute mild tissue injury.

To minimize breach of confidentiality risk, the minimum necessary data will be collected to achieve the study objectives, datasets will be de-identified after study completion, and data and code keys will be stored in password-protected databases and key-locked filing cabinets.

Data and Safety Monitoring Plan

The specific monitoring plan for this investigation is commensurate with the risks and the size and complexity of the studies planned. The PI will monitor the study for any adverse and serious events. Based on the small size and relatively low risks nature of the protocol, an anesthesiologist without current collaborations with the study team will also review the study in lieu of a Data Safety Monitoring Board. All serious events will be reported to the HRPO within 7 days. Should a serious adverse event occur the study will be stopped. An investigation will be conducted and finding report generated before the study is resumed. After seven participants have been enrolled, the study will undergo a planned audit by the Anesthesiology's Division of Clinical and Translational Research for quality assurance and safety assessment and the anesthesiologist monitoring the study.

Protection of Human Subjects

The study will be conducted with strict adherence to Washington University Institutional Review Board protocol and consent form approval. An American Board of Anesthesiology board-certified and GCP-certified anesthesiologist with experience in conducting clinical studies will lead the study. Safety and privacy of study participants will be safeguarded.

Participant confidentiality will be maintained through de-identification of personal health information. Identity and linking information will be locked cabinet within the principal investigator's (PI) office, which is locked outside of business hours. Electronic data will be password encrypted on secure servers.

Sources of Materials

Collected materials will be restricted to a brain MRI, video recordings collected during experimental sessions and physiological data collected during physiological sessions as well as those collected by the Dreem device during sleep at home. These physiological data include EEG, EMG, SpO2, HR, NIBP, and movement.

REFERENCES

1. Prerau M J, Brown R E, Bianchi M T, Ellenbogen J M, Purdon P L. Sleep Neurophysiological Dynamics Through the Lens of Multitaper Spectral Analysis. Physiology (Bethesda). 2017; 32(1):60-92.
2. Leger D, Debellemaniere E, Rabat A, Bayon V, Benchenane K, Chennaoui M. Slow-wave sleep: From the cell to the clinic. Sleep Med Rev. 2018; 41:113-132.
3. Neske G T. The Slow Oscillation in Cortical and Thalamic Networks: Mechanisms and Functions. Front Neural Circuits. 2015; 9:88.
4. Borbely A A. A two process model of sleep regulation. Hum Neurobiol. 1982,1(3):195-204.
5. Marshall L, Helgadottir H, Molle M, Born J. Boosting slow oscillations during sleep potentiates memory. Nature. 2006; 444(7119):610-613.
6. Massimini M, Ferrarelli F, Esser S K, et al. Triggering sleep slow waves by transcranial magnetic stimulation. Proc Natl Acad Sci USA. 2007; 104(20):8496-8501.
7. Ngo H V, Martinetz T, Born J, Molle M. Auditory closed-loop stimulation of the sleep slow oscillation enhances memory. Neuron. 2013; 78(3):545-553.
8. Garcia-Molina G, Tsoneva T, Jasko J, et al. Closed-loop system to enhance slow-wave activity. J Neural Eng. 2018; 15(6):066018.
9. Besedovsky L, Ngo H V, Dimitrov S, Gassenmaier C, Lehmann R, Born J. Auditory closed-loop stimulation of EEG slow oscillations strengthens sleep and signs of its immune-supportive function. Nat Commun. 2017; 8(1): 1984.
10. Leminen M M, Virkkala J, Saure E, et al. Enhanced Memory Consolidation Via Automatic Sound Stimulation During Non-REM Sleep. Sleep. 2017; 40(3).
11. Papalambros N A, Santostasi G, Malkani R G, et al. Acoustic Enhancement of Sleep Slow Oscillations and Concomitant Memory Improvement in Older Adults. Front Hum Neurosci. 2017; 11:109.
12. Grimaldi D, Papalambros N A, Reid K J, et al. Strengthening sleep-autonomic interaction via acoustic enhancement of slow oscillations. Sleep. 2019.
13. Debellemaniere E, Chambon S, Pinaud C, et al. Performance of an Ambulatory Dry-EEG Device for Auditory Closed-Loop Stimulation of Sleep Slow Oscillations in the Home Environment. Front Hum Neurosci. 2018; 12:88.
14. Bellesi M, Riedner B A, Garcia-Molina G N, Cirelli C, Tononi G. Enhancement of sleep slow waves: underlying mechanisms and practical consequences. Front Syst Neurosci. 2014; 8:208.
15. Akeju O, Hobbs L E, Gao L, et al. Dexmedetomidine promotes biomimetic non-rapid eye movement stage 3 sleep in humans: A pilot study. Clin Neurophysiol. 2018; 129(1):69-78.
16. Purdon P L, Sampson A, Pavone K J, Brown E N. Clinical Electroencephalography for Anesthesiologists: Part I: Background and Basic Signatures. Anesthesiology. 2015,123(4):937-960.
17. Xi C, Sun S, Pan C, Ji F, Cui X, Li T. Different effects of propofol and dexmedetomidine sedation on electroencephalogram patterns: Wakefulness, moderate sedation, deep sedation and recovery. PLoS One. 2018; 13(6): e0199120.
18. Akeju O, Kim S E, Vazquez R, et al. Spatiotemporal Dynamics of Dexmedetomidine-Induced Electroencephalogram Oscillations. PLoS One. 2016; 11(10):e0163431.
19. Ebert T J, Hall J E, Barney J A, Uhrich T D, Colinco M D. The effects of increasing plasma concentrations of dexmedetomidine in humans. Anesthesiology. 2000; 93(2):382-394.
20. Sleigh J W, Vacas S, Flexman A M, Talke P O. Electroencephalographic Arousal Patterns Under Dexmedetomidine Sedation. Anesth Analg. 2018; 127(4):951-959.
21. Scheinin A, Kallionpaa R E, Li D, et al. Differentiating Drug-related and State-related Effects of Dexmedetomidine and Propofol on the Electroencephalogram. Anesthesiology. 2018,129(1):22-36.
22. Guldenmund P, Vanhaudenhuyse A, Sanders R D, et al. Brain functional connectivity differentiates dexmedetomidine from propofol and natural sleep. Br J Anaesth. 2017,119(4):674-684.
23. Ni Mhuircheartaigh R, Warnaby C, Rogers R, Jbabdi S, Tracey I. Slow-wave activity saturation and thalamocortical isolation during propofol anesthesia in humans. Sci Transl Med. 2013; 5(208):208ra148.
24. Santostasi G, Malkani R, Riedner B, et al. Phase-locked loop for precisely timed acoustic stimulation during sleep. J Neurosci Methods. 2016; 259:101-114.
25. Ong J L, Lo J C, Chee N I, et al. Effects of phase-locked acoustic stimulation during a nap on EEG spectra and declarative memory consolidation. Sleep Med. 2016; 20:88-97.
26. Buysse D J, Reynolds C F, 3rd, Monk T H, Berman S R, Kupfer D J. The Pittsburgh Sleep Quality Index: a new instrument for psychiatric practice and research. Psychiatry Res. 1989,28(2):193-213.
27. Rolke R, Baron R, Maier C, et al. Quantitative sensory testing in the German Research Network on Neuropathic Pain (DFNS): standardized protocol and reference values. Pain. 2006; 123(3):231-243.
28. Yarmolenko P S, Moon E J, Landon C, et al. Thresholds for thermal damage to normal tissues: an update. Int J Hyperthermia. 2011,27(4):320-343.
29. Haroutounian S, Nikolajsen L, Bendtsen T F, et al. Primary afferent input critical for maintaining spontaneous pain in peripheral neuropathy. Pain. 2014; 155(7): 1272-1279.
30. Hannivoort L N, Eleveld D J, Proost J H, et al. Development of an Optimized Pharmacokinetic Model of Dexmedetomidine Using Target-controlled Infusion in Healthy Volunteers. Anesthesiology. 2015,123(2):357-367.
31. Colin P J, Hannivoort L N, Eleveld D J, et al. Dexmedetomidine pharmacodynamics in healthy volunteers: 2. Haemodynamic profile. Br J Anaesth. 2017; 119(2):211-220.
32. Colin P J, Hannivoort L N, Eleveld D J, et al. Dexmedetomidine pharmacokinetic-pharmacodynamic modelling in healthy volunteers: 1. Influence of arousal on bispectral index and sedation. Br J Anaesth. 2017; 119 (2):200-210.
33. Weerink M A S, Struys M, Hannivoort L N, Barends C R M, Absalom A R, Colin P. Clinical Pharmacokinetics and Pharmacodynamics of Dexmedetomidine. Clin Pharmacokinet. 2017; 56(8):893-913.
34. Hoddes E, Zarcone V, Smythe H, Phillips R, Dement W C. Quantification of sleepiness: a new approach. Psychophysiology. 1973,10(4):431-436.
35. Prerau M J, Hartnack K E, Obregon-Henao G, et al. Tracking the sleep onset process: an empirical model of behavioral and physiological dynamics. PLoS Comput Biol. 2014,10(10):e1003866.
36. Purdon P L, Brown E N. Clinical Electroencephalography for the Anesthesiologist. https://www.phscpd.org/activities/activity-detail/clinical-electroencephalography-for-the-anesthesiologist, 2017.
37. Purdon P L, Colvin C A, Brown E N. EEG For Anesthesia. http://eegforanesthesia.iars.org/, 2019.
38. Riedner B A, Vyazovskiy W, Huber R, et al. Sleep homeostasis and cortical synchronization: Ill. A high-density EEG study of sleep slow waves in humans. Sleep. 2007; 30(12):1643-1657.
39. Tadel F, Baillet S, Mosher J C, Pantazis D, Leahy R M. Brainstorm: a user-friendly application for MEG/EEG analysis. Computational intelligence and neuroscience. 2011; 2011:879716.
40. Bloor B C, Ward D S, Belleville J P, Maze M. Effects of intravenous dexmedetomidine in humans. II. Hemodynamic changes. Anesthesiology. 1992,77(6):1134-1142.
41. Practice Guidelines for Preoperative Fasting and the Use of Pharmacologic Agents to Reduce the Risk of Pulmonary Aspiration: Application to Healthy Patients Undergoing Elective Procedures: An Updated Report by the American Society of Anesthesiologists Task Force on Preoperative Fasting and the Use of Pharmacologic Agents to Reduce the Risk of Pulmonary Aspiration. Anesthesiology. 2017; 126(3):376-393.
42. Absalom A R, Glen J I, Zwart G J, Schnider T W, Struys M M. Target-Controlled Infusion: A Mature Technology. Anesth Analg. 2016; 122(1):70-78.

Example 4: Closed-Loop Acoustic Stimulation During Sedation with Dexmedetomidine (Class-D)

This example describes the CLASS-D protocol for a within-subject, crossover, controlled, interventional trial with healthy volunteers.

Abstract

Introduction. The relative power of slow-delta oscillations in the electroencephalogram (EEG), termed slow wave activity (SWA), correlates with level of unconsciousness. Acoustic enhancement of SWA has been reported for sleep states, but it remains unknown if pharmacologically-induced SWA can be enhanced using sound. Dexmedetomidine is a sedative whose EEG oscillations resemble those of natural sleep. This study will answer two questions: (1) can SWA during dexmedetomidine sedation be enhanced using phase-locked acoustic stimulation; and (2) does acoustic enhancement of SWA affect a patient's level of unconsciousness. Secondary objectives will evaluate the effects of dexmedetomidine sedation on subsequent nocturnal sleep and to compare natural and pharmacological slow waves.

Methods and Analysis. Closed-Loop Acoustic Stimulation during Sedation with Dexmedetomidine (CLASS-D) is a within-subject, crossover, controlled, interventional trial with healthy volunteers. Each participant will be sedated with a dexmedetomidine target-controlled infusion (TCI). Participants will undergo three CLASS conditions in a multiple crossover design: in-phase (phase-locked to slow wave upslopes), anti-phase (phase-locked to slow wave downslopes), and sham (silence). High-density EEG recordings will assess the effects of CLASS across the scalp. Volitional behavioral tasks and thermal arousal procedures will assess the anesthetic effects of CLASS. Ambulatory sleep studies will be performed on nights immediately preceding and following the sedation session. EEG effects of CLASS will be assessed using linear mixed-effects models. The impacts of CLASS on behavior and arousal thresholds will be assessed using logistic regression modeling. Parametric modeling will determine differences in sleepiness and measures of sleep homeostasis before and after sedation. This investigation will elucidate 1) the potential of exogenous stimulation to potentiate SWA during sedation; 2) the physiologic significance of this intervention; and 3) the connection between EEG slow waves observed during sleep and sedation.

Introduction

Enhancement of EEG Slow Oscillations During Sleep

Sleep addresses critical physiologic needs in humans and most living organisms. Although the neurological mechanisms underlying sleep are still under investigation, the electroencephalographic (EEG) correlates of sleep states are established.[1] Slow (0.1-1 Hz) and delta (1-4 Hz) waves are large amplitude, low frequency EEG oscillations that define non-rapid eye movement (NREM) sleep stage 3 (N3). Importantly, they have been shown to play roles in physiologic restoration, memory consolidation, and dissipating homeostatic sleep pressure.[2] At the cellular level, they correspond to the synchronous state switching of large cortical neuron ensembles between depolarized "up" states and hyperpolarized "down" states (i.e., burst firing).[3] At the scalp sensor level, these oscillations are traditionally quantified through slow wave activity (SWA)—EEG relative power in the 0.5-4 Hz frequency band.[4] SWA is a known marker of sleep need, and its dissipation is homeostatically regulated.[5]

Enhancement of SWA has recently emerged as a promising strategy to improve natural sleep and treat sleep disorders using electrical, magnetic and acoustic modalities.[6-8] The impact of these interventions on clinical outcomes is an active area of investigation. These findings have raised the possibility of accelerating the decay of sleep pressure, enhancing memory consolidation and improving autonomic, neuroendocrine and immune function.[9-13] Considering the substantial safety advantages of using sound, acoustic stimulation has recently emerged as the preferred method to enhance sleep slow oscillations in the ambulatory setting.[9-14] This approach depends on the real-time processing of EEG signals and on the precise delivery of auditory stimulation in relation to the phase of oscillations. Over the last decade, multiple algorithms have been developed to synchronize bursts of pink noise in-phase with the upslope of slow oscillations. Pink noise, also known as 1/f noise (denoting its power density), is random noise that has equal energy per octave. Acoustic stimuli with this spectral distribution are hypothesized to transduce through the vestibulocochlear nerve and ascending non-lemniscal pathway, with diffuse recruitment of cortical neurons. Synchronized depolarization cycles follow a slow oscillatory profile reflected by subsequent augmentation in SWA in the scalp EEG.[15] Conversely, anti-phase stimulation (i.e., acoustic stimuli synchronized with the downslope of slow waves) has been shown to be disruptive, as inferred by decrements in SWAB. Thus, precisely timed auditory stimulation can either potentiate or undermine the manifestation of EEG slow wave oscillations.

Enhancement of EEG Slow Oscillations During Sedation

Among sedatives used in clinical practice, dexmedetomidine is posited to induce states most akin to N3 sleep.[16] An adrenergic alpha-2 agonist, dexmedetomidine primarily induces slow waves and sedation by inhibiting the release of norepinephrine from the locus coeruleus, thus allowing the ventrolateral preoptic nucleus to inhibit ascending arousal circuits.[17] This is in contrast to the majority of anesthetics that induce slow waves by potentiating the gamma aminobutyric acid (GABA)-A receptor.[18] The EEG scalp topography of dexmedetomidine sedation has been described using high-density recordings[19,20]; however cortical and subcortical source localization have not yet been undertaken. The behavioral phenotype of dexmedetomidine sedation resembles that of N3 sleep, characterized by rousability, intact spontaneous respirations, and hemodynamic stability.[21] These properties have made dexmedetomidine a popular sedative in the critical care setting. As with natural sleep, SWA correlates with level of unconsciousness during sedation.[22,23] Nonetheless, important mechanistic differences between dexmedetomidine sedation and natural sleep exist, and their relationship remains an area of active investigation.[24]

Despite a rapidly growing literature describing phase-locked acoustic enhancement of slow oscillations during natural sleep, the effects of this intervention on slow oscillations during sedation remain unknown. From a scientific perspective, differential effects of acoustic stimulation during sleep and sedation may shed light on distinct underlying mechanisms and the relationships between these states. Moreover, for EEG slow waves occurring during dexmedetomidine sedation, estimation of sources and effects on sleep homeostasis remain poorly characterized. From a clinical perspective, non-pharmacologic enhancement of slow oscillations during sedation would have important implications. Considering the relationship of SWA with level of unconsciousness 25, it may be feasible to use lower drug doses to achieve similar brain states and behavioral phenotypes. This would be particularly useful when deeper states of sedation are needed, infusion rates are limited by side effects (e.g., bradycardia or respiratory depression), and poor physiologic reserve or hemodynamic instability limit dose escalation. Improvements in sleep quality and dissipation of sleep pressure using dexmedetomidine and CLASS may also have positive effects on clinical outcomes in intensive care units. Further, reduced exposure to anesthetic agents through neurostimulation may reduce the incidence and severity of post-operative complications and neurocognitive disorders. To this end, a recent randomized controlled trial described the use of low frequency auditory binaural beats and visual stimulation to decrease the cumulative propofol dose administered to pediatric patients during sedation for sub-umbilical surgery.[26] EEG signals were not specifically investigated other than reporting a non-significant effect on the bispectral index (BIS).

In summary, closed-loop acoustic stimulation can enhance EEG slow oscillations during natural sleep, but whether auditory stimuli can enhance slow oscillations during sedation has not yet been studied. Acoustic enhancement of slow oscillations could provide clinicians with a non-pharmacological adjunct to augment thresholds for arousal, with potential translation toward improved clinical outcomes in the perioperative and critical care settings.

Objectives and Specific Aims

The primary objective of this study is to determine if phase-locked acoustic stimulation can enhance EEG slow wave expression during sedation with dexmedetomidine. Secondary objectives are to characterize dexmedetomidine slow waves with and without CLASS using high-density EEG, and to measure their downstream effects on behavior, arousal, and sleep. The corresponding objectives are as follows:

Objective 1: Determine whether dexmedetomidine-induced EEG slow waves can be potentiated with CLASS.

Objective 2: Assess whether performance of a behavioral task during dexmedetomidine sedation is modulated by CLASS.

Objective 3: Assess whether thresholds for responsiveness to peripheral thermal stimulation during dexmedetomidine sedation are modulated by CLASS.

Objective 4: Assess whether CLASS with dexmedetomidine reduces metrics of slow wave need on the night of the intervention.

Objective 5: Compare modeled source localization of dexmedetomidine-induced EEG slow waves recorded in the presence and absence of CLASS.

Methods and Analysis

Study Design

Figure 12:
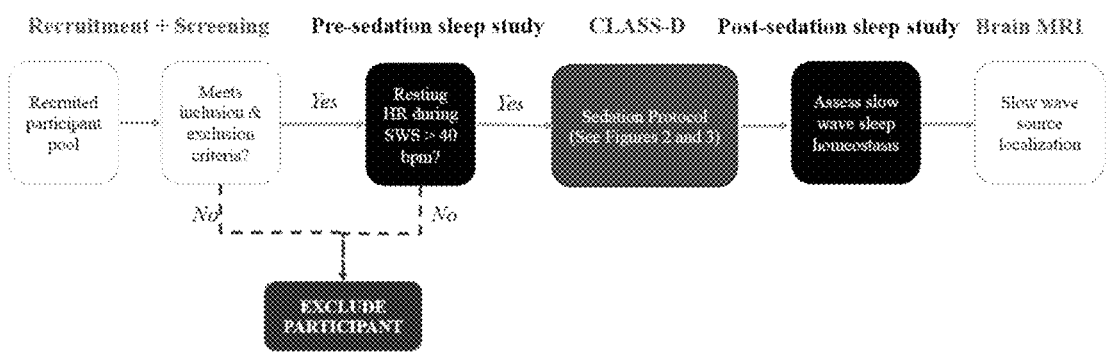
FIG. 12. Longitudinal Study Design. After being recruited, participants will be evaluated at the medical center. If they meet inclusion and exclusion criteria, they will be trained on how to use the Dreem device and record sleep EEG data a night prior to undergoing sedation. Participants will record sleep EEG data on the night following sedation. A non-contrast structural brain magnetic resonance imaging (MRI) scan will then be completed at a later date.

CLASS-D is a prospective, within-subject, crossover, controlled, interventional trial. For each participant, study participation will focus on a single session of dexmedetomidine sedation flanked by ambulatory sleep studies targeting pre- and post-sedation sleep structure (FIG. 12). The study design will allow investigators to compare the effects of three acoustic stimulation conditions on EEG slow waves in the same brain, at the same time of day, and at the same plasma concentration of dexmedetomidine. The three conditions are: in-phase stimulation (pink noise bursts synchronized to the upslope of slow waves), anti-phase stimulation (pink noise bursts synchronized to the downslope of slow waves), and sham stimulation (volume set to zero dB) (FIG. 13). Washout periods of acoustic silence will be used during the stimulation protocol to control for short-term resonant effects of acoustic stimulation. The rate of dexmedetomidine infusion will be adjusted throughout the experiment to maintain stable plasma concentrations, with post-hoc assessment of plasma levels.

Study Procedures and Data Acquisition

Recruitment and Baseline Testing

Participants will be recruited using posted fliers, internet advertisements and university volunteer databases. Prior to enrollment, participants will undergo a phone interview to screen for inclusion and exclusion criteria (TABLE 3).

TABLE 3. Inclusion & Exclusion Criteria for CLASS-D. Participants will be screened for inclusion and exclusion criteria at the original recruitment interview and on the day of sedation.

| Inclusion Criteria | Exclusion Criteria |
| --- | --- |
| 18-40 years old<br>ASA Physical<br>Status 1-2 | Diagnosed sleep disorders<br>Habitually short sleeper<br>Use of psychoactive medication<br>Diagnosed psychiatric disorder<br>Diagnosed hearing disorder<br>Neck circumference >40 cm<br>BMI >30<br>Recreational drug or nicotine use<br>Pregnant or nursing female<br>Resting HR <40 bpm during SWS<br>QST pain threshold >50° C. |

Two days prior to the planned sedation session, informed consent will be obtained, and each participant will complete a battery of questionnaires to assess his/her overall health and sleep quality.

Quantitative Sensory Testing

Each participant will then undergo training by a research coordinator in quantitative sensory testing (QST). Each participant's baseline heat pain threshold (HPT) and heat pain tolerance threshold (HPTT) will be measured with a Thermal Sensory Analyzer (TSA-11, Medoc, Israel) using the method of limits as defined in the German Research Network on Neuropathic Pain's seminal paper describing standardized protocols and reference values.[27] Specifically, the TSA-II device will be applied to the participant's non-dominant volar forearm. The contact area of the thermode is 9 cm$^2$, and the baseline temperature is 32° C. Thresholds will be obtained from responses to a ramped thermal stimulation (1° C./s). HPT will be measured by asking the participant to press the button when the sensation of heat transitions to a feeling of pain. HPTT will be measured by asking the participant to press the button when they can no longer tolerate the heat pain. Each threshold (i.e., HPT and HPTT) will be measured four times, and the mean of the last three values will be averaged to compute the threshold. The maximal temperature that can be applied using the TSA-II device is 52° C., and the maximal thermal energy delivered using this ramping protocol is three orders of magnitude lower than what is required to induce tissue injury[28]. The skin site used in testing will be marked for future investigation. Participants with baseline HPTT>50° C. will be assessed at a different location on the non-dominant upper extremity. Persistently elevated HPTT>50° C. will lead to exclusion from the study. Participants who demonstrate an inability to provide consistent QST responses during pre-screening be excluded from this study.

Ambulatory Sleep Recording

Each participant will then be provided with a Dreem device[14][29][30], a device designed and validated to record sleep in the home environment.[14] The device includes frontal and occipital EEG, as well as pulse plethysmography and accelerometry. Participants will receive instructions on using the device to record ambulatory sleep studies. On the night prior to sedation, each participant will wear the device and physiological data will be recorded (i.e., pre-sedation sleep). To assess the effect of CLASS and dexmedetomidine sedation on subsequent nocturnal sleep architecture, participants will wear the device on the night following sedation (post-sedation sleep). Participants will also be asked to continuously wear an actigraph watch on their non-dominant arm on the days preceding and following the sedation session to objectively measure circadian rhythms and reproducibility of sleep duration. Participants will receive standard pre-sedation fasting instructions (nil by mouth for 2 hours for clears, 4 hours for liquids, 6 hours for meals) for the dexmedetomidine sedation session.

Pre-Sedation Procedures

A target-controlled infusion (TCI) of dexmedetomidine based on validated pharmacokinetic models will be used to achieve stable plasma concentrations during this study.[22][23][31-33] The target-controlled infusion syringe pump is controlled by Rugloop II©, a Windows® based target controlled infusion and data management program. Prior to each sedation session, Rugloop II will be used to simulate the sedation session for each possible targeted concentration (i.e., 2, 3, and 4 ng/ml). The individualized drug administration simulation will be reviewed by a board-certified anesthesiologist prior to the sedation session. For use in the critical care setting, the manufacturer's label suggests a dexmedetomidine loading dose regimen of 6 mcg/kg/hr for 10 minutes, followed by lower maintenance infusion rates.[34] The default maximal infusion rate for dexmedetomidine in Rugloop II is 6 mcg/kg/hr, consistent with previous volunteer studies.[19][31][32] These precautions are primarily in place to minimize the risk of hypotension and bradycardia. Phenylephrine and glycopyrrolate will be used to treat hemodynamic effects of dexmedetomidine at the discretion of the attending anesthesiologist.

On the day of the scheduled sedation, the research team will re-administer the screening questionnaire to ensure that the participant still meets the inclusion/exclusion criteria. The ambulatory sleep study will be reviewed. Staff will ensure that the participant has adhered to American Society of Anesthesiologists (ASA) fasting guidelines for sedation/general anesthesia. Pre-sedation sleepiness will be assessed using the Stanford Sleepiness Scale.[35]

The sedation protocol will be completed in a location equipped with standard monitoring, airway equipment, suction, and a dedicated board-certified anesthesiologist, per standard of practice guidelines for anesthesia care.[36] Each participant will have two intravenous catheters (IV) placed, one to receive medications and fluid throughout the study protocol, and another to draw blood samples. Standard ASA monitors will be applied: electrocardiogram, non-invasive blood pressure, pulse oximeter, and breathing rate monitors. Participants will also have a high-density 65-electrode EEG scalp electrode net (MagStim) applied with Elefix conductive gel (Nihon Kohden) injected within sensors. Additionally, three shielded electrodes will be affixed to the scalp and connected to the custom-made CLASS device: one active electrode, one reference electrode, and one ground electrode. The CLASS device consists of EEG amplifiers, a circuit board, a sound card, a visual display, and a battery, all shielded in a metal case and connected to a separate computer for software interfacing running custom Labview software described below. The device amplifies EEG input, tracks the phase of a specified central frequency in the band-passed signal, and synchronizes audio output to the phase specified by the investigators.

Following application of all monitors, a QST will be performed to measure HPT and HPTT at the non-dominant forearm site used in previous testing. If HPTT is not greater than 50° C., the area will be marked. If HPTT is greater than 50° C., the test will be repeated at a different location on the non-dominant forearm and repeated until the HPTT is found to be less than 50° C. The final location will then be marked, and all subsequent QST measurements will be made at this location. EEG data will be recorded during HPPT testing.

Figure 14:
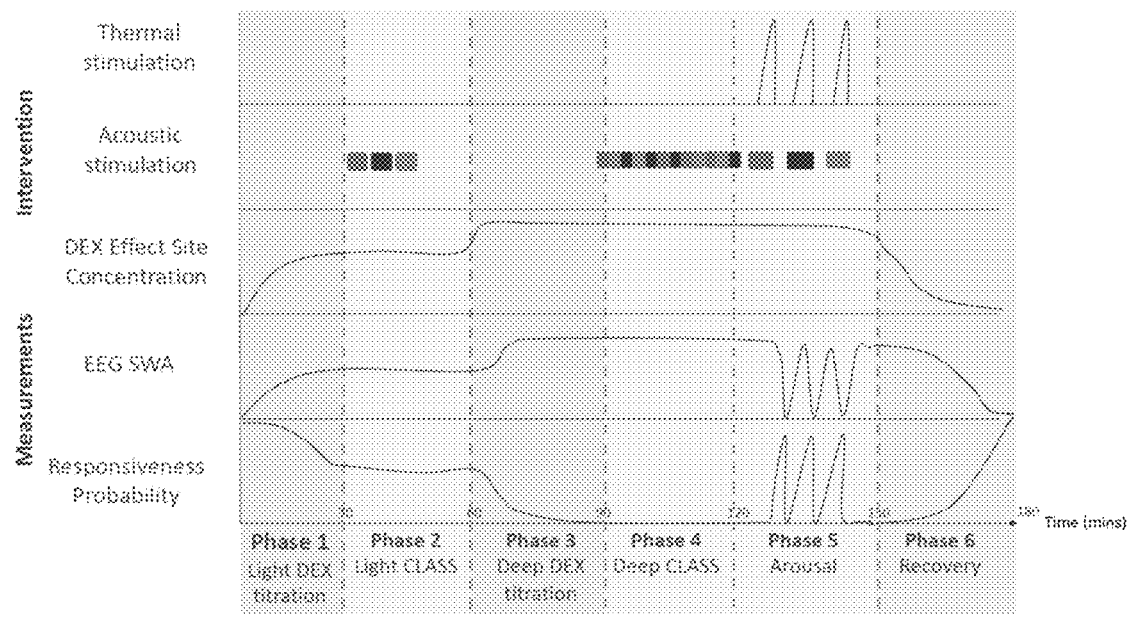
FIG. 14. Sedation Protocol. The sedation protocol consists of six phases. In Phase 1, dexmedetomidine will be escalated using TCI, causing a subsequent increase in slow wave activity (SWA) and impairments in the behavioral task. During Phase 2, responsive participants showing EEG slow waves will be presented with CLASS conditions while they are still performing the behavioral task. Upon entry into Phase 3, dexmedetomidine will be further escalated to achieve loss of behavioral responsiveness. Phase 4 represents the core of the experiment. Participants unresponsive and demonstrating EEG slow waves will be presented with multiple blocks of CLASS conditions during a stable dexmedetomidine effect site concentration. Targeting of this dexmedetomidine concentration will be continued during Phase 5. Participants will be aroused three times by thermal stimulation during CLASS. In Phase 6, the dexmedetomidine infusion will stop and resting EEG will be recorded as participants recover full responsiveness during the behavioral task. Blue, black, and orange squares represent in-phase, antiphase, and sham conditions, respectively. The order of CLASS conditions will be randomized across participants.

Participants will be instructed to perform a validated behavioral task throughout the protocol[37] by complying with the following instruction during eyes closure: "Squeeze the dynamometer during inspiration and release it during expiration". Participants will be considered responsive whenever they perform the task consistently (at least five consecutive correct squeezes), and unresponsive after five consecutive failures to squeeze during inspiration. State-space models will also be used to assess loss and return of responsiveness offline.[38] After confirming adequate comprehension, 10 minutes of baseline awake EEG measurements will be recorded: five minutes with eyes open and five minutes with eyes closed. After completing all questionnaires and baseline recordings, and ensuring that all monitors are functional, the sedation protocol will begin (FIG. 14). The protocol can be broadly separated into six phases: Phase 1, light dexmedetomidine titration; Phase 2, light CLASS; Phase 3, deep dexmedetomidine titration; Phase 4, deep CLASS; Phase 5, arousal; and Phase 6, recovery. All phases will be recorded using a video camera. TABLE 4 outlines the alignment of experimental phases and study objectives. Aims 1, 2 and 3 will be directly tested during the sedation protocol. Objective 4 will be completed using the sleep studies on nights preceding and following the sedation protocol. Objective 5 will be addressed by combining analysis of EEG data from the sedation protocol with a structural brain MRI acquired at a later date.

TABLE 4

CLASS-D Phases and Objectives.

| Phase # | Condition | Aims |
|---|---|---|
| Phase 0 | Pre-sedation sleep study | Assess effects of CLASS on sleep (Objective 4) |
| Phase 1 | Light DEX titration | Induce EEG slow waves |
| Phase 2 | Light CLASS | Test effects of CLASS on behavior (Objective 2) |
| Phase 3 | Deep DEX titration | Induce loss of behavioral responsiveness |
| Phase 4 | Deep CLASS | Test effects of CLASS on slow waves (Objectives 1 and 5) |
| Phase 5 | Arousal | Test effects of CLASS on arousal thresholds (Objective 3) |
| Phase 6 | Recovery | Drug elimination, transition to waking state |
| Phase 7 | Post-sedation sleep study | Assess effects of CLASS on sleep (Objective 4) |

Phase 1: Light Dexmedetomidine Titration

Figure 15:
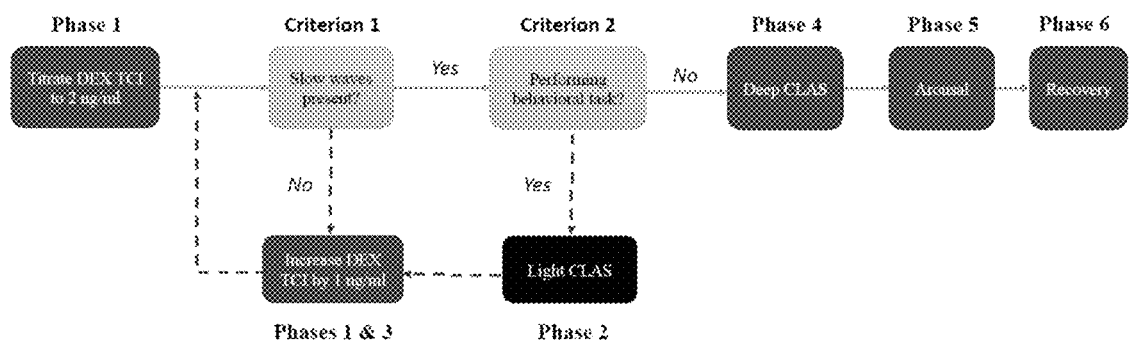
FIG. 15. Decision Tree During Sedation Protocol. In all cases, the sedation protocol will begin with the targeting of effect site and plasma dexmedetomidine concentrations of 2 ng/ml via TCI. In the event that slow waves are not observed in the EEG, the target concentration will be increased in increments of 1 ng/ml to induce EEG slow waves. If a participant with slow waves continues to perform the behavioral task, they will proceed to light CLASS, after which the dexmedetomidine TCI is increased in increments of 1 ng/ml until they stop performing the task. This is followed by the deep CLASS, arousal, and recovery phases.

The participant will be instructed to close his/her eyes and perform the behavioral instruction: "Squeeze the dynamometer during inspiration and release it during expiration". An initial target concentration of 2 ng/ml will be entered into Rugloop and the infusion will begin. Once the predicted plasma site concentrations of dexmedetomidine have reached 2 ng/ml, two criteria will be assessed to determine if the experiment will progress to the light or deep acoustic stimulation phase (FIG. 15). The first criterion is behavioral: investigators will assess if the participant is still performing the task of squeezing as device in their dominant hand during inspiration. The second criterion is electrophysiological: investigators will visually assess for the presence of large amplitude (>20 microvolts) EEG slow waves. The physicians assessing the EEG will have completed accredited training in the interpretation of human EEG during sedation and anesthesia.[39,40] If the participant demonstrates the presence of EEG slow waves (Criterion 1) and is still performing the behavioral task (Criterion 2), the experiment will proceed to light CLASS (Phase 2). Alternatively, if the participant loses behavioral responsiveness before or concurrent with the appearance of EEG slow waves, then the experiment will proceed directly to deep CLASS (Phase 4), bypassing Phases 2 and 3.

Phase 2: Light CLASS

Custom scripts in Labview will track the phase of slow EEG oscillations and trigger binaural delivery of acoustic stimuli, phase-locked to a central frequency of 1 Hz. The stimuli will be delivered via noise-isolating earphones as bursts of pink 1/f noise of 50 ms duration with a 5 ms rising and falling time, identical to those used in previous sleep studies.[8,41] Sound volume will be calibrated to 65 dB using a sound level meter and adjusted for each participant to minimize the risk of arousing them with sound. Each participant will be presented with the three CLASS conditions as they perform the behavioral task in a sedated state: five minutes of in-phase CLASS, five minutes of anti-phase CLASS, and five minutes of sham (FIG. 14). The order of CLASS conditions will be balanced across participants to account for lasting resonant effects beyond termination of condition. A one-minute period of silence will also separate each condition as an additional washout period. When possible, assessors of behavioral responses will be blinded to CLASS conditions.

Phase 3: Deep Dexmedetomidine Titration

The dexmedetomidine TCI will be increased in increments of 1 ng/ml to achieve loss of behavioral responsiveness after which a sample acoustic stimulation train will be delivered to ensure that the participant is not roused by the sound. A conservative estimate for the equilibration constant ($t_{1/2}$ $k_{e0}$) of dexmedetomidine in healthy volunteers is 3 minutes.[42] Therefore, 15 minutes (i.e., $5 \times t_{1/2}$ $k_{e0}$) will be allowed to pass before drawing venous samples for quantitation of dexmedetomidine plasma concentration, and beginning Phase 4.

Phase 4: Deep CLASS

The acoustic stimuli delivered during Phase 4 are the same as those described in Phase 2. The volume will be reduced if it arouses the participant. The fundamental differences between phase 2 and phase 4 are threefold: (1) Dexmedetomidine concentrations are higher; (2) Participants are unresponsive; and (3) Each participant is exposed to each CLASS condition four times (FIG. 14). The order of the conditions for all participants is pre-determined prior to recruitment and balanced across participants to account for carry-over effects. Similar to Phase 2, one minute of washout silence will separate each CLASS condition.

Phase 5: Thermal Arousal

Participants will undergo three arousals during this phase of the experiment: one during in-phase stimulation, one during anti-phase stimulation, and one during sham stimulation (FIG. 13). The order of CLASS conditions under which a participant will be aroused is the same as in Phase 2, which is balanced across participants. Each arousal will be preceded by at least three consecutive minutes of acoustic stimulation, which will continue during the arousal procedure. The arousal procedure consists of the same ramping thermal stimulation used during pre-sedation QST. The cardinal difference between pre-sedation QST and arousal QST is that one of the investigators will be tasked with pressing the button to end the thermal ramp instead of the sedated participant. The investigator will end the arousal protocol as soon as they observe purposeful behavior in response to the thermal stimulation. The investigator will also be able to terminate the thermal stimulation at their clinical discretion. Vital signs, EEG, and video recording will allow review of the time of arousal during post-hoc analysis. EEG changes reflective of arousal during dexmedetomidine sedation consist of decreasing delta and alpha power[22]. Assessors of arousal will be blinded to the acoustic stimulation conditions. Once a participant has been definitively aroused, thermal stimulation will cease. The participant will then be asked to rate pain on a visual analog scale, and a 15-minute washout period will ensue without any thermal or acoustic stimulation. Based on a recent investigation by Sleigh and colleagues[22], we expect participants to return to a state of unresponsiveness within 60 seconds, and for EEG SWA to return to pre-arousal levels within 10 minutes. This protocol will be repeated three times, once for each stimulation condition. The predicted plasma concentration of dexmedetomidine will be maintained by TCI throughout the acoustic stimulation and arousal phases of the experiment. After the third arousal and washout period, a second 5 ml venous blood sample will be drawn for quantitation of dexmedetomidine concentration and placed on ice for processing. The dexmedetomidine infusion rate will then be set to zero, and the recovery phase will begin.

Phase 6: Recovery

All physiological monitoring will continue and behavioral recovery will be measured with the same paradigm used during Phase 1. The participant will continue to be monitored by staff until they meet standard discharge criteria following sedation, including recovery of baseline cognitive and physiologic functions.[43] A post-sedation questionnaire will then be administered to assess the participant's memories of the experiment. The Stanford Sleepiness Scale will also be re-administered. The participant will then be discharged home with the Dreem device to assess structure of sleep on the night of the study. They will also receive standard post-sedation discharge instructions and be accompanied home by a trustworthy person of their choosing, selected before sedation.

Dexmedetomidine Plasma Concentrations

To corroborate and correct the predicted plasma concentrations of dexmedetomidine, 3 ml venous blood samples will be collected twice during the experiment: the first immediately preceding phase 4 and the second immediately preceding phase 6. Samples will be drawn from the IV not in use for infusing dexmedetomidine. Plasma dexmedetomidine levels will be measured from samples using a validated liquid chromatography-mass spectrometry assay at a specialized laboratory.

Post-Sedation Sleep and MRI

Participants will be instructed to wear the Dreem and record data during overnight sleep on the night following the sedation protocol. They will return the device the following day and complete a final sleep questionnaire and sleepiness assessment. Participants will also be scheduled for non-contrast brain MRI at a later date. The anatomical data obtained from the individual brain MRI will be used for source localization of EEG slow waves, using Brainstorm[44].

EEG Processing and Analyses

Processing of EEG data will be performed using custom-written MATLAB scripts and EEGLAB.[45] These steps will include 0.1-50 Hz bandpass filtering, temporal downsampling to 250 Hz, visual rejection of bad channels, spherical spline interpolation, and re-referencing to the global average. Peaks of slow waves will be automatically identified using automated multiscale peak detection.[46] Measures of slow wave activity (SWA) and cumulative slow wave activity (cSWA)[9] will be derived from the power in the 0.5-4 Hz frequency band. Amplitude of individual slow waves, slope and duration of slow wave trains will be computed. Sleep homeostasis during pre- and post-sedation sleep will be assessed via changes in EEG SWA and slow wave features between the first and last sleep cycles of the night, as well as cSWA for the entire night.[9,13,47]

Statistical Analysis

A linear mixed effects model will be used to compare primary outcome measures across the three conditions. The model will include time and condition (sham, in-phase, and anti-phase stimulation) as fixed effects and account for age and sex. Dependent variables will include amplitude and duration of slow waves. Paired t-tests or U-tests along with appropriate confidence intervals will be used to compare measures of sleep homeostasis between pre- and post-sedation sleep (depending on normality of measures). Permutation tests will allow comparisons of source estimation models. Logistic regression modelling of responsiveness to thermal stimulation will be used to compare arousal thresholds during in-phase vs. anti-phase vs. sham stimulation.

A convenience sample size of 20 participants will be used for this study. Previous volunteer studies investigating closed-loop acoustic stimulation during sleep have used sample sizes of 11-28 participants to detect changes in SWA of 10-40%.[9-13] Based on prior studies involving sedation with sevoflurane[48], ketamine[49], and isoflurane[50], we expect an attrition rate of 25%, leaving 14-15 participants with interpretable data. Based on this literature, we conservatively expect this experiment to be powered to detect a within-subject change in SWA of 15%, with an alpha of 0.05 and beta of 0.8.[51]

Conclusion

This investigation will elucidate 1) the potential of exogenous stimulation to potentiate SWA during sedation; 2) the physiologic significance of this intervention; and 3) the connection between EEG slow waves observed during sleep and sedation.

Abbreviations

ASA: American Society of Anesthesiologists
CLAS: Closed-loop acoustic stimulation
CLASS: Closed-loop acoustic stimulation during sedation
CLASS-D: Closed-Loop Acoustic Stimulation during Sedation with Dexmedetomidine
DEX: Dexmedetomidine
EEG: Electroencephalogram
GABA: Gamma aminobutyric acid
HPT: Heat pain threshold
HPTT: Heat pain tolerance threshold
IV: Intravenous
N3: Non-rapid eye movement sleep Stage 3
NREM: Non-rapid Eye Movement
QST: quantitative sensory testing
SWA: slow wave activity
TCI: target-controlled infusion

REFERENCES

1. Prerau M J, Brown R E, Bianchi M T, et al. Sleep Neurophysiological Dynamics Through the Lens of Multitaper Spectral Analysis. *Physiology (Bethesda)* 2017; 32(1):60-92. doi: 10.1152/physiol.00062.2015 [published Online First: 2016/12/09]
2. Leger D, Debellemaniere E, Rabat A, et al. Slow-wave sleep: From the cell to the clinic. *Sleep Med Rev* 2018; 41:113-32. doi: 10.1016/j.smrv.2018.01.008 [published Online First: 2018/03/02]
3. Neske G T. The Slow Oscillation in Cortical and Thalamic Networks: Mechanisms and Functions. *Front Neural Circuits* 2015; 9:88. doi: 10.3389/fncir.2015.00088 [published Online First: 2016/02/03]
4. Greene R W, Frank M G. Slow wave activity during sleep: functional and therapeutic implications. *Neuroscientist* 2010; 16(6):618-33. doi: 10.1177/1073858410377064 [published Online First: 2010/10/06]
5. Borbely A A. A two process model of sleep regulation. *Hum Neurobiol* 1982,1(3):195-204. [published Online First: 1982/01/01]
6. Marshall L, Helgadottir H, Molle M, et al. Boosting slow oscillations during sleep potentiates memory. *Nature* 2006,444(7119):610-3. doi: 10.1038/nature05278 [published Online First: 2006/11/07]
7. Massimini M, Ferrarelli F, Esser S K, et al. Triggering sleep slow waves by transcranial magnetic stimulation. *Proc Natl Acad Sci USA* 2007,104(20):8496-501. doi: 10.1073/pnas.0702495104 [published Online First: 2007/05/08]
8. Ngo H V, Martinetz T, Born J, et al. Auditory closed-loop stimulation of the sleep slow oscillation enhances memory. *Neuron* 2013,78(3):545-53. doi: 10.1016/j.neuron.2013.03.006 [published Online First: 2013/04/16]
9. Garcia-Molina G, Tsoneva T, Jasko J, et al. Closed-loop system to enhance slow-wave activity. *J Neural Eng*

2018,15(6):066018. doi: 10.1088/1741-2552/aae18f [published Online First: 2018/09/15]

10. Besedovsky L, Ngo H V, Dimitrov S, et al. Auditory closed-loop stimulation of EEG slow oscillations strengthens sleep and signs of its immune-supportive function. *Nat Commun* 2017,8(1):1984. doi: 10.1038/s41467-017-02170-3 [published Online First: 2017/12/08]

11. Leminen M M, Virkkala J, Saure E, et al. Enhanced Memory Consolidation Via Automatic Sound Stimulation During Non-REM Sleep. *Sleep* 2017; 40(3) doi: 10.1093/sleep/zsx003 [published Online First: 2017/04/02]

12. Papalambros N A, Santostasi G, Malkani R G, et al. Acoustic Enhancement of Sleep Slow Oscillations and Concomitant Memory Improvement in Older Adults. *Front Hum Neurosci* 2017; 11:109. doi: 10.3389/fnhum.2017.00109 [published Online First: 2017/03/25]

13. Grimaldi D, Papalambros N A, Reid K J, et al. Strengthening sleep-autonomic interaction via acoustic enhancement of slow oscillations. *Sleep* 2019 doi: 10.1093/sleep/zsz036 [published Online First: 2019/02/13]

14. Debellemaniere E, Chambon S, Pinaud C, et al. Performance of an Ambulatory Dry-EEG Device for Auditory Closed-Loop Stimulation of Sleep Slow Oscillations in the Home Environment. *Front Hum Neurosci* 2018; 12:88. doi: 10.3389/fnhum.2018.00088 [published Online First: 2018/03/24]

15. Bellesi M, Riedner B A, Garcia-Molina G N, et al. Enhancement of sleep slow waves: underlying mechanisms and practical consequences. *Front Syst Neurosci* 2014; 8:208. doi: 10.3389/fnsys.2014.00208 [published Online First: 2014/11/13]

16. Akeju O, Hobbs L E, Gao L, et al. Dexmedetomidine promotes biomimetic non-rapid eye movement stage 3 sleep in humans: A pilot study. *Clin Neurophysiol* 2018, 129(1):69-78. doi: 10.1016/j.clinph.2017.10.005 [published Online First: 2017/11/21]

17. Brown E N, Lydic R, Schiff N D. General anesthesia, sleep, and coma. *N Engl J Med* 2010,363(27):2638-50. doi: 10.1056/NEJMra0808281 [published Online First: 2010/12/31]

18. Purdon P L, Sampson A, Pavone K J, et al. Clinical Electroencephalography for Anesthesiologists: Part I: Background and Basic Signatures. *Anesthesiology* 2015, 123(4):937-60. doi: 10.1097/ALN.0000000000000841 [published Online First: 2015/08/15]

19. Akeju O, Kim S E, Vazquez R, et al. Spatiotemporal Dynamics of Dexmedetomidine-Induced Electroencephalogram Oscillations. *PLoS One* 2016,11(10):e0163431. doi: 10.1371/journal.pone.0163431 [published Online First: 2016/10/07]

20. Xi C, Sun S, Pan C, et al. Different effects of propofol and dexmedetomidine sedation on electroencephalogram patterns: Wakefulness, moderate sedation, deep sedation and recovery. *PLoS One* 2018; 13(6):e0199120. doi: 10.1371/journal.pone.0199120 [published Online First: 2018/06/20]

21. Ebert T J, Hall J E, Barney J A, et al. The effects of increasing plasma concentrations of dexmedetomidine in humans. *Anesthesiology* 2000; 93(2):382-94. [published Online First: 2000/07/26]

22. Sleigh J W, Vacas S, Flexman A M, et al. Electroencephalographic Arousal Patterns Under Dexmedetomidine Sedation. *Anesth Analg* 2018,127(4):951-59. doi: 10.1213/ANE.0000000000003590 [published Online First: 2018/06/23]

23. Scheinin A, Kallionpaa R E, Li D, et al. Differentiating Drug-related and State-related Effects of Dexmedetomidine and Propofol on the Electroencephalogram. *Anesthesiology* 2018,129(1):22-36. doi: 10.1097/ALN.0000000000002192 [published Online First: 2018/04/12]

24. Guldenmund P, Vanhaudenhuyse A, Sanders R D, et al. Brain functional connectivity differentiates dexmedetomidine from propofol and natural sleep. *Br J Anaesth* 2017,119(4):674-84. doi: 10.1093/bja/aex257 [published Online First: 2017/11/10]

25. Ni Mhuircheartaigh R, Warnaby C, Rogers R, et al. Slow-wave activity saturation and thalamocortical isolation during propofol anesthesia in humans. *Sci Transl Med* 2013; 5(208):208ra148. doi: 10.1126/scitranslmed.3006007 [published Online First: 2013/10/25]

26. Schmid W, Marhofer P, Opfermann P, et al. Brainwave entrainment to minimise sedative drug doses in paediatric surgery: a randomised controlled trial. *Br J Anaesth* 2020 doi: 10.1016/j.bja.2020.05.050 [published Online First: 2020/07/13]

27. Rolke R, Baron R, Maier C, et al. Quantitative sensory testing in the German Research Network on Neuropathic Pain (DFNS): standardized protocol and reference values. *Pain* 2006,123(3):231-43. doi: 10.1016/j.pain.2006.01.041 [published Online First: 2006/05/16]

28. Yarmolenko P S, Moon E J, Landon C, et al. Thresholds for thermal damage to normal tissues: an update. *Int J Hyperthermia* 2011,27(4):320-43. doi: 10.3109/02656736.2010.534527 [published Online First: 2011/05/20]

29. Arnal P J, Thorey V, Ballard M E, et al. The Dreem Headband as an Alternative to Polysomnography for EEG Signal Acquisition and Sleep Staging. *BioRxiv* 2019: 662734.

30. Andrillon T, Solelhac G, Bouchequet P, et al. Revisiting the value of polysomnographic data in insomnia: more than meets the eye. *Sleep Medicine* 2020; 66:184-200. doi: 10.1016/j.sleep.2019.12.002

31. Hannivoort L N, Eleveld D J, Proost J H, et al. Development of an Optimized Pharmacokinetic Model of Dexmedetomidine Using Target-controlled Infusion in Healthy Volunteers. *Anesthesiology* 2015,123(2):357-67. doi: 10.1097/ALN.0000000000000740 [published Online First: 2015/06/13]

32. Colin P J, Hannivoort L N, Eleveld D J, et al. Dexmedetomidine pharmacodynamics in healthy volunteers: 2. Haemodynamic profile. *Br J Anaesth* 2017; 119(2):211-20. doi: 10.1093/bja/aex086 [published Online First: 2017/09/01]

33. Colin P J, Hannivoort L N, Eleveld D J, et al. Dexmedetomidine pharmacokinetic-pharmacodynamic modelling in healthy volunteers: 1. Influence of arousal on bispectral index and sedation. *Br J Anaesth* 2017; 119(2): 200-10. doi: 10.1093/bja/aex085 [published Online First: 2017/09/01]

34. Weerink MAS, Struys M, Hannivoort L N, et al. Clinical Pharmacokinetics and Pharmacodynamics of Dexmedetomidine. *Clin Pharmacokinet* 2017; 56(8):893-913. doi: 10.1007/s40262-017-0507-7 [published Online First: 2017/01/21]

35. Hoddes E, Zarcone V, Smythe H, et al. Quantification of sleepiness: a new approach. *Psychophysiology* 1973,10 (4):431-6. [published Online First: 1973/07/01]

36. Pandya A N, Majid S Z, Desai M S. The Origins, Evolution, and Spread of Anesthesia Monitoring Standards: From Boston to Across the World. *Anesth Analg* 2020 doi: 10.1213/ANE.0000000000005021 [published Online First: 2020/07/16]
37. Prerau M J, Hartnack K E, Obregon-Henao G, et al. Tracking the sleep onset process: an empirical model of behavioral and physiological dynamics. *PLoS Comput Biol* 2014,10(10):e1003866. doi: 10.1371/journal.pcbi.1003866 [published Online First: 2014/10/03]
38. Purdon P L, Pierce E T, Mukamel E A, et al. Electroencephalogram signatures of loss and recovery of consciousness from propofol. *Proc Natl Acad Sci USA* 2013, 110(12):E1142-51. doi: 10.1073/pnas.1221180110 [published Online First: 2013/03/15]
39. Purdon P L, Brown E N. Clinical Electroencephalography for the Anesthesiologist: Partners Healthcare; [Available from: https://www.phscpd.org/activities/activity-detail/clinical-electroencephalography-for-the-anesthesiologist2017.
40. Purdon P L, Colvin C A, Brown E N. EEG For Anesthesia International Anesthesia Research Society: International Anesthesia Research Society; Available from: http://eegforanesthesia.iars.org/2019.
41. Santostasi G, Malkani R, Riedner B, et al. Phase-locked loop for precisely timed acoustic stimulation during sleep. *J Neurosci Methods* 2016; 259:101-14. doi: 10.1016/j.jneumeth.2015.11.007 [published Online First: 2015/12/01]
42. Talke P, Anderson B J. Pharmacokinetics and pharmacodynamics of dexmedetomidine-induced vasoconstriction in healthy volunteers. *Br J Clin Pharmacol* 2018,84 (6):1364-72. doi: 10.1111/bcp.13571 [published Online First: 2018/03/02]
43. Aldrete J A. The post-anesthesia recovery score revisited. *J Clin Anesth* 1995; 7(1):89-91. doi: 10.1016/0952-8180(94)00001-k [published Online First: 1995/02/01]
44. Tadel F, Baillet S, Mosher J C, et al. Brainstorm: a user-friendly application for MEG/EEG analysis. *Comput Intell Neurosci* 2011; 2011:879716. doi: 10.1155/2011/879716
45. Delorme A, Makeig S. EEGLAB: an open source toolbox for analysis of single-trial EEG dynamics including independent component analysis. *J Neurosci Methods* 2004; 134(1):9-21. doi: 10.1016/j.jneumeth.2003.10.009
46. Scholkmann F, Bens J, Wolf M. An Efficient Algorithm for Automatic Peak Detection in Noisy Periodic and Quasi-Periodic Signals. *Algorithms* 2012; 5:588-603. doi: 10.3390/a5040588
47. Riedner B A, Vyazovskiy V V, Huber R, et al. Sleep homeostasis and cortical synchronization: III. A high-density EEG study of sleep slow waves in humans. *Sleep* 2007,30(12):1643-57. [published Online First: 2008/02/06]
48. Palanca B J, Mitra A, Larson-Prior L, et al. Resting-state Functional Magnetic Resonance Imaging Correlates of Sevoflurane-induced Unconsciousness. *Anesthesiology* 2015; 123:346-56. doi: 10.1097/ALN 0.0000000000000731
49. Palanca BJA, Maybrier H R, Mickle A M, et al. Cognitive and Neurophysiological Recovery Following Electroconvulsive Therapy: A Study Protocol. *Front Psychiatry* 2018; 9:171. doi: 10.3389/fpsyt.2018.00171
50. Maier K L, McKinstry-Wu A R, Palanca B J, et al. Protocol for the Reconstructing Human Consciousness and Cognition Study. *Front Hum Neurosci* 2017
51. Casagrande J T, Pike M C. An improved approximate formula for calculating sample sizes for comparing two binomial distributions. *Biometrics* 1978; 34(3):483-6. [published Online First: 1978/09/01]
52. Chan A W, Tetzlaff J M, Gotzsche P C, et al. SPIRIT 2013 explanation and elaboration: guidance for protocols of clinical trials. *BMJ* 2013; 346:e7586. doi: 10.1136/bmj.e7586 [published Online First: 2013/01/11]
53. Chan A W, Tetzlaff J M, Altman D G, et al. SPIRIT 2013 statement: defining standard protocol items for clinical trials. *Ann Intern Med* 2013,158(3):200-7. doi: 10.7326/0003-4819-158-3-201302050-00583 [published Online First: 2013/01/09]

What is claimed is:

1. A method of augmenting, entraining, modulating, enhancing, or maintaining slow-delta waves in a brain of a subject using phase-locked neurostimulation comprising:
   (i) administering at least one pharmacological agent to the subject, wherein the at least one pharmacological agent comprises a slow-delta wave enhancing agent capable of inducing an endogenous pharmaceutically-induced slow-delta wave in the brain of the subject;
   (ii) performing an electroencephalogram (EEG) on the subject having the endogenous pharmaceutically-induced slow-delta wave and measuring an electrical signal of the endogenous pharmaceutically-induced slow-delta wave that originates in the brain of the subject; and
   (iii) applying a phase-locked neurostimulation to the subject based on the measured electrical signal of the endogenous pharmaceutically-induced slow-delta wave, wherein applying the phase-locked neurostimulation comprises applying a closed-loop neurostimulation that synchronizes the neurostimulation to a peak of the endogenous pharmaceutically-induced slow-delta wave, resulting in an in-phase neurostimulated slow-delta wave electrical signal.

2. The method of claim 1, wherein the phase-locked neurostimulation comprises synchronization of the neurostimulation to:
   an up-slope of the endogenous pharmaceutically-induced slow-delta wave, if the neurostimulation is a first neurostimulation following the administering of the at least one pharmacological agent, or
   the in-phase neurostimulated slow-delta wave, if the neurostimulation is subsequent to the first neurostimulation.

3. The method of claim 1, wherein the phase-locked neurostimulation comprises: (a) calculating a set of one or more estimates of instantaneous phase and instantaneous amplitude of the endogenous pharmaceutically-induced slow-delta wave electrical signal or the in-phase neurostimulated slow-delta wave electrical signal; and (b) controlling, based on the set of one or more estimates, timing of one or more changes in the neurostimulation.

4. The method of claim 3, wherein each estimate in the set of one or more estimates is calculated based on a specific sample in a specific sample window of the measured electrical signal, wherein:
   (a) the specific sample window is different than that for any other estimate in the set; and
   (b) the specific sample is more recent than any other sample in the specific sample window.

5. The method of claim 4, wherein, for each estimate in the set of estimates of instantaneous phase and instantaneous amplitude, the calculating comprises performing an inverse discrete Fourier transform that reconstructs the specific sample, wherein the specific sample is in the specific sample window and is more recent than the other sample in the specific sample window.

6. The method of claim 3, wherein each estimate of instantaneous phase and instantaneous amplitude is computed on a millisecond timescale.

7. The method of claim 3, wherein, for each estimate in the set of estimates of instantaneous phase and instantaneous amplitude, the calculating comprises:
   (a) reconstructing, by an inverse discrete Fourier transform, a specific sample of the measured electrical signal; and
   (b) computing a specific estimate based on the specific sample and not based on any other sample.

8. The method of claim 3, wherein the calculating of instantaneous phase and instantaneous amplitude comprises applying a causal filter in a frequency domain.

9. The method of claim 3, wherein, for each estimate in the set of one or more estimates of instantaneous phase and instantaneous amplitude, the method further comprises:
   (a) padding and filtering a specific sample window for a specific estimate to create a padded and filtered sample window, wherein a difference in value between data points at each end of the padded and filtered sample window is less than a difference in value between data points at each end of the sample window before padding and filtering; and
   (b) performing a discrete Fourier transform and Hilbert transform or zero-crossing method to calculate an analytic representation of the padded and filtered sample window.

10. The method of claim 3, wherein, for each estimate in the set of one or more estimates of instantaneous phase and instantaneous amplitude, the method further comprises:
    (a) adding padding to a specific sample window for a specific estimate and then filtering the specific sample window to create a padded and filtered sample window; and
    (b) performing a discrete Fourier transform and Hilbert transform or zero-crossing method to calculate an analytic representation of the padded and filtered sample window.

11. The method of claim 1, wherein the endogenous pharmaceutically-induced slow-delta wave has a frequency between about 0.5 Hz and about 4 Hz.

12. The method of claim 1, wherein a topography of the phase-locked neurostimulation, a target frequency bandwidth, a stimulation phase, one or more stimulation modalities, or one or more stimulation intensities are directly adjusted by a user.

13. The method of claim 1, wherein the neurostimulation comprises:
    acoustic stimulation; or
    a combination of acoustic stimulation and at least one of electrical, magnetic, visual, and ultrasonic stimulation.

14. The method of claim 1, wherein the neurostimulation causes the subject to perceive binaural beats.

15. The method of claim 1, wherein the slow-delta wave enhancing agent comprises an anesthetic agent.

16. The method of claim 15, wherein the anesthetic agent is a barbiturate or inhaled ether.

17. The method of claim 15, wherein the anesthetic agent is selected from the group consisting of propofol, dexmedetomidine, ketamine, remifentanil, nitrous oxide, desflurane, etomidate, sevoflurane, isoflurane, and combinations thereof.

18. The method of claim 15, wherein the anesthetic agent is a combination of anesthetic agents selected from the group consisting of: propofol/remifentanil, propofol/dexmedetomidine, dexmedetomidine/remifentanil, sevoflurane/remifentanil, sevoflurane/nitrous oxide, ketamine/remifentanil, and ketamine/propofol, and combinations thereof.

19. The method of claim 1, wherein the slow-delta wave enhancing agent is selected from the group consisting of gamma hydroxybutyrate (GHB), trazodone, brexanolone, propofol, benzodiazepines, barbiturates, xenon, nitrous oxide, ketamine, halogenated ethers, and combinations thereof.

20. The method of claim 1, wherein applying the neurostimulation results in enhanced or more stable unconsciousness in the subject when compared to not applying the neurostimulation.

21. The method of claim 1, wherein applying the neurostimulation results in a reduced dose of the at least one pharmacological agent required for maintaining unconsciousness in the subject.

22. The method of claim 1, wherein the applying the neurostimulation enhances GABAergic activity, activates opioid receptors, activates alpha-2 receptors, or inhibits NMDA receptors.

23. The method of claim 1, wherein the at least one pharmacological agent induces sleep or an anesthetic state.

* * * * *